(12) United States Patent
Koehn et al.

(10) Patent No.: US 9,204,650 B2
(45) Date of Patent: Dec. 8, 2015

(54) N-(1,2,5-OXADIAZOL-3-YL)-, N-(1,3,4-OXADIAZOL-2-YL)-, N-(TETRAZOL-5-YL)-, AND N-(TRIAZOL-5-YL) ARYL CARBOXYLIC ACID AMIDES AND USE THEREOF AS HERBICIDES

(71) Applicant: BAYER INTELLECTUAL PROPERTY GMBH, Monheim (DE)

(72) Inventors: Armin Koehn, Klein-Winternheim (DE); Stefan Lehr, Lyons (FR); Ralf Braun, Ramberg (DE); Simon Doerner-Rieping, Neu-Anspach (DE); Hartmut Ahrens, Egelsbach (DE); Hansjoerg Dietrich, Liederbach am Taunus (DE); Isolde Haeuser-Hahn, Leverkusen (DE); Christopher Hugh Rosinger, Hofheim (DE); Elmar Gatzweiler, Bad Nauheim (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/363,389

(22) PCT Filed: Dec. 10, 2012

(86) PCT No.: PCT/EP2012/074975
§ 371 (c)(1),
(2) Date: Jun. 6, 2014

(87) PCT Pub. No.: WO2013/087577
PCT Pub. Date: Jun. 20, 2013

(65) Prior Publication Data
US 2014/0371068 A1 Dec. 18, 2014

(30) Foreign Application Priority Data
Dec. 13, 2011 (EP) .................................. 11193166

(51) Int. Cl.
| | | |
|---|---|---|
| C07D 257/06 | (2006.01) |
| A01N 43/713 | (2006.01) |
| A01N 43/82 | (2006.01) |
| C07D 403/12 | (2006.01) |
| C07D 401/12 | (2006.01) |
| C07D 405/12 | (2006.01) |
| C07D 413/04 | (2006.01) |
| C07D 413/06 | (2006.01) |
| C07D 413/12 | (2006.01) |
| C07D 271/08 | (2006.01) |
| C07D 271/10 | (2006.01) |
| A01N 43/80 | (2006.01) |

(52) U.S. Cl.
CPC ............. *A01N 43/82* (2013.01); *A01N 43/713* (2013.01); *A01N 43/80* (2013.01); *C07D 257/06* (2013.01); *C07D 271/08* (2013.01); *C07D 271/10* (2013.01); *C07D 401/12* (2013.01); *C07D 403/12* (2013.01); *C07D 405/12* (2013.01); *C07D 413/04* (2013.01); *C07D 413/06* (2013.01); *C07D 413/12* (2013.01)

(58) Field of Classification Search
CPC ............................ C07D 257/06; A01N 43/713
USPC ........................................... 548/251; 504/261
See application file for complete search history.

(56) References Cited

U.S. PATENT DOCUMENTS 8,288,316 B2  10/2012  Köhn et al.

FOREIGN PATENT DOCUMENTS

| EP | 0049071 A1 | 4/1982 |
| JP | 1009978 A | 1/1989 |
| WO | 0031066 A1 | 6/2000 |
| WO | 2011035874 A1 | 3/2011 |

OTHER PUBLICATIONS

Dorwald, Side Reactions in Organic Synthesis, 2005, Wiley: VCH Weinheim Preface, pp. 1-15 & Chapter 8, pp. 279-308.*
International Search Report received in PCT/EP2012/074975 mailed Feb. 27, 2013.
Bowden et al., Structure-Activity Relations, Part 10, Metal ion complexation studies of a series of substituted benzamidotetrazoles, Journal of Chemical Research, Science Reviews Ltd., GB, Jan. 1, 1991, p. 304.
Werber et al., Nucleophilic behaviour of some 1,3,4-oxadiazoles in benzoylation, nitrosation, acetylation, and methylation reactions, Journal of Heterocyclic Chemistry, vol. 9, No. 1, Feb. 1, 1972, pp. 107-109.

* cited by examiner

*Primary Examiner* — Patricia L Morris
(74) *Attorney, Agent, or Firm* — Miles & Stockbridge P.C.

(57) ABSTRACT

N-(1,2,5-Oxadiazol-3-yl)-, N-(1,3,4-oxadiazol-2-yl)-, N-(tetrazol-5-yl)- or N-(triazol-5-yl)arylcarboxamides of the general formula (I) are described as herbicides.

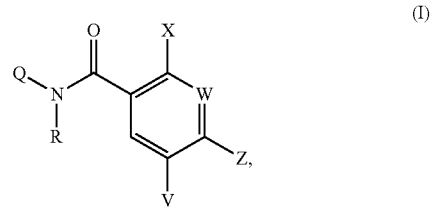

In this formula (I), R, V, X, Y and Z are radicals such as hydrogen, organic radicals such as alkyl, and other radicals such as halogen. Q is a tetrazolyl, triazolyl or oxadiazolyl radical. W is CY or N.

6 Claims, No Drawings

N-(1,2,5-OXADIAZOL-3-YL)-, N-(1,3,4-OXADIAZOL-2-YL)-, N-(TETRAZOL-5-YL)-, AND N-(TRIAZOL-5-YL) ARYL CARBOXYLIC ACID AMIDES AND USE THEREOF AS HERBICIDES

CROSS REFERNCE TO RELATED APPLICATIONS

This application is a §371 National Stage Application of PCT/EP2012/074975, filed Dec. 10, 2012 which claims priority to EP 11193166.3, filed Dec. 13, 2011.

BACKGROUND

1. Field of the invention

The invention relates to the technical field of herbicides, especially that of herbicides for selective control of broadleaved weeds and weed grasses in crops of useful plants.

2. Description of Related Art

WO 2003/010143 A1 and WO 2003/010153 A1 disclose N-(tetrazol-5-yl)- and N-(triazol-5-yl)benzamides and their pharmacological activity. EP 0 049 071 A1 discloses N-arylbenzamides having pharmacological activity. J. Chem. Res. (S) 1991, 11, 304 describes the compounds 2-methoxy-N-methyl-N-(1H-tetrazol-5-yl)benzamide, 2-hydroxy-N-methyl-N-(1H-tetrazol-5-yl)benzamide, 2-methoxy-N-methyl-N-(1-methyl-1H-tetrazol-5-yl)benzamide and 2-methoxy-N-(2-methyl-2H-tetrazol-5-yl)benzamide having pharmacological activity.

WO 00/31066 A1 describes N-pyrazolylphenoxynicotinamides or -thionicotinamides having herbicidal activity. JP1989009978(A) discloses N-isoxazolylbenzamides having herbicidal activity. N-(1,2,5-Oxadiazol-3-yl)benzamides as herbicides are known from WO 2011/035874 A1. European patent application EP101748937, which has an earlier priority date but was yet to be published before the priority date of the present application, discloses particular N-(tetrazol-5-yl)- and N-(triazol-5-yl)benzamides and -nicotinamides as herbicides. However, the herbicidal activity and/or the crop plant compatibility of the compounds specified in these publications is not always adequate. J. Het. Chem. 1972, 9, 107-109 mentions the compound N-methyl-N-(5-phenyl-1,3,4-oxadiazol-2-yl)benzamide. No herbicidal activity of this compound is disclosed. Under CAS number 931735-86-3, the compound 3-bromo-4-methoxy-N-methyl-N-(5-phenyl-1,3,4-oxadiazol-2-yl)benzamide is known. No herbicidal activity of this compound is disclosed.

SUMMARY

It is an object of the present invention to provide herbicidally active compounds having properties improved over those of the compounds disclosed in the prior art.

It has now been found that benzoylamides substituted by particular radicals on the nitrogen atom are of particularly good suitability as herbicides.

The present invention thus provides N-(1,2,5-oxadiazol-3-yl)-, N-(1,3,4-oxadiazol-2-yl)-, N-(tetrazol-5-yl)- and N-(triazol-5-yl)arylcarboxamides of the formula (I) or salts thereof

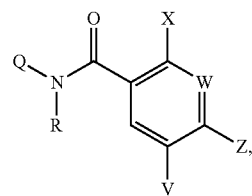

in which the symbols and indices are each defined as follows:
R is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$C(O)R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $OR^1$, $COOR^1$, $CON(R^1)_2$, $N(R^1)_2$, $NR^1COOR^1 NR^1CON(R^1)_2$ or
benzyl in each case substituted by s radicals from the group of methyl, ethyl, methoxy, nitro, trifluoromethyl and halogen,
W is N or CY,
X and Z are each independently hydrogen, nitro, halogen, cyano, formyl, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $(C_3-C_6)$-halocycloalkyl, $(C_3-C_6)$-cycloalkyl-$(C_1-C_6)$-alkyl, $(C_3-C_6)$-halocycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$COOR^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, or
heteroaryl, heterocyclyl or phenyl, each substituted by s radicals from the group of methyl, ethyl, methoxy, nitro, trifluoromethyl and halogen,
Y is hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)N(R^1)OR^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-CN, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, CH=$NOR^1$, $(C_1-C_6)$-alkyl-CH=$NOR^1$, $(C_1-C_6)$-alkyl-O—N=$C(R^1)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the 6 latter radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl bears n oxo groups, or
Y and Z together with the two atoms to which they are bonded form a 5-, 6- or 7-membered, unsaturated, partly saturated or saturated ring which, as well as carbon atoms, in each case has s nitrogen atoms, n oxygen atoms, n sulfur atoms and n S(O), S(O)$_2$, C=N—R$^{17}$, C(OR$^{17}$)$_2$, C[—O—(CH$_2$)$_2$—O—] or C(O) elements as ring members, wherein the carbon atoms are substituted by s radicals from the group consisting of halogen, cyano, (C$_1$-C$_6$)-alkyl, (C$_2$-C$_{10}$)-alkenyl, (C$_2$-C$_{10}$)-alkynyl, (C$_1$-C$_6$)-haloalkyl, (C$_1$-C$_6$)-alkoxy, phenoxy, halo-(C$_1$-C$_6$)-alkoxy, (C$_3$-C$_8$)-cycloalkyl, (C$_2$-C$_8$)-alkoxyalkyl and phenyl, wherein the nitrogen atoms are substituted by n radicals from the group consisting of (C$_1$-C$_6$)-alkyl and phenyl, and in which the aforementioned phenyl radicals are substituted by s radicals from the group consisting of cyano, nitro, halogen, (C$_1$-C$_6$)-alkyl, (C$_1$-C$_6$)-haloalkyl and (C$_1$-C$_6$)-alkoxy, V is hydrogen, nitro, halogen, cyano, (C$_1$-C$_4$)-alkyl, (C$_1$-C$_4$)-haloalkyl, OR$^1$, S(O)$_n$R$^2$, R$^1$ is hydrogen, (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocycl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl, (C$_1$-C$_6$)-alkyl-NR$^3$-heterocyclyl, where the 21 latter radicals are substituted by s radicals from the group consisting of cyano, halogen, nitro, thiocyanato, OR$^3$, S(O)$_n$ R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^2$ is (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_6$)-cycloalkyl, (C$_3$-C$_6$)-cycloalkenyl, (C$_3$-C$_6$)-halocycloalkyl, (C$_1$-C$_6$)-alkyl-O—(C$_1$-C$_6$)-alkyl, (C$_3$-C$_6$)-cycloalkyl-(C$_1$-C$_6$)-alkyl, phenyl, phenyl-(C$_1$-C$_6$)-alkyl, heteroaryl, (C$_1$-C$_6$)-alkylheteroaryl, heterocyclyl, (C$_1$-C$_6$)-alkylheterocyclyl, (C$_1$-C$_6$)-alkyl-O-heteroaryl, (C$_1$-C$_6$)-alkyl-O-heterocyclyl, (C$_1$-C$_6$)-alkyl-NR$^3$-heteroaryl, (C$_1$-C$_6$)-alkyl-NR$^3$-heterocyclyl, where the 21 latter radicals are substituted by s radicals from the group consisting of cyano, halogen, nitro, thiocyanato, OR$^3$, S(O)$_n$R$^4$, N(R$^3$)$_2$, NR$^3$OR$^3$, COR$^3$, OCOR$^3$, SCOR$^4$, NR$^3$COR$^3$, NR$^3$SO$_2$R$^4$, CO$_2$R$^3$, COSR$^4$, CON(R$^3$)$_2$ and (C$_1$-C$_4$)-alkoxy-(C$_2$-C$_6$)-alkoxycarbonyl, and where heterocyclyl bears n oxo groups, R$^3$ is hydrogen, (C$_1$-C$_6$)-alkyl, (C$_2$-C$_6$)-alkenyl, (C$_2$-C$_6$)-alkynyl, (C$_3$-C$_6$)-cycloalkyl or (C$_3$-C$_6$)-cycloalkyl-(C$_1$-C$_6$)-alkyl, R$^4$ is (C$_1$-C$_6$)-alkyl, (C$_2$-C$_6$)-alkenyl or (C$_2$-C$_6$)-alkynyl, (C$_3$-C$_6$)-cycloalkyl or (C$_3$-C$_6$)-cycloalkyl-(C$_1$-C$_6$)-alkyl, R$^5$ is (C$_1$-C$_4$)-alkyl, n is 0, 1 or 2, s is 0, 1, 2 or 3, Q is a Q1, Q2, Q3 or Q4 radical, (Q1)

(Q2)

(Q3)

(Q4)

R$^6$ is (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, where these 6 aforementioned radicals are each substituted by s radicals from the group consisting of nitro, cyano, SiR$^{12}$$_3$, PO(OR$^{12}$)$_3$, S(O)$_n$—(C$_1$-C$_6$)-alkyl, (C$_1$-C$_6$)-alkoxy, halo-(C$_1$-C$_6$)-alkoxy, N(R$^{10}$)$_2$, COR$^{10}$, COOR$^{10}$, OCOR$^{10}$, OCO$_2$R$^{10}$, NR$^{10}$COR$^{10}$, NR$^{10}$SO$_2$R$^{11}$, (C$_3$-C$_6$)-cycloalkyl, heteroaryl, heterocyclyl, phenyl, D-heteroaryl, D-heterocyclyl, D-phenyl and D-benzyl, and where the 7 latter radicals are substituted by s radicals from the group of methyl, ethyl, methoxy, trifluoromethyl and halogen, and where heterocyclyl bears n oxo groups, or R$^6$ is (C$_3$-C$_7$)-cycloalkyl, heteroaryl, heterocyclyl or phenyl, each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, R$^7$ is (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_2$-C$_6$)-alkynyl, where these 6 aforementioned radicals are each substituted by s radicals from the group consisting of nitro, cyano, SiR$^{12}$$_3$, PO(OR$^{12}$)$_3$, S(O)$_n$—(C$_1$-C$_6$)-alkyl, (C$_1$-C$_6$)-alkoxy, halo-(C$_1$-C$_6$)-alkoxy, N(R$^{10}$)$_2$, COR$^{10}$, COOR$^{10}$, OCOR$^{10}$, OCO$_2$R$^{10}$, NR$^{10}$COR$^{10}$, NR$^{10}$SO$_2$R$^{11}$, (C$_3$-C$_6$)-cycloalkyl, heteroaryl, heterocyclyl, phenyl, D-heteroaryl, D-heterocyclyl, D-phenyl and D-benzyl, and where the 7 latter radicals are substituted by s radicals from the group of methyl, ethyl, methoxy, trifluoromethyl and halogen, and where heterocyclyl bears n oxo groups, or R$^7$ is (C$_3$-C$_7$)-cycloalkyl, heteroaryl, heterocyclyl or phenyl, each substituted by s radicals from the group consisting of halogen, nitro, cyano, (C$_1$-C$_6$)-alkyl, halo-(C$_1$-C$_6$)-alkyl, (C$_3$-C$_6$)-cycloalkyl, S(O)$_n$—(C$_1$-C$_6$)-alkyl, (C$_1$-C$_6$)-alkoxy, halo-(C$_1$-C$_6$)-alkoxy and (C$_1$-C$_6$)-alkoxy-(C$_1$-C$_4$)-alkyl, R$^8$ is hydrogen, (C$_1$-C$_6$)-alkyl, (C$_3$-C$_7$)-cycloalkyl, halo-(C$_1$-C$_6$)-alkyl, (C$_1$-C$_6$)-alkoxy, halo-(C$_1$-C$_6$)-alkoxy, (C$_2$-C$_6$)-alkenyl, (C$_2$-C$_6$)-alkenyloxy, halo-(C$_2$-C$_6$)-alkenyl, (C$_2$-C$_6$)-alkynyl, (C$_2$-C$_6$)-alkynyloxy, halo-(C$_2$-C$_6$)-alkynyl, cyano, nitro, methylsulfenyl, methylsulfinyl, methylsulfonyl, (C$_1$-C$_6$)-alkylcarbonylamino, (C$_1$-C$_6$)-alkoxycarbonylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each substituted by s radicals from the group consisting of methyl, ethyl, methoxy, trifluoromethyl and halogen;

$R^9$ is hydrogen, $(C_1-C_6)$-alkyl, $R^{13}O-(C_1-C_6)$-alkyl, $CH_2R^{14}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^{13}$, $NHR^{13}$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl or heteroaryl, heterocyclyl, benzyl or phenyl, each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n-(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{10}$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl or phenyl, $R_{11}$ is $(C_1-C_6)$-alkyl, $(C_2-C_6)$-alkenyl, $(C_2-C_6)$-alkynyl or phenyl, $R_{12}$ is $(C_1-C_6)$-alkyl, $R^{13}$ is hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O-$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{15}$-heteroaryl or $(C_1-C_6)$-alkyl-$NR^{15}$-heterocyclyl, where the 21 latter radicals are substituted by s radicals from the group consisting of cyano, halogen, nitro, thiocyanato, $OR^{15}$, $S(O)_nR^{16}$, $N(R^{15})_2$, $NR^{15}OR^{15}$, $COR^{15}$, $OCOR^{15}$, $SCOR^{16}$, $NR^{15}COR^{15}$, $NR^{15}SO_2R^{16}$, $CO_2R^{15}$, $COSR^{16}$, $CON(R^{15})_2$ and $(C_1-C_4)$-alkoxy-$(C_2-C_6)$-alkoxycarbonyl, and where heterocyclyl bears n oxo groups, $R_{14}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_3-C_6)$-alkoxy, $(C_3-C_6)$-cycloalkyl, or heteroaryl, heterocyclyl or phenyl, each substituted by s radicals from the group consisting of methyl, ethyl, methoxy, trifluoromethyl and halogen;

$R^{15}$ is hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^{16}$ is $(C_1-C_6)$-alkyl, $(C_2-C_6)$-alkenyl or $(C_2-C_6)$-alkynyl, $R^{17}$ is $(C_1-C_6)$-alkyl, halo-$(C_1-C_6)$-alkyl, $(C_1-C_6)$-alkoxy and halo-$(C_1-C_6)$-alkoxy, s is 0, 1, 2 or 3, n is 0, 1 or 2, D is O, S, or $NR^{11}$, excluding the compounds 2-methoxy-N-methyl-N-(1H-tetrazol-5-yl)benzamide, 2-hydroxy-N-methyl-N-(1H-tetrazol-5-yl)benzamide, 2-methoxy-N-methyl-N-(1-methyl-1H-tetrazol-5-yl)benzamide, 2-methoxy-N-(2-methyl-2H-tetrazol-5-yl)benzamide, N-methyl-N-(5-phenyl-1,3,4-oxadiazol-2-yl)benzamide and 3-bromo-4-methoxy-N-methyl-N-(5-phenyl-1,3,4-oxadiazol-2-yl)benzamide.

DETAILED DESCRIPTION OF A PREFERRED EMBODIMENT

Of particular interest are N-(1,3,4-oxadiazol-2-yl)-, N-(tetrazol-5-yl)- and N-(triazol-5-yl)arylcarboxamides of the formula (I) or salts thereof in which Q is a Q1, Q2 or Q4 radical,

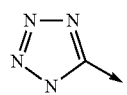
(Q1)

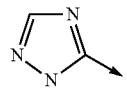
(Q2)

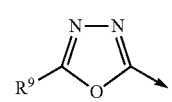
(Q4)

and all the other radicals and indices have the respective definitions given above.

Of very particular interest are N-(1,3,4-oxadiazol-2-yl)- and N-(tetrazol-5-yl)arylcarboxamides of the formula (I) or salts thereof in which Q is a Q1 or Q4 radical,

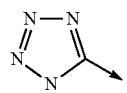
(Q1)

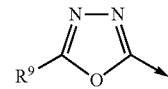
(Q4)

and all the other radicals and indices have the respective definitions given above.

Preference is given to N-(tetrazol-5-yl)arylcarboxamides of the formula (I) or salts thereof in which Q is the Q1 radical,

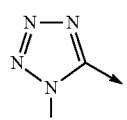
(Q1)

and all the other radicals and indices have the respective definitions given above.

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl, Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3, 4-tetrazolyl, 1H-1,2,3,4-tetrazolyl, 1,2,3,4-oxatriazolyl, 1,2, 3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. This applies analogously to the construction of ring systems from various atoms and elements. Here, compounds known to the person skilled in the art to be chemically unstable under standard conditions are meant to be excluded from the scope of the claims.

Depending on the nature and the attachment of the substituents, the compounds of the formula (I) may be present as stereoisomers. When, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the general formula (I) but not defined specifically. Owing to the oxime ether structure, the inventive compounds may also be present as geometric isomers (E/Z isomers). The invention also relates to all E/Z isomers and mixtures thereof which are encompassed by the general formula (I) but not defined specifically.

The compounds of the formula (I) may form salts. Salts can be formed by the action of a base on those compounds of the formula (I) which bear an acidic hydrogen atom, for example in the case that $R^1$ contains a COOH group or a sulfonamide group —NHSO$_2$—. Suitable bases are, for example, organic amines such as trialkylamines, morpholine, piperidine or pyridine, and also ammonium, alkali metal or alkaline earth metal hydroxides, carbonates and hydrogencarbonates, especially sodium and potassium hydroxide, sodium and potassium carbonate and sodium and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R"R'"]$^+$ in which R to R'" are each independently of one another an organic radical, especially alkyl, aryl, aralkyl or alkylaryl. Also useful are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts by addition of a suitable inorganic or organic acid, for example mineral acids, for example HCl, HBr, H$_2$SO$_4$, H$_3$PO$_4$ or HNO$_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. These salts then contain the conjugate base of the acid as the anion.

Inventive compounds can be prepared, for example, according to the method shown in scheme 1, by reacting an N-(1,2,5-oxadiazol-3-yl)-, N-(1,3,4-oxadiazol-2-yl)-, N-(tetrazol-5-yl)- or N-(triazol-5-yl)arylcarboxamide (II) with a compound of the general formula (III) where L is a leaving group, for example a chlorine, bromine, iodine, mesyloxy, tosyloxy, trifluorosulfonyloxy, etc.:

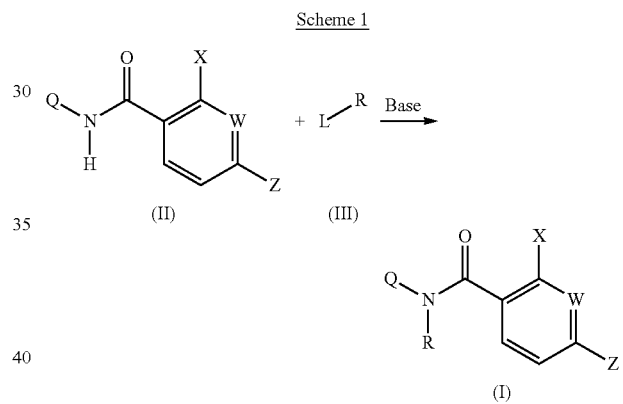

The N-(1,2,5-oxadiazol-3-yl)arylcarboxamides of the formula (II) are known in principle and can be prepared by the methods described in WO 20011/035874 A1.

The compounds of the formula (III) in which L is a leaving group, for example chlorine, bromine, iodine, methylsulfonyloxy, tosyloxy or trifluorosulfonyloxy are either commercially available or can be prepared by known methods described in the literature.

Inventive compounds can also be prepared according to the method shown in scheme 2 by reaction of an amine of the formula (IV) with an acid chloride (V), as described, for example, in J. Het. Chem. (1972), 9 (1), 107-109):

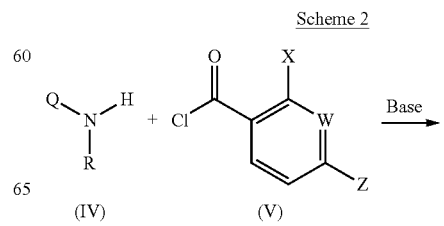

-continued

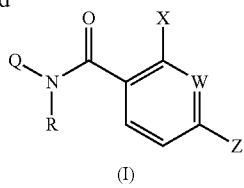

Inventive compounds can also be prepared according to the method shown in scheme 3, by reaction of an amine of the formula (IV) with an acid of the formula (VI):

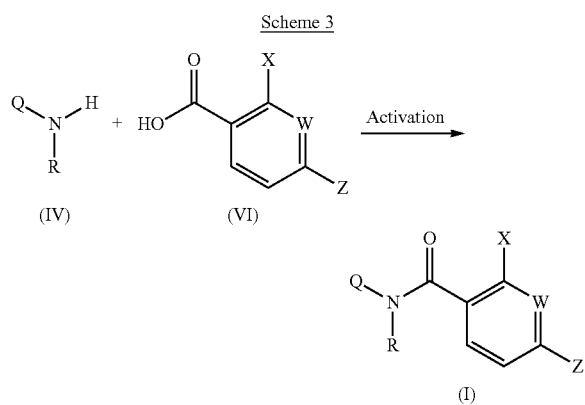

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

The benzoyl chlorides of the formula (V) or their parent benzoic acids of the formula (VI) are known in principle and can be prepared, for example, by the methods described in U.S. Pat. No. 6,376,429 B1, EP 1 585 742 A1 and EP 1 202 978 A1.

The amines of the formula (IV) are either commercially available or known in the literature or can be prepared, for example, by the methods described in scheme 4, by base-catalyzed alkylation or by reductive alkylation, or according to the method described in scheme 5, by nucleophilic substitution of a leaving group L by amines R—NH$_2$.

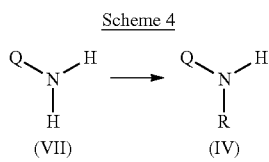

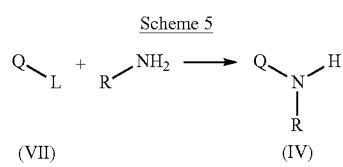

The amines of the formula (IV) can also be prepared by cyclization reactions as described, for example, in J. Org. Chem. 73(10), 3738-3744 (2008) where Q=Q1, or in Buletinul Institutului Politehnic din Iasi (1974), 20(1-2), 95-99 or in J. Org. Chem. 67(21), 7361-7364 (2002) where Q=Q4.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The technical literature describes a number of experimental protocols, for example ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The technical literature describes a number of experimental protocols, for example in Microwaves in Organic and Medicinal Chemistry (editors: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual weed plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

If the inventive compounds are applied to the soil surface before germination, either the weed seedlings are prevented completely from emerging or the weeds grow until they have reached the cotyledon stage, but then stop growing and, eventually, after three to four weeks have passed, die completely.

If the active ingredients are applied post-emergence to the green parts of the plants, there is likewise stoppage of growth after the treatment, and the weed plants remain at the growth stage of the time of application, or they die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* especially *Zea* and *Triticum,* are damaged only to an insignificant extent, if at all, depending on the structure of the respective inventive compound and the application rate thereof. For these reasons, the present compounds are very suitable for selective control of unwanted plant growth in plant crops such as agriculturally useful plants or ornamentals.

In addition, the inventive compounds (depending on their particular structure and the application rate deployed) have outstanding growth-regulating properties in crop plants. They intervene in the plant's own metabolism with a regulatory effect, and can thus be used to control plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant growth-regulating properties, the active ingredients can also be used for control of weed plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

With regard to transgenic crops, preference is given to the use of the inventive compounds in economically important transgenic crops of useful plants and ornamentals, for example of cereals such as wheat, barley, rye, oats, millet/sorghum, rice and corn, or else crops of sugar beet, cotton, soybean, oilseed rape, potato, tomato, peas and other vegetables. Preferably, the inventive compounds can be used as herbicides in crops of useful plants which are resistant, or have been made resistant by recombinant means, to the phytotoxic effects of the herbicides.

Preference is given to the use of the inventive compounds or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the inventive compounds can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP- A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, NY; or Winnacker "Gene and Klone", VCH Weinheim, 2nd edition, 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. To this end, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. The use of DNA sequences which have a high degree of homology to the coding sequences of a gene product, but are not completely identical to them, is also possible.

When expressing nucleic acid molecules in plants, the protein synthesized may be localized in any compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the inventive active ingredients in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of weed plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], volume 7, C. Hanser Verlag Munich, 4th edition 1986, Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal ingredients are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or granulated inert material. Suitable active ingredients can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight, the remainder to 100% consisting of customary formulation constituents. In emulsifiable concentrates, the active ingredient concentration may be about 1 to 90% and preferably 5 to 80% by weight. Dust-type formulations contain 1 to 30% by weight of active ingredient, preferably usually 5 to 20% by weight of active ingredient; sprayable solutions contain about 0.05 to 80% and preferably 2 to 50% by weight of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 14th edition, The British Crop Protection Council and the Royal Soc. of Chemistry, 2003 and literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

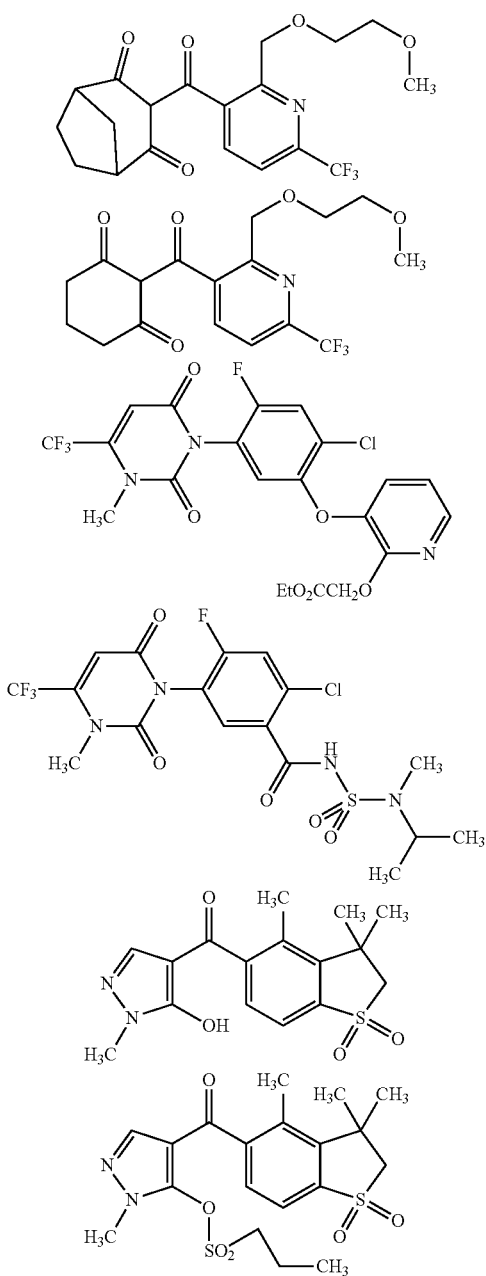

A. CHEMICAL EXAMPLES

Synthesis of N-ethyl-2-methyl-3-(methylsulfonyl)-N-(1-methyl-1H-tetrazol-5-yl)-4-(trifluoromethyl)benzamide (Table Example No. A-2)

100 mg (0.275 mmol) of 2-methyl-3-(methylsulfonyl)-N-(1-methyl-1H-tetrazol-5-yl)-4-(trifluoromethyl)benzamide and 43 mg (0.275 mmol) of iodoethane are dissolved in 5 ml of N,N-dimethylformamide, and 0.038 mg (0.275 mmol) of potassium carbonate is added. The reaction mixture is stirred at 80° C. for 16 h and taken up in 5 ml of water and extracted twice with 10 ml each time of dichloromethane. The organic phase is dried over $Na_2SO_4$ and concentrated. The residue is purified by means of preparative HPLC (acetonitrile, water). Yield 30 mg (26%).

$^1$H NMR (400 MHz; $CDCl_3$): 7.96 ppm (d, 0.5 H); 7.7 ppm (d, 0.5H), 7.67 (d, 0.5H), 7.38 (d; 0.5H); 4.10-3.61 (m, 5H); 3.28 (s, 1.5H); 3.18 (s, 1.5H); 2.83 (s, 3H); 1.32 (t; 1.5H), 1.11 (s; 1.5H).

Synthesis of 2-chloro-3-[5-(cyanomethyl)-4,5-dihydro-1,2-oxazol-3-yl]-4-(ethylsulfonyl)-N-(1-methyl-1H-tetrazol-5-yl)benzamide (Table Example No. A12)

178 mg (0.5 mmol) of 2-chloro-3-[5-(cyanomethyl)-4,5-dihydro-1,2-oxazol-3-yl]-4-(ethylsulfonyl)benzoic acid and 90 mg (0.65 mmol) of N-allyl-1-methyl-1H-tetrazol-5-amine are stirred in 3 ml of pyridine at room temperature (RT) for 1 h, and then a solution of 86 mg (0.675 mmol) of oxalyl chloride in 2 ml of dichloroethane is added. Subsequently, the mixture is stirred at 75° C. for 4 h. After cooling to RT, 0.5 ml of water is added. Then the mixture is stirred at RT for 30 min. The reaction solution is filtered and concentrated. The residue is purified by means of preparative HPLC (acetonitrile/water). Yield: 19 mg (8%).

$^1$H NMR (400 MHz; DMSO-$d_6$): 8.23; 8.15; 7.90 and 7.82; (4d, 2 H); 5.88 (m, 1H), 5.42-4.98 (m, 3H), 4.55 (bs, 1H), 4.29 (d, 1H), 4.10 and 4.04 (2s, 3H), 3.67-2.98 (m, 7H), 1.18 and 1.04 (2t, 3H).

Synthesis of methyl [2-(methylsulfonyl)-4-(trifluoromethyl)benzoyl](1-methyl-1H-tetrazol-5-yl)carbamate (Table Example No. A14)

To a solution of 175 mg (0.5 mmol) of 2-(methylsulfonyl)-N-(1-methyl-1H-tetrazol-5-yl)-4-(trifluoromethyl)benzamide in 4 ml of THF (abs.) under protective gas at 0° C. are added 14 mg (0.55 mmol) of sodium hydride (95%). After stirring for 10 min, 46 µl (0.6 mmol) of methyl chloroformate are added at 0° C. The reaction mixture is stirred at RT for 1 h. Subsequently, the reaction mixture is adjusted to pH 7 with an aqueous sat. sodium hydrogencarbonate solution, and 10 ml of water are added. Then the mixture is extracted with ethyl acetate. The organic phase is dried over sodium sulfate, filtered and concentrated. Yield: 231 mg (57%)

$^1$H NMR (400 MHz; DMSO-$d_6$): 8.40 (s, 1H), 8.31 (d, 1H), 8.15 (d, 1H), 4.14 (s, 3H), 3.67 (s, 3H); 3.38 (s, 3H).

Synthesis of N-allyl-2-methyl-N-(4-methyl-1,2,5-oxadiazol-3-yl)-3-(methylsulfonyl)-4-(trifluoromethyl)benzamide (Table Example No. C-1)

150 mg (0.413 mmol) of 2-methyl-N-(4-methyl-1,2,5-oxadiazol-3-yl)-3-(methylsulfonyl)-4-(trifluoromethyl)benzamide and 50 mg (0.413 mmol) of allyl bromide are dissolved For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

The examples which follow illustrate the invention.

in 5 ml of N,N-dimethylformamide, and 0.057 mg (0.413 mmol) of potassium carbonate is added. The reaction mixture is stirred at 80° C. for 8 h and taken up in 5 ml of water and extracted twice with 10 ml each time of dichloromethane. The organic phase is dried over $Na_2SO_4$ and concentrated. The residue is purified by means of preparative HPLC (acetonitrile, water). Yield 160 mg (86%).

$^1$H NMR (400 MHz; DMSO-$d_6$): 8.10-8.01 ppm (b, 1 H); 7.84 ppm (d, 0.5H), 7.75 (d, 0.5H), 7.38 (d, 0.5H); 5.98-5.75 (m, 1H); 5.38 (d, 0.5H); 5.26 (d, 0.5H); 5.14 (d, 0.5H); 5.02 (d, 0.5H); 4.19 (d, 2H); 3.46 (s, 1.5H); 3.30 (s; 1.5H), 2.89 (s; 1.5H); 2.70 (s, 1.5H); 2.43 (s, 3H).

Synthesis of N-methyl-N-(5-methyl-1,3,4-oxadiazol-2-yl)-2-methyl-3-(methylsulfonyl)-4-(trifluoromethyl)benzamide (Table Example No. D1)

180 mg (0.495 mmol) of 2-methyl-N-(5-methyl-1,3,4-oxadiazol-2-yl)-3-(methylsulfonyl)-4-(trifluoromethyl)benzamide are dissolved in 6 ml of DMF (abs.), and 68 mg (0.495 mmol) of $K_2CO_3$ and 0.047 ml (0.495 mmol) of dimethyl sulfate are added. The reaction mixture is boiled under reflux for 15 hours. Then the mixture is filtered, and the filtrate is concentrated and purified by column chromatography (silica gel; heptane/ethyl acetate).

$^1$H NMR (400 MHz; CDCl$_3$): 7.98 (d, 1H), 7.49 (d, 1H), 3.57 (bs, 3H), 3.23 (s, 3H), 2.92 (s, 3H), 2.37 (s, 3H).

The examples listed in the tables below were prepared analogously to the abovementioned methods or are obtainable analogously to the abovementioned methods. The compounds specified in the tables which follow, tables 1 to 336, which are obtainable analogously to the methods specified here, are particularly preferred.

The abbreviations used mean:

| Et = ethyl | Me = methyl | n-Pr = n-propyl | i-Pr = isopropyl |
|---|---|---|---|
| c-Pr = cyclopropyl | Ph = phenyl | Bn = benzyl | Prg = propargyl |

TABLE 1

Inventive compounds of the formula (I) in which in which Q is Q1, $R^6$ is methyl, X is chlorine, W is C—Y, Y is (2,2,2-trifluoroethoxy)methyl, V is hydrogen and Z is methylsulfonyl:

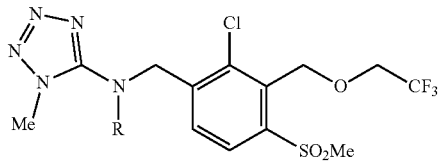

| No. | R | Physical data, ($^1$H NMR, DMSO-$d_6$, 400 MHz) |
|---|---|---|
| 1-1 | Me | |
| 1-2 | Et | |
| 1-3 | i-Pr | |
| 1-4 | CH$_2$CHF$_2$ | |
| 1-5 | CH$_2$CF$_3$ | |
| 1-6 | CH$_2$OMe | |
| 1-7 | CH$_2$OEt | |
| 1-8 | CH$_2$OPh | |
| 1-9 | CH$_2$SMe | |
| 1-10 | CH$_2$SEt | |
| 1-11 | CH$_2$SPh | |
| 1-12 | CH$_2$SO$_2$Me | |
| 1-13 | CH$_2$CH$_2$CN | |
| 1-14 | CH$_2$CH$_2$OMe | |

TABLE 1-continued

Inventive compounds of the formula (I) in which in which Q is Q1, $R^6$ is methyl, X is chlorine, W is C—Y, Y is (2,2,2-trifluoroethoxy)methyl, V is hydrogen and Z is methylsulfonyl:

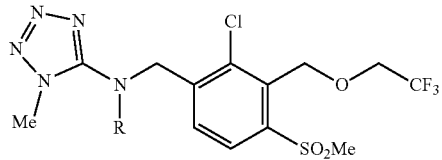

| No. | R | Physical data, ($^1$H NMR, DMSO-$d_6$, 400 MHz) |
|---|---|---|
| 1-15 | CH$_2$CH$_2$OEt | |
| 1-16 | CH$_2$CH$_2$OPh | |
| 1-17 | CH$_2$CH$_2$SMe | |
| 1-18 | CH$_2$CH$_2$S(O)Me | |
| 1-19 | CH$_2$CH$_2$SO$_2$Me | |
| 1-20 | CH$_2$CH$_2$SEt | |
| 1-21 | CH$_2$CH$_2$S(O)Et | |
| 1-22 | CH$_2$CH$_2$SO$_2$Et | |
| 1-23 | CH$_2$CH$_2$SPh | |
| 1-24 | CH$_2$CH$_2$S(O)Ph | |
| 1-25 | CH$_2$CH$_2$SO$_2$Ph | |
| 1-26 | CH$_2$C(O)Me | |
| 1-27 | CH$_2$C(O)Ph | |
| 1-28 | CH$_2$CO$_2$He | |
| 1-29 | CH$_2$CO$_2$Me | |
| 1-30 | CH$_2$CO$_2$Et | |
| 1-31 | CH$_2$CN | |
| 1-32 | CH$_2$CH$_2$CN | |
| 1-33 | allyl | |
| 1-34 | Prg | |
| 1-35 | benzyl | |
| 1-36 | CO$_2$Me | |
| 1-37 | CO$_2$Et | |
| 1-38 | CO$_2$-iPr | |
| 1-39 | CO$_2$CH$_2$—CHMe$_2$ | |
| 1-40 | CO$_2$CH$_2$-t-Bu | |

TABLE 2

Inventive compounds of the formula (I) in which Q is Q1, $R^6$ is ethyl, X is chlorine, W is C—Y, Y is (2,2,2-trifluoroethoxy)methyl, V is hydrogen and Z is methylsulfonyl, and R are as defined in table 1:

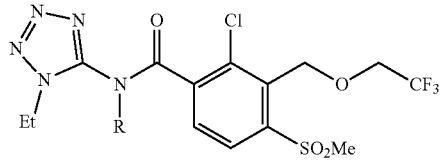

TABLE 3

Inventive compounds of the formula (I) in which Q is Q1, $R^6$ is methyl, X is chlorine, W is C—Y, Y is 4,5-dihydro-1,2-oxazol-3-yl, V is hydrogen and Z is methylsulfonyl, and R is as defined in table 1:

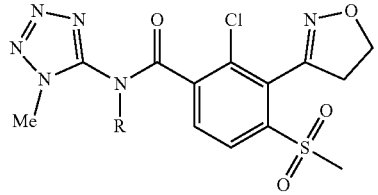

TABLE 4

Inventive compounds of the formula (I) in which Q is Q1, $R^6$ is methyl, X is chlorine, W is C—Y, Y is 4,5-dihydro-1,2-oxazol-3-yl, V is hydrogen and Z is ethylsulfonyl, and R is as defined in table 1:

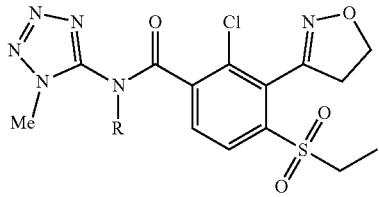

TABLE 5

Inventive compounds of the formula (I) in which Q is Q1, $R^6$ is methyl, X is chlorine, W is C—Y, Y is 5-cyanomethyl-4,5-dihydro-1,2-oxazol-3-yl, V is hydrogen and Z is ethylsulfonyl, and R is as defined in table 1:

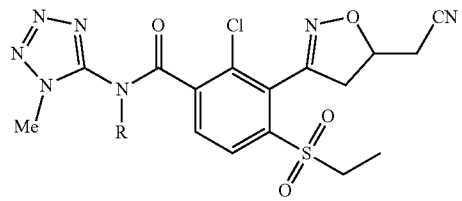

TABLE 6

Inventive compounds of the formula (I) in which Q is Q1, $R^6$ is methyl, X is chlorine, W is C—Y, Y is 5-(methoxymethyl)-4,5-dihydro-1,2-oxazol-3-yl, V is hydrogen and Z is ethylsulfonyl, and R is as defined in table 1:

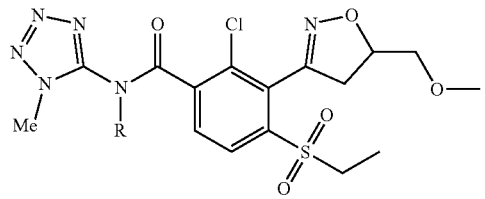

TABLE 7

Inventive compounds of the formula (I) in which Q is Q1, $R^6$ is methyl, X is chlorine, W is C—Y, Y is methoxymethyl, V is hydrogen and Z is methylsulfonyl, and R is as defined in table 1:

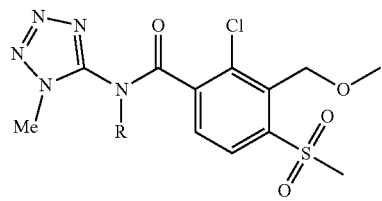

TABLE 8

Inventive compounds of the formula (I) in which Q is Q1, $R^6$ is ethyl, X is chlorine, W is C—Y, Y is ethoxymethyl, V is hydrogen and Z is methylsulfonyl, and R is as defined in table 1:

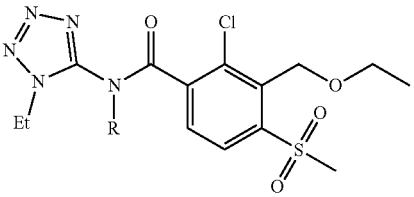

TABLE 9

Inventive compounds of the formula (I) in which Q is Q1, $R^6$ is methyl, X is chlorine, W is C—Y, Y is (2-methoxyethoxy)methyl, V is hydrogen and Z is methylsulfonyl, and R is as defined in table 1:

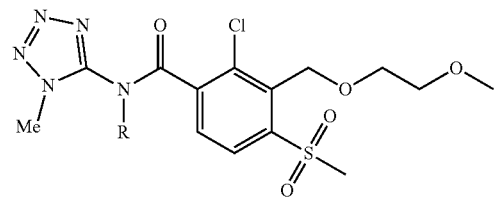

TABLE 10

Inventive compounds of the formula (I) in which Q is Q1, $R^6$ is methyl, X is chlorine, W is C—Y, Y is methoxy, V is hydrogen and Z is methylsulfonyl, and R is as defined in table 1:

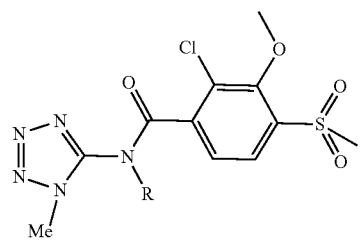

TABLE 11

Inventive compounds of the formula (I) in which Q is Q1, $R^6$ is methyl, X is chlorine, W is C—Y, Y is methoxy, V is hydrogen and Z is ethylsulfonyl, and R is as defined in table 1:

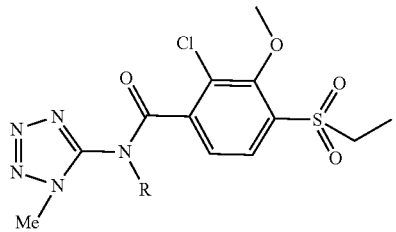

TABLE 12

Inventive compounds of the formula (I) in which Q is Q1, R⁶ is methyl, X is chlorine, W is C—Y, Y is ethoxy, V is hydrogen and Z is methylsulfonyl, and R is as defined in table 1:

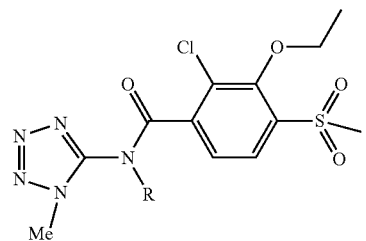

TABLE 13

Inventive compounds of the formula (I) in which Q is Q1, R⁶ is methyl, X is chlorine, W is C—Y, Y is ethoxy, V is hydrogen and Z is ethylsulfonyl, and R is as defined in table 1:

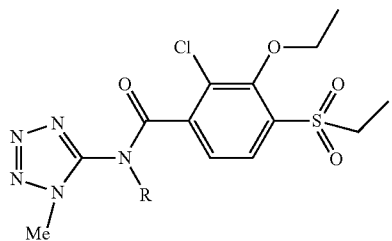

TABLE 14

Inventive compounds of the formula (I) in which Q is Q1, R⁶ is ethyl, X is chlorine, W is C—Y, Y is ethoxy, V is hydrogen and Z is methylsulfonyl, and R is as defined in table 1:

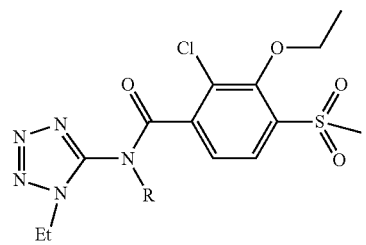

TABLE 15

Inventive compounds of the formula (I) in which Q is Q1, R⁶ is methyl, X is chlorine, W is C—Y, Y is allyloxy, V is hydrogen and Z is methylsulfonyl, and R is as defined in table 1:

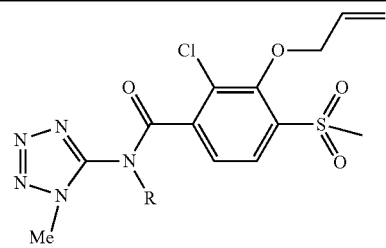

TABLE 16

Inventive compounds of the formula (I) in which Q is Q1, R⁶ is methyl, X is chlorine, W is C—Y, Y is 2-fluoroethoxy, V is hydrogen and Z is methylsulfonyl, and R is as defined in table 1:

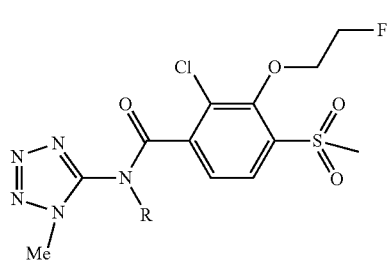

TABLE 17

Inventive compounds of the formula (I) in which Q is Q1, R⁶ is methyl, X is chlorine, W is C—Y, Y is propoxy, V is hydrogen and Z is ethylsulfonyl, and R is as defined in table 1:

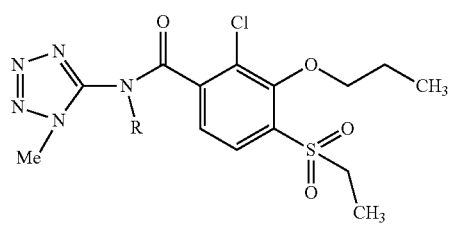

TABLE 18

Inventive compounds of the formula (I) in which Q is Q1, R⁶ is methyl, X is chlorine, W is C—Y, Y is propoxy, V is hydrogen and Z is methylsulfonyl, and R is as defined in table 1:

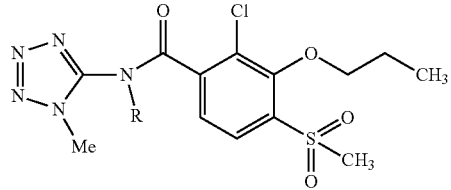

TABLE 19

Inventive compounds of the formula (I) in which Q is Q1, R⁶ is methyl, X is chlorine, W is C—Y, Y is (3-methylsulfanyl)propoxy, V is hydrogen and Z is chlorine, and R is as defined in table 1:

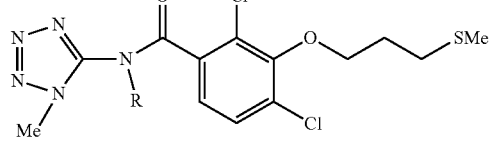

TABLE 20

Inventive compounds of the formula (I) in which Q is Q1, R⁶ is methyl, X is chlorine W is C—Y, Y is (2-methylsulfanyl) ethoxy, V is hydrogen and Z is chlorine, and R is as defined in table 1:

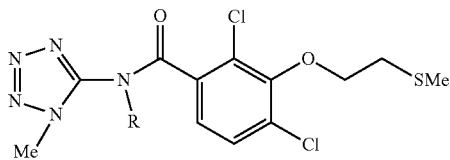

TABLE 21

Inventive compounds of the formula (I) in which Q is Q1, R⁶ is methyl, X is chlorine, W is C—Y, Y is cyclopropylmethoxy, V is hydrogen and Z is methylsulfonyl, and R is as defined in table 1:

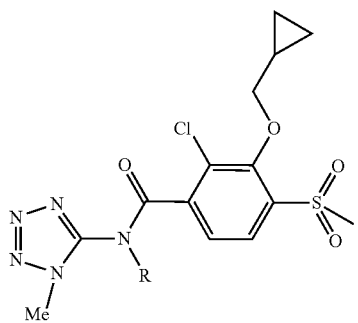

TABLE 22

Inventive compounds of the formula (I) in which Q is Q1, R⁶ is methyl, X is chlorine, W is C—Y, Y is cyclopropylmethoxy, V is hydrogen and Z is ethylsulfonyl, and R is as defined in table 1:

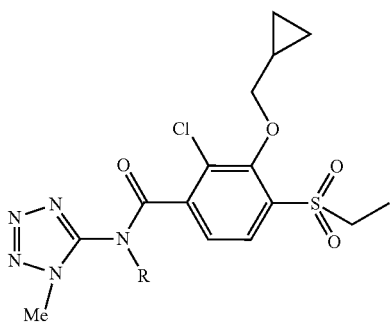

TABLE 23

Inventive compounds of the formula (I) in which Q is Q1, R⁶ is methyl, X is chlorine, W is C—Y, Y is (2-dimethylamino)-2-oxoethoxy, V is hydrogen and Z is bromine, and R is as defined in table 1:

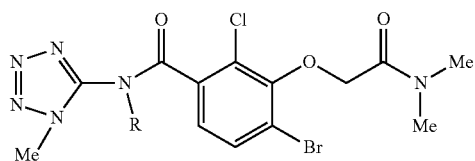

TABLE 24

Inventive compounds of the formula (I) in which Q is Q1, R⁶ is methyl, X is chlorine, W is C—Y, Y is methoxycarbonyl, V is hydrogen and Z is methylsulfonyl, and R is as defined in table 1:

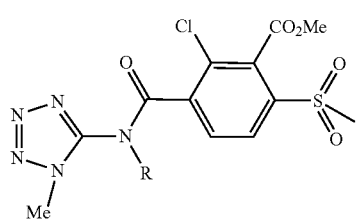

TABLE 25

Inventive compounds of the formula (I) in which Q is Q1, R⁶ is methyl, X is chlorine, W is C—Y, Y is (ethoxyimino)methyl, V is hydrogen and Z is methylsulfonyl, and R is as defined in table 1:

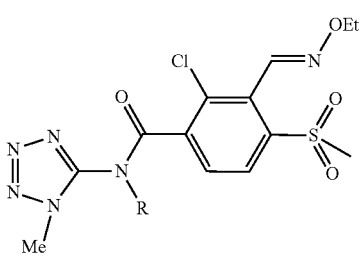

TABLE 26

Inventive compounds of the formula (I) in which Q is Q1, R⁶ is methyl, X is chlorine, W is C—Y, Y is 1-(ethylamino)-1-oxopropan-2-yl]amino, V is hydrogen and Z is chlorine, and R is as defined in table 1:

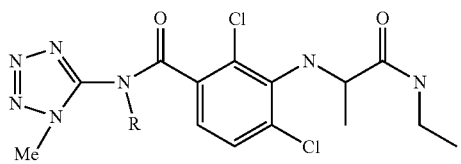

TABLE 27

Inventive compounds of the formula (I) in which Q is Q1, R⁶ is methyl, X is chlorine, W is C—Y, Y is methylsulfanyl, V is hydrogen and Z is chlorine, and R is as defined in table 1:

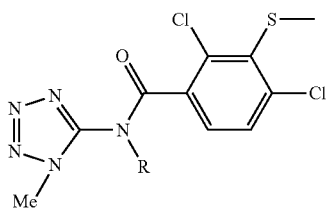

TABLE 28

Inventive compounds of the formula (I) in which Q is Q1, $R^6$ is methyl, X is chlorine, W is C—Y, Y is methylsulfanyl, V is hydrogen and Z is trifluoromethyl, and R is as defined in table 1:

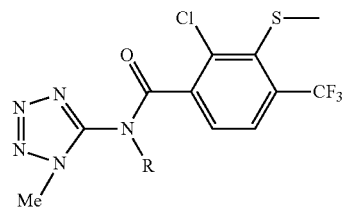

TABLE 29

Inventive compounds of the formula (I) in which Q is Q1, $R^6$ is ethyl, X is chlorine, W is C—Y, Y is methylsulfanyl, V is hydrogen and Z is chlorine, and R is as defined in table 1:

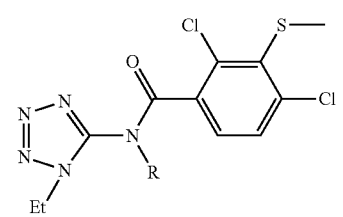

TABLE 30

Inventive compounds of the formula (I) in which Q is Q1, $R^6$ is methyl, X is chlorine, W is C—Y, Y is methylsulfinyl, V is hydrogen and Z is chlorine, and R is as defined in table 1:

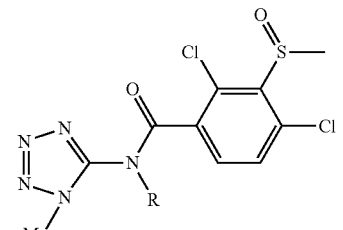

TABLE 31

Inventive compounds of the formula (I) in which Q is Q1, $R^6$ is ethyl, X is chlorine, W is C—Y, Y is methylsulfinyl, V is hydrogen and Z is chlorine, and R is as defined in table 1:

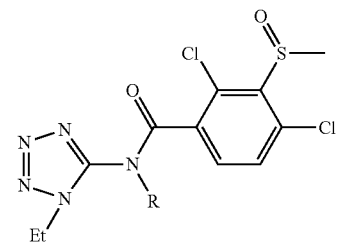

TABLE 32

Inventive compounds of the formula (I) in which Q is Q1, $R^6$ is methyl, X is chlorine, W is C—Y, Y is methylsulfinyl, V is hydrogen and Z is methyl, and R is as defined in table 1:

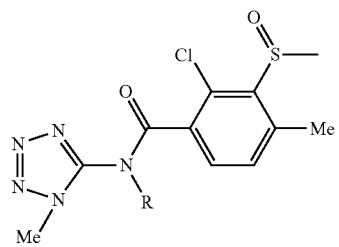

TABLE 33

Inventive compounds of the formula (I) in which Q is Q1, $R^6$ is methyl, X is chlorine, W is C—Y, Y is methylsulfanyl, V is hydrogen and Z is methyl, and R is as defined in table 1:

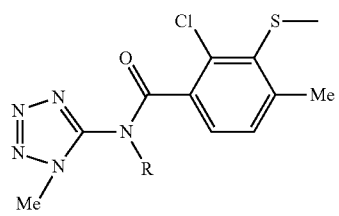

TABLE 34

Inventive compounds of the formula (I) in which Q is Q1, $R^6$ is methyl, X is chlorine, W is C—Y, Y is methylsulfonyl, V is hydrogen and Z is chlorine, and R is as defined in table 1:

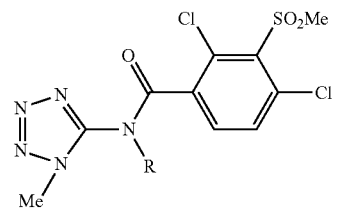

TABLE 35

Inventive compounds of the formula (I) in which Q is Q1, $R^6$ is ethyl, X is chlorine, W is C—Y, Y is methylsulfonyl, V is hydrogen and Z is chlorine, and R is as defined in table 1:

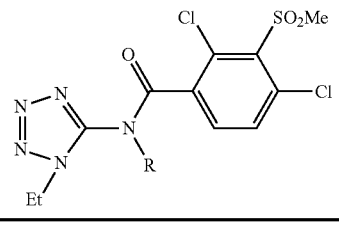

TABLE 36

Inventive compounds of the formula (I) in which Q is Q1, $R^6$ is methyl, X is chlorine, W is C—Y, Y is methylsulfonyl, V is hydrogen and Z is trifluoromethyl, and R is as defined in table 1:

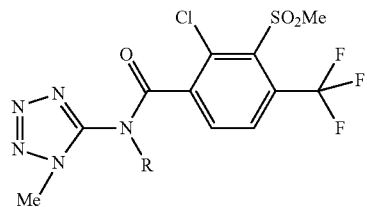

TABLE 37

Inventive compounds of the formula (I) in which Q is Q1, $R^6$ is ethyl, X is chlorine, W is C—Y, Y is methylsulfonyl, V is hydrogen and Z is trifluoromethyl, and R is as defined in table 1:

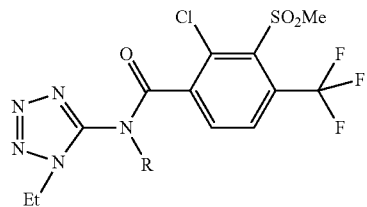

TABLE 38

Inventive compounds of the formula (I) in which Q is Q1, $R^6$ is methyl, X is chlorine, W is C—Y, Y is methylsulfonyl, V is hydrogen and Z is methylsulfonyl, and R is as defined in table 1:

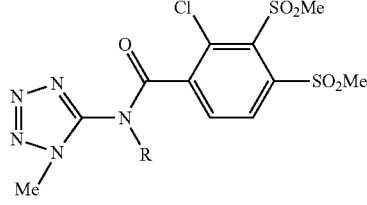

TABLE 39

Inventive compounds of the formula (I) in which Q is Q1, $R^6$ is ethyl, X is chlorine, W is C—Y, Y is methylsulfonyl, V is hydrogen and Z is methylsulfonyl, and R is as defined in table 1:

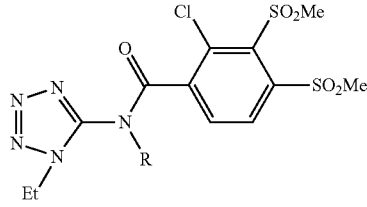

TABLE 40

Inventive compounds of the formula (I) in which Q is Q1, $R^6$ is methyl, X is chlorine, W is C—Y, Y is ethylsulfonyl, V is hydrogen and Z is chlorine, and R is as defined in table 1:

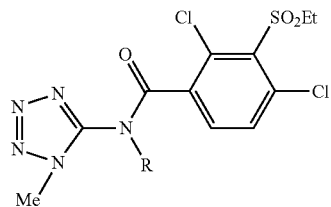

TABLE 41

Inventive compounds of the formula (I) in which Q is Q1, $R^6$ is methyl, X is chlorine, W is C—Y, Y is ethylsulfinyl, V is hydrogen and Z is chlorine, and R is as defined in table 1:

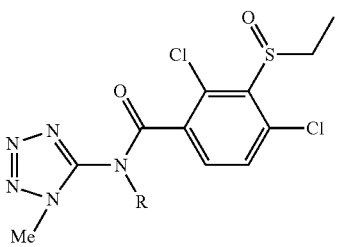

TABLE 42

Inventive compounds of the formula (I) in which Q is Q1, $R^6$ is methyl, X is chlorine, W is C—Y, Y is ethylsulfinyl, V is hydrogen and Z is methyl, and R is as defined in table 1:

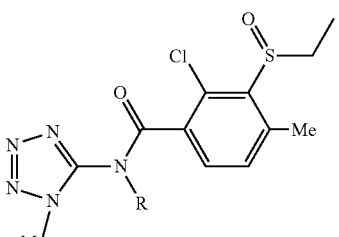

TABLE 43

Inventive compounds of the formula (I) in which Q is Q1, $R^6$ is methyl, X is chlorine, W is C—Y, Y is methylsulfonyl, V is hydrogen and Z is methyl, and R is as defined in table 1:

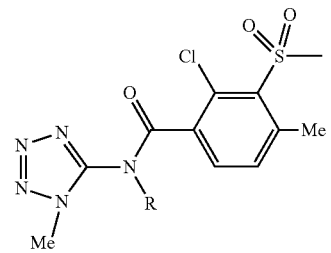

TABLE 44

Inventive compounds of the formula (I) in which Q is Q1,
$R^6$ is methyl, X is chlorine, W is C—Y, Y is ethylsulfanyl,
V is hydrogen and Z is methyl, and R is as defined in table 1:

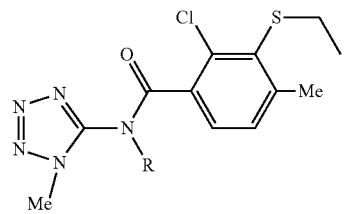

TABLE 45

Inventive compounds of the formula (I) in which Q is Q1, $R^6$ is methyl,
X is chlorine, W is C—Y, Y is ethylsulfonyl, V is hydrogen and
Z is methyl, and R is as defined in table 1:

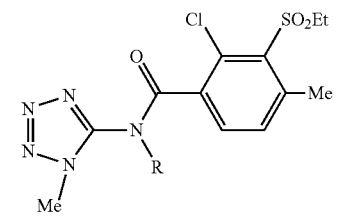

TABLE 46

Inventive compounds of the formula (I) in which Q is Q1,
$R^6$ is methyl, X is chlorine, W is C—Y, Y is 2-methoxyethylsulfinyl,
V is hydrogen and Z is chlorine, and R is as defined in table 1:

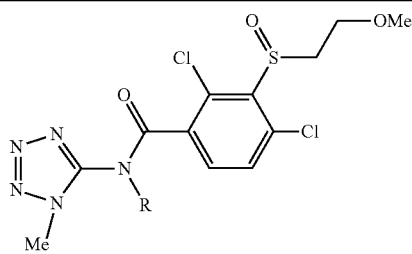

TABLE 47

Inventive compounds of the formula (I) in which Q is Q1,
$R^6$ is methyl, X is bromine, W is C—Y, Y is methylsulfanyl,
V is hydrogen and Z is methyl, and R is as defined in table 1:

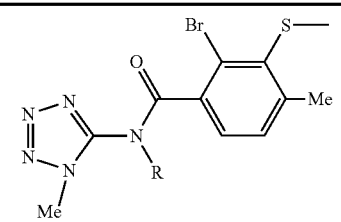

TABLE 48

Inventive compounds of the formula (I) in which Q is Q1,
$R^6$ is methyl, X is bromine, W is C—Y, Y is methylsulfinyl,
V is hydrogen and Z is methyl, and R is as defined in table 1:

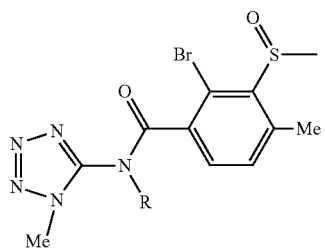

TABLE 49

Inventive compounds of the formula (I) in which Q is Q1,
$R^6$ is methyl, X is bromine, W is C—Y, Y is methylsulfonyl,
V is hydrogen and Z is methyl, and R is as defined in table 1:

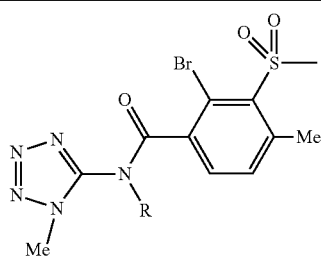

TABLE 50

Inventive compounds of the formula (I) in which Q is Q1,
$R^6$ is methyl, X is bromine, W is C—Y, Y is ethylsulfanyl,
V is hydrogen and Z is methyl, and R is as defined in table 1:

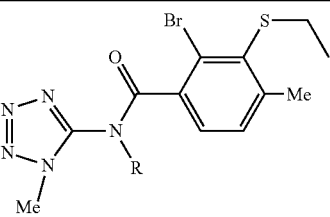

TABLE 51

Inventive compounds of the formula (I) in which Q is Q1,
$R^6$ is methyl, X is bromine, W is C—Y, Y is ethylsulfinyl,
V is hydrogen and Z is methyl, and R is as defined in table 1:

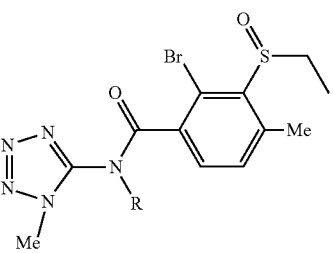

TABLE 52

Inventive compounds of the formula (I) in which Q is Q1, $R^6$ is methyl, X is bromine, W is C—Y, Y is ethylsulfonyl, V is hydrogen and Z is methyl, and R is as defined in table 1:

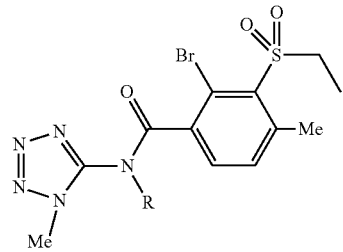

TABLE 53

Inventive compounds of the formula (I) in which Q is Q1, $R^6$ is methyl, X is methyl, W is C—Y, Y is 1H-pyrazol-1-yl, V is hydrogen and Z is methylsulfonyl, and R is as defined in table 1:

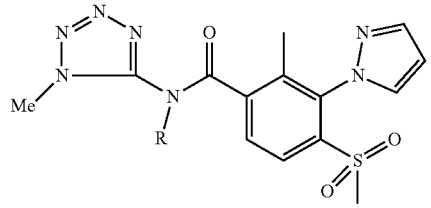

TABLE 54

Inventive compounds of the formula (I) in which Q is Q1, $R^6$ is ethyl, X is methyl, W is C—Y, Y is 1H-pyrazol-1-yl, V is hydrogen and Z is methylsulfonyl, and R is as defined in table 1:

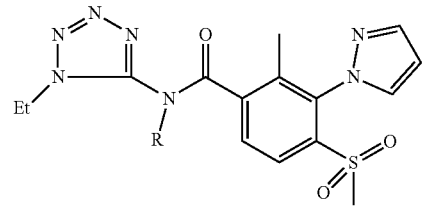

TABLE 55

Inventive compounds of the formula (I) in which Q is Q1, $R^6$ is methyl, X is methyl, W is C—Y, Y is 4,5-dihydro-1,2-oxazol-3-yl, V is hydrogen and Z is methylsulfonyl, and R is as defined in table 1:

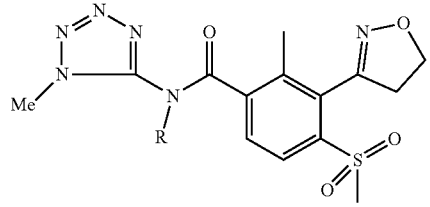

TABLE 56

Inventive compounds of the formula (I) in which Q is Q1, $R^6$ is ethyl, X is methyl, W is C—Y, Y is 4,5-dihydro-1,2-oxazol-3-yl, V is hydrogen and Z is methylsulfonyl, and R is as defined in table 1:

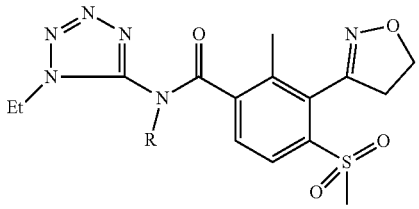

TABLE 57

Inventive compounds of the formula (I) in which Q is Q1, $R^6$ is methyl, X is methyl, W is C—Y, Y is (cyclopropylmethyl)amino, V is hydrogen and Z is methylsulfonyl, and R is as defined in table 1:

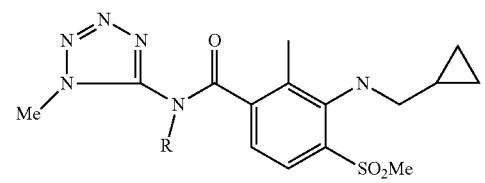

TABLE 58

Inventive compounds of the formula (I) in which Q is Q1, $R^6$ is methyl, X is methyl, W is C—Y, Y is propylamino, V is hydrogen and Z is methylsulfonyl, and R is as defined in table 1:

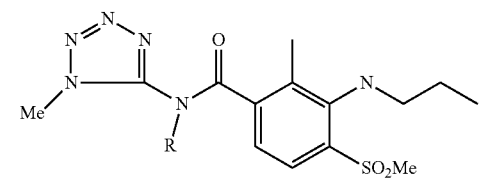

TABLE 59

Inventive compounds of the formula (I) in which Q is Q1, $R^6$ is methyl, X is methyl, W is C—Y, Y is methylsulfanyl, V is hydrogen and Z is methylsulfonyl, and R is as defined in table 1:

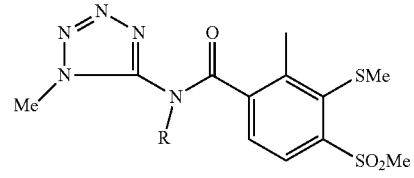

TABLE 60

Inventive compounds of the formula (I) in which Q is Q1, $R^6$ is methyl, X is methyl, W is C—Y, Y is methylsulfonyl, V is hydrogen and Z is methylsulfonyl, and R is as defined in table 1:

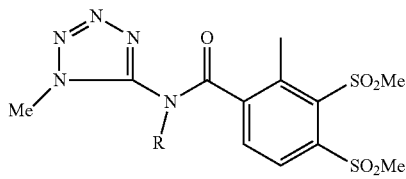

TABLE 61

Inventive compounds of the formula (I) in which Q is Q1, $R^6$ is ethyl, X is methyl, W is C—Y, Y is methylsulfonyl, V is hydrogen and Z is methylsulfonyl, and R is as defined in table 1:

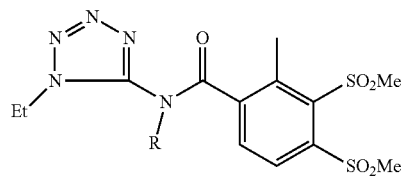

TABLE 62

Inventive compounds of the formula (I) in which Q is Q1, $R^6$ is methyl, X is methyl, W is C—Y, Y is ethylsulfonyl, V is hydrogen and Z is methylsulfonyl, and R is as defined in table 1:

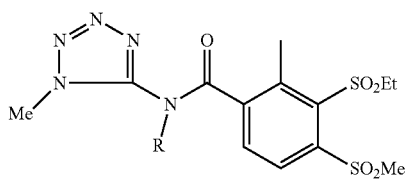

TABLE 63

Inventive compounds of the formula (I) in which Q is Q1, $R^6$ is methyl, X is methyl, W is C—Y, Y is methylsulfanyl, V is hydrogen and Z is trifluoromethyl, and R is as defined in table 1:

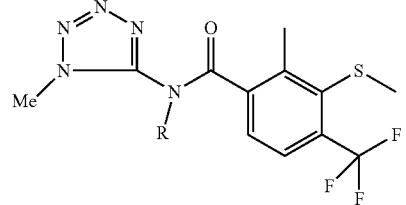

TABLE 64

Inventive compounds of the formula (I) in which Q is Q1, $R^6$ is ethyl, X is methyl, W is C—Y, Y is methylsulfanyl, V is hydrogen and Z is trifluoromethyl, and R is as defined in table 1:

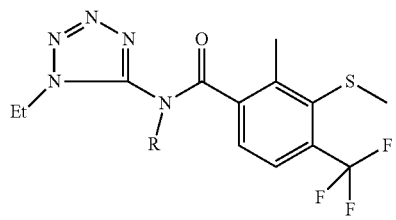

TABLE 65

Inventive compounds of the formula (I) in which Q is Q1, $R^6$ is methyl, X is methyl, W is C—Y, Y is methylsulfanyl, V is hydrogen and Z is chlorine, and R is as defined in table 1:

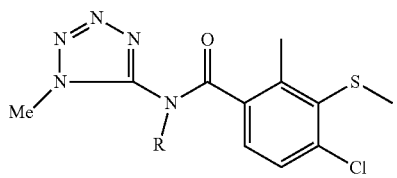

TABLE 66

Inventive compounds of the formula (I) in which Q is Q1, $R^6$ is ethyl, X is methyl, W is C—Y, Y is methylsulfanyl, V is hydrogen and Z is chlorine, and R is as defined in table 1:

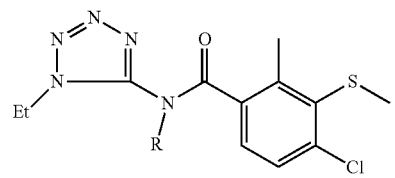

TABLE 67

Inventive compounds of the formula (I) in which Q is Q1, $R^6$ is methyl, X is methyl, W is C—Y, Y is methylsulfanyl, V is hydrogen and Z is bromine, and R is as defined in table 1:

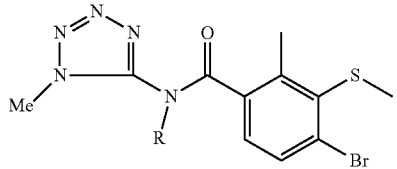

TABLE 68

Inventive compounds of the formula (I) in which Q is Q1, $R^6$ is methyl, X is methyl, W is C—Y, Y is methylsulfinyl, V is hydrogen and Z is bromine, and R is as defined in table 1:

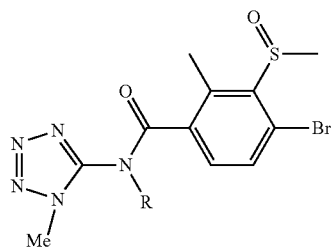

TABLE 69

Inventive compounds of the formula (I) in which Q is Q1, $R^6$ is methyl, X is methyl, W is C—Y, Y is ethylsulfinyl, V is hydrogen and Z is bromine, and R is as defined in table 1:

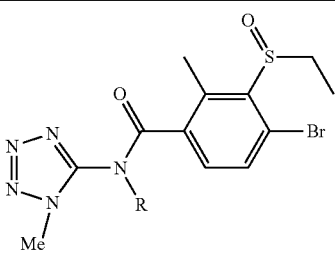

TABLE 70

Inventive compounds of the formula (I) in which Q is Q1, $R^6$ is methyl, X is methyl, W is C—Y, Y is ethylsulfonyl, V is hydrogen and Z is bromine, and R is as defined in table 1:

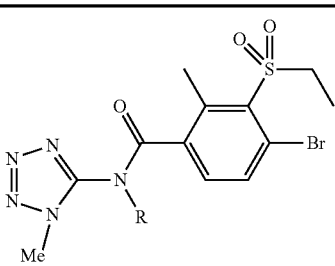

TABLE 71

Inventive compounds of the formula (I) in which Q is Q1, $R^6$ is methyl, X is methyl, W is C—Y, Y is methylsulfanyl, V is hydrogen and Z is iodine, and R is as defined in table 1:

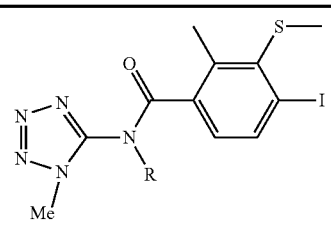

TABLE 72

Inventive compounds of the formula (I) in which Q is Q1, $R^6$ is methyl, X is methyl, W is C—Y, Y is methylsulfinyl, V is hydrogen and Z is iodine, and R is as defined in table 1:

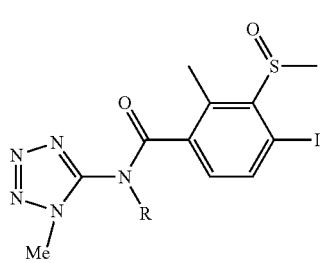

TABLE 73

Inventive compounds of the formula (I) in which Q is Q1, $R^6$ is methyl, X is methyl, W is C—Y, Y is methylsulfonyl, V is hydrogen and Z is iodine, and R is as defined in table 1:

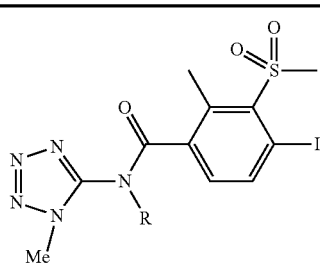

TABLE 74

Inventive compounds of the formula (I) in which Q is Q1, $R^6$ is methyl, X is methyl, W is C—Y, Y is ethylsulfanyl, V is hydrogen and Z is iodine, and R is as defined in table 1:

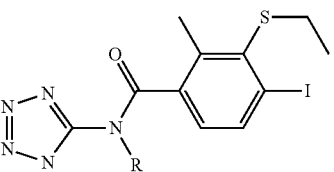

TABLE 75

Inventive compounds of the formula (I) in which Q is Q1, $R^6$ is ethyl, X is methyl, W is C—Y, Y is ethylsulfanyl, V is hydrogen and Z is iodine, and R is as defined in table 1:

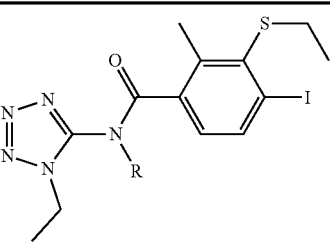

TABLE 76

Inventive compounds of the formula (I) in which Q is Q1, R⁶ is methyl, X is methyl, W is C—Y, Y is methylsulfinyl, V is hydrogen and Z is trifluoromethyl, and R is as defined in table 1:

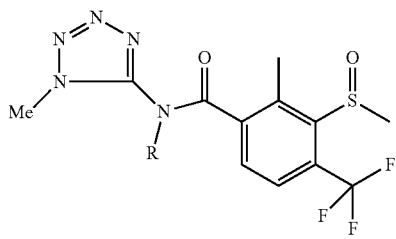

TABLE 77

Inventive compounds of the formula (I) in which Q is Q1, R⁶ is n-propyl, X is methyl, W is C—Y, Y is methylsulfinyl, V is hydrogen and Z is trifluoromethyl, and R is as defined in table 1:

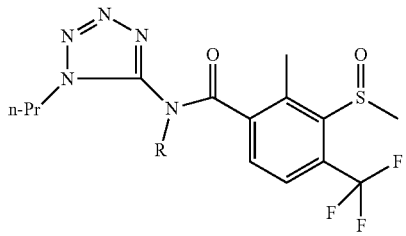

TABLE 78

Inventive compounds of the formula (I) in which Q is Q1, R⁶ is allyl, X is methyl, W is C—Y, Y is methylsulfinyl, V is hydrogen and Z is trifluoromethyl, and R is as defined in table 1:

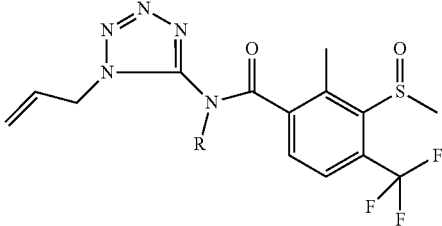

TABLE 79

Inventive compounds of the formula (I) in which Q is Q1, R⁶ is ethyl; X is methyl, W is C—Y, Y is methylsulfinyl, V is hydrogen and Z is chlorine, and R is as defined in table 1:

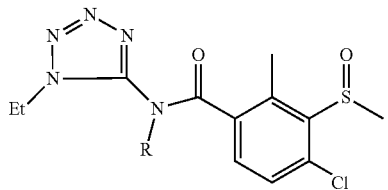

TABLE 80

Inventive compounds of the formula (I) in which Q is Q1, R⁶ is methyl, X is methyl, W is C—Y, Y is methylsulfonyl, V is hydrogen and Z is trifluoromethyl, and R is as defined in table 1:

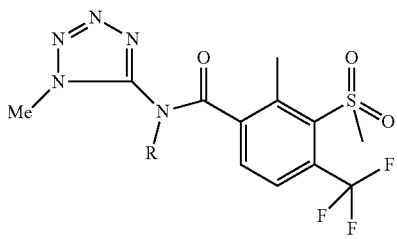

TABLE 81

Inventive compounds of the formula (I) in which Q is Q1, R⁶ is ethyl, X is methyl, W is C—Y, Y is methylsulfonyl, V is hydrogen and Z is trifluoromethyl, and R is as defined in table 1:

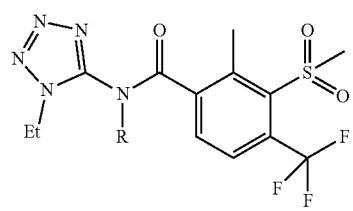

TABLE 82

Inventive compounds of the formula (I) in which Q is Q1, R⁶ is n-propyl, X is methyl, W is C—Y, Y is methylsulfonyl, V is hydrogen and Z is trifluoromethyl, and R is as defined in table 1:

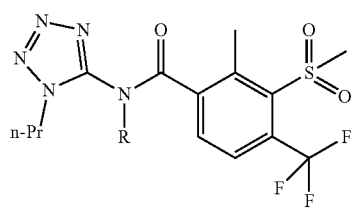

TABLE 83

Inventive compounds of the formula (I) in which Q is Q1, R⁶ is methoxymethyl; X is methyl, W is C—Y, Y is methylsulfonyl, V is hydrogen and Z is trifluoromethyl, and R is as defined in table 1:

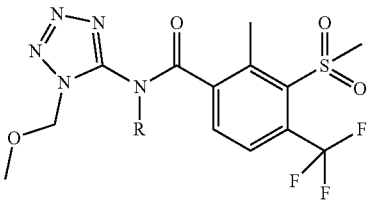

TABLE 84

Inventive compounds of the formula (I) in which Q is Q1, $R^6$ is allyl; X is methyl, W is C—Y, Y is methylsulfonyl, V is hydrogen and Z is trifluoromethyl, and R is as defined in table 1:

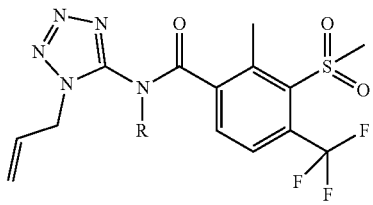

TABLE 85

Inventive compounds of the formula (I) in which Q is Q1, $R^6$ is propargyl, X is methyl, W is C—Y, Y is methylsulfonyl, V is hydrogen and Z is trifluoromethyl, and R is as defined in table 1:

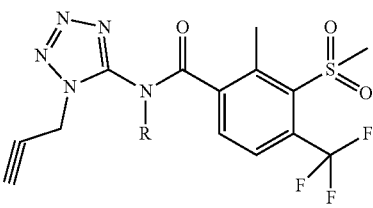

TABLE 86

Inventive compounds of the formula (I) in which Q is Q1, $R^6$ is ethyl, X is methyl, W is C—Y, Y is methylsulfonyl, V is hydrogen and Z is chlorine, and R is as defined in table 1:

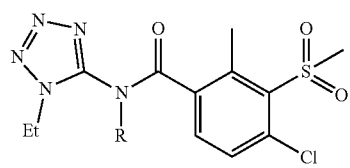

TABLE 87

Inventive compounds of the formula (I) in which Q is Q1, $R^6$ is methyl, X is methyl, W is C—Y, Y is methylsulfonyl, V is hydrogen and Z is bromine, and R is as defined in table 1:

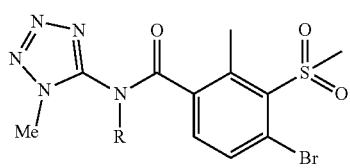

TABLE 88

Inventive compounds of the formula (I) in which Q is Q1, $R^6$ is methyl, X is methyl, W is C—Y, Y is ethylsulfanyl, V is hydrogen and Z is bromine, and R is as defined in table 1:

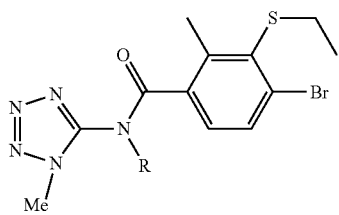

TABLE 89

Inventive compounds of the formula (I) in which Q is Q1, $R^6$ is methyl, X is methyl, W is C—Y, Y is ethylsulfanyl, V is hydrogen and Z is trifluoromethyl, and R is as defined in table 1:

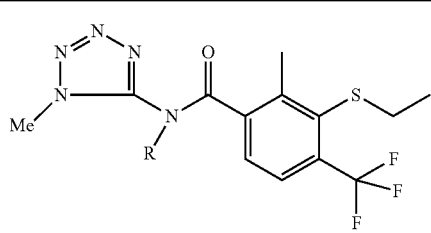

TABLE 90

Inventive compounds of the formula (I) in which Q is Q1, $R^6$ is methyl, X is methyl, W is C—Y, Y is ethylsulfanyl, V is hydrogen and Z is chlorine, and R is as defined in table 1:

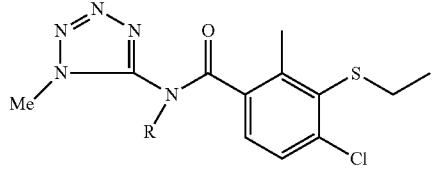

TABLE 91

Inventive compounds of the formula (I) in which Q is Q1, $R^6$ is ethyl, X is methyl, W is C—Y, Y is ethylsulfanyl, V is hydrogen and Z is trifluoromethyl, and R is as defined in table 1:

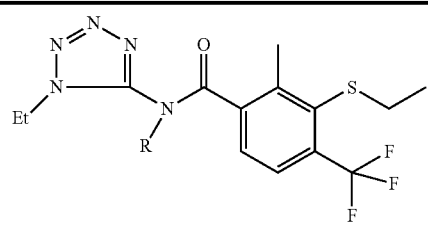

TABLE 92

Inventive compounds of the formula (I) in which Q is Q1, R⁶ is ethyl, X is methyl, W is C—Y, Y is ethylsulfinyl, V is hydrogen and Z is trifluoromethyl, and R is as defined in table 1:

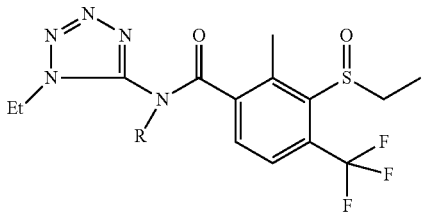

TABLE 93

Inventive compounds of the formula (I) in which Q is Q1, R⁶ is methyl, X is methyl, W is C—Y, Y is ethylsulfinyl, V is hydrogen and Z is chlorine, and R is as defined in table 1:

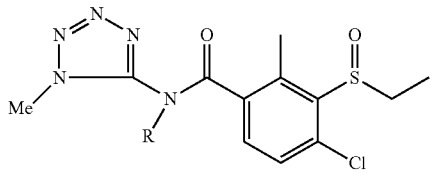

TABLE 94

Inventive compounds of the formula (I) in which Q is Q1, R⁶ is ethyl, X is methyl, W is C—Y, Y is ethylsulfonyl, V is hydrogen and Z is trifluoromethyl, and R is as defined in table 1:

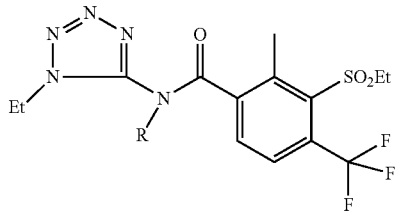

TABLE 95

Inventive compounds of the formula (I) in which Q is Q1, R⁶ is methyl, X is methyl, W is C—Y, Y is ethylsulfonyl, V is hydrogen and Z is chlorine, and R is as defined in table 1:

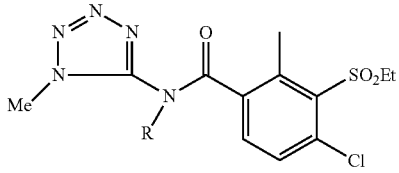

TABLE 96

Inventive compounds of the formula (I) in which Q is Q1, R⁶ is ethyl, X is methyl, W is C—Y, Y is ethylsulfonyl, V is hydrogen and Z is chlorine, and R is as defined in table 1:

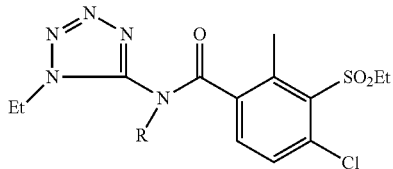

TABLE 97

Inventive compounds of the formula (I) in which Q is Q1, R⁶ is methyl, X is methyl, W is C—Y, Y is 2-methoxyethylsulfonyl, V is hydrogen and Z is methylsulfonyl, and R is as defined in table 1:

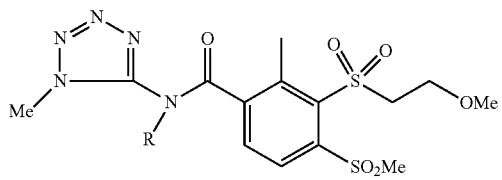

TABLE 98

Inventive compounds of the formula (I) in which Q is Q1, R⁶ is methyl, X is ethyl, W is C—Y, Y is methylsulfanyl, V is hydrogen and Z is trifluoromethyl, and R is as defined in table 1:

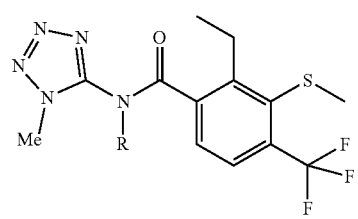

TABLE 99

Inventive compounds of the formula (I) in which Q is Q1, R⁶ is methyl, X is n-propyl, W is C—Y, Y is methylsulfanyl, V is hydrogen and Z is trifluoromethyl, and R is as defined in table 1:

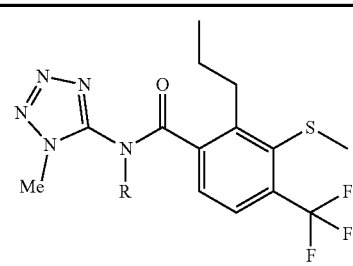

TABLE 100

Inventive compounds of the formula (I) in which Q is Q1, $R^6$ is ethyl, X is ethyl, W is C—Y, Y is methylsulfanyl, V is hydrogen and Z is trifluoromethyl, and R is as defined in table 1:

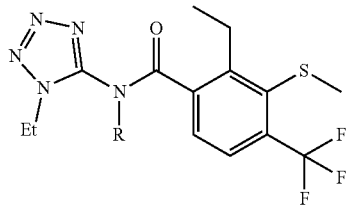

TABLE 101

Inventive compounds of the formula (I) in which Q is Q1, $R^6$ is methyl, X is ethyl, W is C—Y, Y is methylsulfanyl, V is hydrogen and Z is chlorine, and R is as defined in table 1:

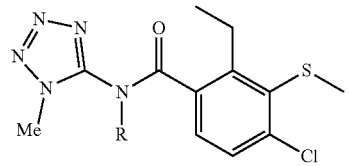

TABLE 102

Inventive compounds of the formula (I) in which Q is Q1, $R^6$ is ethyl, X is ethyl, W is C—Y, Y is methylsulfanyl, V is hydrogen and Z is bromine, and R is as defined in table 1:

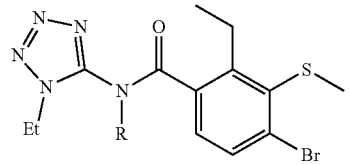

TABLE 103

Inventive compounds of the formula (I) in which Q is Q1, $R^6$ is methyl, X is ethyl, W is C—Y, Y is methylsulfinyl, V is hydrogen and Z is trifluoromethyl, and R is as defined in table 1:

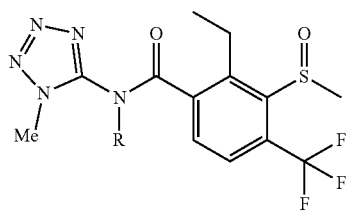

TABLE 104

Inventive compounds of the formula (I) in which Q is Q1, $R^6$ is ethyl, X is ethyl, W is C—Y, Y is methylsulfinyl, V is hydrogen and Z is trifluoromethyl, and R is as defined in table 1:

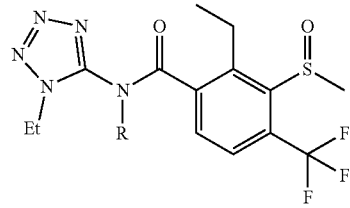

TABLE 105

Inventive compounds of the formula (I) in which Q is Q1, $R^6$ is methyl, X is n-propyl; W is C—Y, Y is methylsulfinyl, V is hydrogen and Z is trifluoromethyl, and R is as defined in table 1:

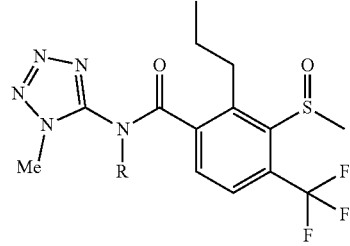

TABLE 106

Inventive compounds of the formula (I) in which Q is Q1, $R^6$ is methyl, X is ethyl, W is C—Y, Y is methylsulfinyl, V is hydrogen and Z is chlorine, and R is as defined in table 1:

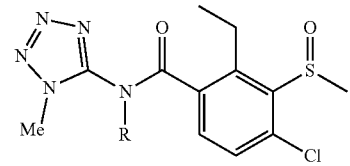

TABLE 107

Inventive compounds of the formula (I) in which Q is Q1, $R^6$ is ethyl, X is ethyl, W is C—Y, Y is methylsulfinyl, V is hydrogen and Z is chlorine, and R is as defined in table 1:

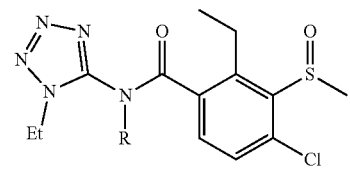

TABLE 108

Inventive compounds of the formula (I) in which
Q is Q1, $R^6$ is methyl, X is ethyl, W is C—Y, Y is methylsulfinyl,
V is hydrogen and Z is bromine, and R is as defined in table 1:

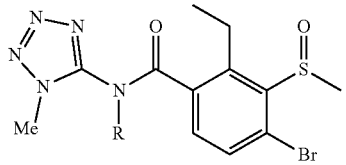

TABLE 109

Inventive compounds of the formula (I) in which
Q is Q1, $R^6$ is methyl, X is ethyl, W is C—Y, Y is ethylsulfinyl,
V is hydrogen and Z is trifluoromethyl, and R is as defined in table 1:

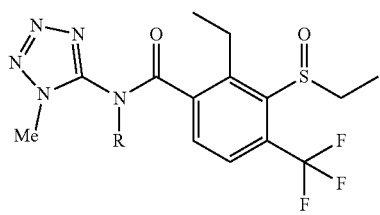

TABLE 110

Inventive compounds of the formula (I) in which
Q is Q1, $R^6$ is methyl, X is ethyl, W is C—Y, Y is methylsulfanyl,
V is hydrogen and Z is bromine, and R is as defined in table 1:

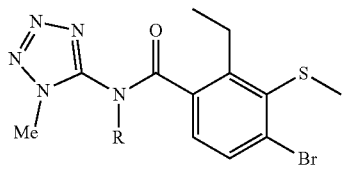

TABLE 111

Inventive compounds of the formula (I) in which Q is
Q1, $R^6$ is methyl, X is ethyl, W is C—Y, Y is methylsulfonyl,
V is hydrogen and Z is trifluoromethyl, and R is as defined in table 1:

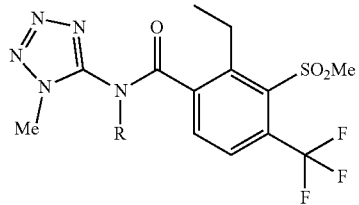

TABLE 112

Inventive compounds of the formula (I) in which Q is
Q1, $R^6$ is ethyl, X is ethyl, W is C—Y, Y is methylsulfonyl,
V is hydrogen and Z is trifluoromethyl, and R is as defined in table 1:

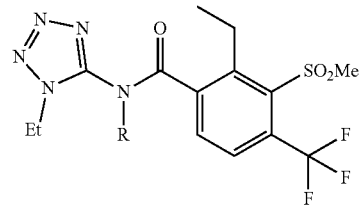

TABLE 113

Inventive compounds of the formula (I) in which Q is
Q1, $R^6$ is methyl, X is ethyl, W is C—Y, Y is methylsulfonyl,
V is hydrogen and Z is chlorine, and R is as defined in table 1:

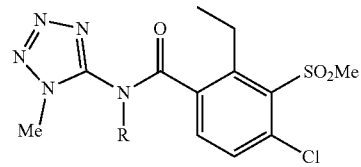

TABLE 114

Inventive compounds of the formula (I) in which Q is
Q1, $R^6$ is methyl, X is ethyl, W is C—Y, Y is methylsulfonyl,
V is hydrogen and Z is bromine, and R is as defined in table 1:

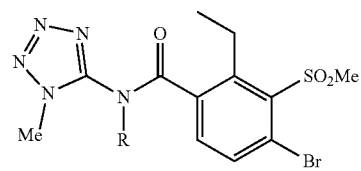

TABLE 115

Inventive compounds of the formula (I) in which Q is
Q1, $R^6$ is methyl, X is n-propyl; W is C—Y, Y is methylsulfinyl,
V is hydrogen and Z is trifluoromethyl, and R is as defined in table1:

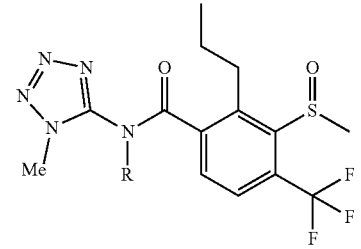

TABLE 116

Inventive compounds of the formula (I) in which Q is Q1, $R^6$ is methyl, X is Isopropyl; W is C—Y, Y is methylsulfanyl, V is hydrogen and Z is chlorine, and R is as defined in table 1:

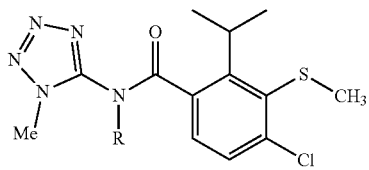

TABLE 117

Inventive compounds of the formula (I) in which Q is Q1, $R^6$ is methyl, X is cyclopropyl; W is C—Y, Y is methylsulfanyl, V is hydrogen and Z is trifluoromethyl, and R is as defined in table 1:

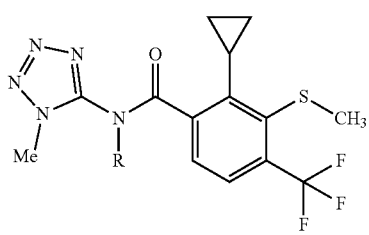

TABLE 118

Inventive compounds of the formula (I) in which Q is Q1, $R^6$ is methyl, X is methoxy; W is C—Y, Y is methylsulfanyl, V is hydrogen and Z is trifluoromethyl, and R is as defined in table 1:

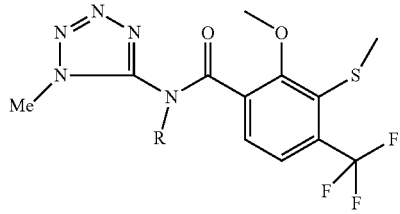

TABLE 119

Inventive compounds of the formula (I) in which Q is Q1, $R^6$ is methyl, X is methoxy; W is C—Y, Y is methylsulfinyl, V is hydrogen and Z is trifluoromethyl, and R is as defined in table 1:

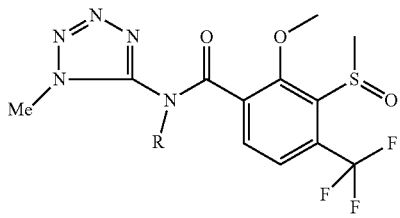

TABLE 120

Inventive compounds of the formula (I) in which Q is Q1, $R^6$ is methyl, X is methoxy; W is C—Y, Y is methylsulfonyl, V is hydrogen and Z is trifluoromethyl, and R is as defined in table 1:

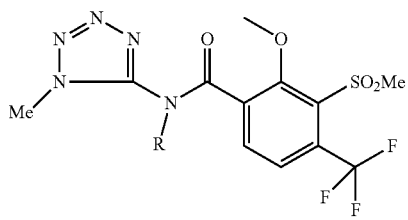

TABLE 121

Inventive compounds of the formula (I) in which Q is Q1, $R^6$ is methyl, X is methoxy; W is C—Y, Y is methylsulfanyl, V is hydrogen and Z is methylsulfonyl, and R is as defined in table 1:

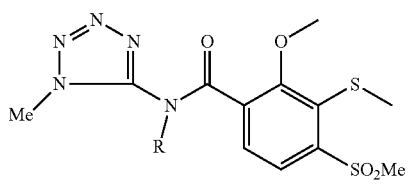

TABLE 122

Inventive compounds of the formula (I) in which Q is Q1, $R^6$ is methyl, X is methoxy; W is C—Y, Y is methylsulfinyl, V is hydrogen and Z is methylsulfonyl, and R is as defined in table 1:

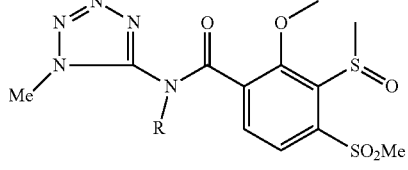

TABLE 123

Inventive compounds of the formula (I) in which Q is Q1, $R^6$ is methyl, X is methoxy; W is C—Y, Y is methylsulfonyl, V is hydrogen and Z is methylsulfonyl, and R is as defined in table 1:

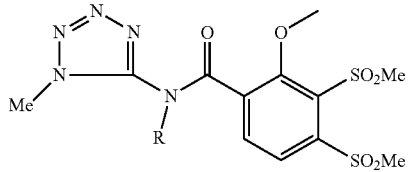

TABLE 124

Inventive compounds of the formula (I) in which Q is Q1, $R^6$ is methyl, X is methoxy; W is C—Y, Y is ethylsulfanyl, V is hydrogen and Z is trifluoromethyl, and R is as defined in table 1:

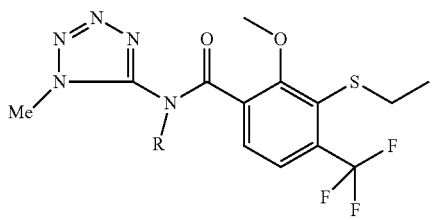

TABLE 125

Inventive compounds of the formula (I) in which Q is Q1, $R^6$ is ethyl, X is ethoxy; W is C—Y, Y is methylsulfanyl, V is hydrogen and Z is chlorine, and R is as defined in table 1:

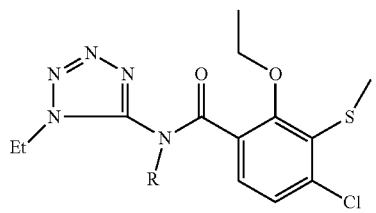

TABLE 126

Inventive compounds of the formula (I) in which Q is Q1, $R^6$ is methyl, X is methoxymethyl; W is C—Y, Y is methylsulfanyl, V is hydrogen and Z is methylsulfonyl, and R is as defined in table 1:

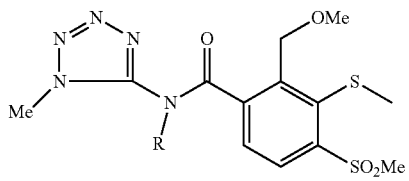

TABLE 127

Inventive compounds of the formula (I) in which Q is Q1, $R^6$ is methyl, X is methoxymethyl; W is C—Y, Y is methylsulfinyl, V is hydrogen and Z is methylsulfonyl, and R is as defined in table 1:

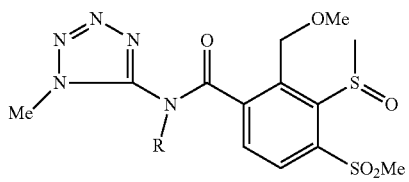

TABLE 128

Inventive compounds of the formula (I) in which Q is Q1, $R^6$ is methyl, X is methoxymethyl; W is C—Y, Y is methylsulfonyl, V is hydrogen and Z is methylsulfonyl, and R is as defined in table 1:

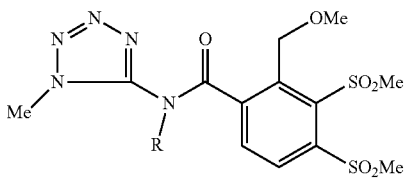

TABLE 129

Inventive compounds of the formula (I) in which Q is Q1, $R^6$ is methyl, X is chlorine; W is C—Y, Y is hydrogen, V is methyl and Z is methylsulfanyl, and R is as defined in table 1:

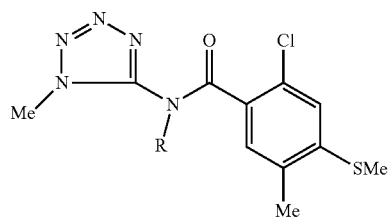

TABLE 130

Inventive compounds of the formula (I) in which Q is Q1, $R^6$ is methyl, X is chlorine; W is C—Y, Y is methylsulfinyl, V is methyl and Z is hydrogen, and R is as defined in table 1:

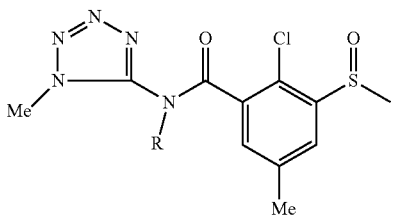

TABLE 131

Inventive compounds of the formula (I) in which Q is Q1, $R^6$ is methyl, X is chlorine; W is C—Y, Y is methylsulfonyl, V is methyl and Z is hydrogen, and R is as defined in table 1:

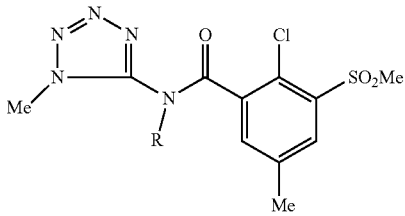

TABLE 132

Inventive compounds of the formula (I) in which Q is Q1, R⁶ is methyl, X is chlorine; W is C—Y, Y is, methyl; V is methyl and Z is methylsulfanyl, and R is as defined in table 1:

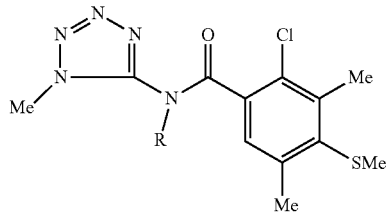

TABLE 133

Inventive compounds of the formula (I) in which Q is Q1, R⁶ is methyl, X is chlorine; W is C—Y, Y is hydrogen; V is hydrogen and Z is chlorine, and R is as defined in table 1:

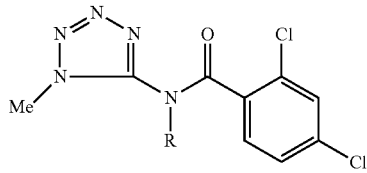

TABLE 134

Inventive compounds of the formula (I) in which Q is Q1, R⁶ is methyl, X is chlorine; W is C—Y, Y is hydrogen; V is hydrogen and Z is methylsulfanyl, and R is as defined in table 1:

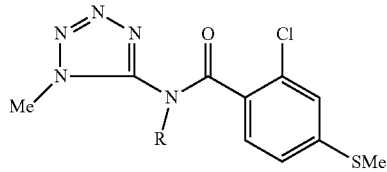

TABLE 135

Inventive compounds of the formula (I) in which Q is Q1, R⁶ is methyl, X is chlorine; W is C—Y, Y is hydrogen; V is hydrogen and Z is methylsulfonyl, and R is as defined in table 1:

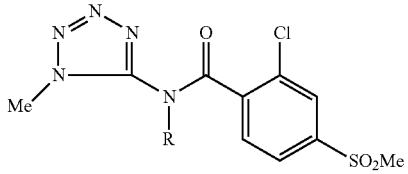

TABLE 136

Inventive compounds of the formula (I) in which Q is Q1, R⁶ is methyl, X is chlorine; W is C—Y, Y is hydrogen; V is hydrogen and Z is trifluoromethyl, and R is as defined in table 1:

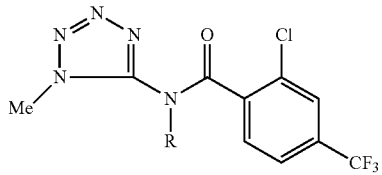

TABLE 137

Inventive compounds of the formula (I) in which Q is Q1, R⁶ is methyl, X is bromine; W is C—Y, Y is hydrogen; V is hydrogen and Z is methylsulfanyl, and R is as defined in table 1:

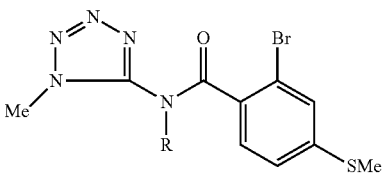

TABLE 138

Inventive compounds of the formula (I) in which Q is Q1, R⁶ is methyl, X is methylsulfonyl; W is C—Y, Y is hydrogen; V is hydrogen and Z is trifluoromethyl, and R is as defined in table 1:

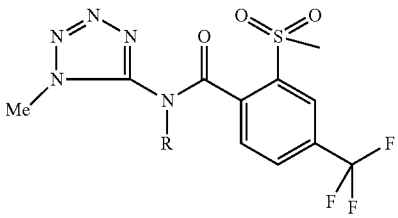

TABLE 139

Inventive compounds of the formula (I) in which Q is Q1, R⁶ is methyl, X is bromine; W is C—Y, Y is hydrogen; V is hydrogen and Z is trifluoromethyl, and R is as defined in table 1:

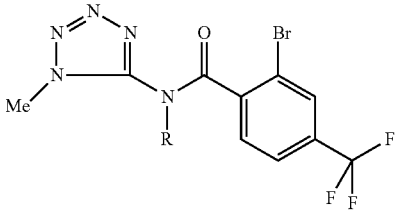

TABLE 140

Inventive compounds of the formula (I) in which Q is Q1, R⁶ is methyl, X is bromine; W is C—Y, Y is hydrogen; V is hydrogen and Z is methylsulfonyl, and R is as defined in table 1:

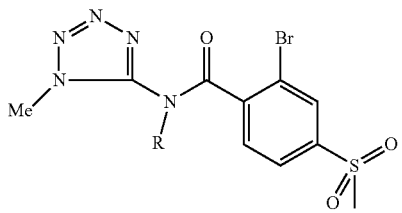

TABLE 141

Inventive compounds of the formula (I) in which Q is Q1, R⁶ is methyl, X is (methylsulfanyl)methyl; W is C—Y, Y is hydrogen; V is hydrogen and Z is trifluoromethyl, and R is as defined in table 1:

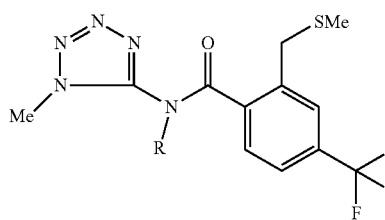

TABLE 142

Inventive compounds of the formula (I) in which Q is Q1, R⁶ is methyl, X is chlorine; W is N,V is hydrogen and Z is trifluoromethyl, and R is as defined in table 1:

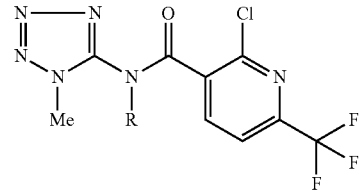

TABLE 143

Inventive compounds of the formula (I) in which Q is Q1, R⁶ is methyl, X is bromine; W is N,V is hydrogen and Z is trifluoromethyl, and R is as defined in table 1:

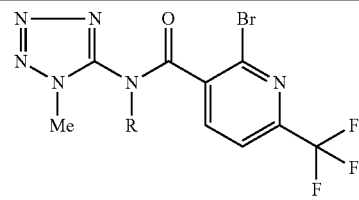

TABLE 144

Inventive compounds of the formula (I) in which Q is Q1, R⁶ is methyl, X is methyl; W is N;V is hydrogen and Z is trifluoromethyl, and R is as defined in table 1:

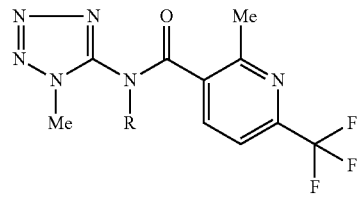

TABLE 145

Inventive compounds of the formula (I) in which Q is Q1, R⁶ is methyl, X is methylsulfonyl; W is N,; V is hydrogen and Z is trifluoromethyl, and R is as defined in table 1:

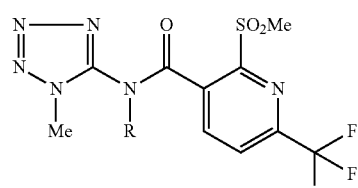

TABLE 146

Inventive compounds of the formula (I) in which Q is Q1, R⁶ is methyl, X is methoxymethyl; W is N,V is hydrogen and Z is trifluoromethyl, and R is as defined in table 1:

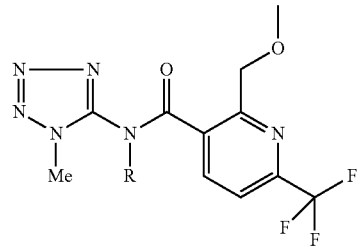

TABLE 147

Inventive compounds of the formula (I) in which Q is Q1, R⁶ is ethyl, X is methoxymethyl; W is N, V is hydrogen and Z is trifluoromethyl, and R is as defined in table 1:

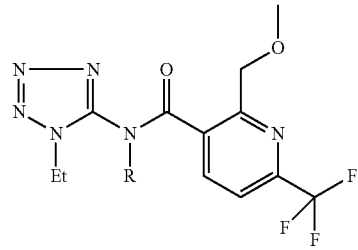

TABLE 148

Inventive compounds of the formula (I) in which Q is Q1, $R^6$ is ethyl, X is (2-methoxyethyl)methyl; W is N, V is hydrogen and Z is trifluoromethyl, and R is as defined in table 1:

TABLE 149

Inventive compounds of the formula (I) in which Q is Q1, $R^6$ is methyl, X is (3-methoxypropyloxy)methyl; W is N, V is hydrogen and Z is trifluoromethyl, and R is as defined in table 1:

TABLE 150

Inventive compounds of the formula (I) in which Q is Q1, $R^6$ is methyl, X is (cyclopropylmethoxy)methyl; W is N, V is hydrogen and Z is trifluoromethyl, and R is as defined in table 1:

TABLE 151

Inventive compounds of the formula (I) in which Q is Q1, $R^6$ is methyl, X is (methylsulfanyl)methyl; W is N, V is hydrogen and Z is trifluoromethyl, and R is as defined in table 1:

Q = Q2 triazoles

TABLE 152

Inventive compounds of the formula (I) in which Q is Q2, $R^7$ is methyl, X is nitro; W is C—Y, Y is hydrogen, V is hydrogen and Z is trifluoromethyl, and R is as defined in table 1:

TABLE 153

Inventive compounds of the formula (I) in which Q is Q2, $R^7$ is methyl, X is bromine; W is C—Y, Y is hydrogen, V is hydrogen and Z is trifluoromethyl, and R is as defined in table 1:

TABLE 154

Inventive compounds of the formula (I) in which Q is Q2, $R^7$ is methyl, X is methylsulfonyl; W is C—Y, Y is hydrogen, V is hydrogen and Z is trifluoromethyl, and R is as defined in table 1:

TABLE 155

Inventive compounds of the formula (I) in which Q is Q2, $R^7$ is methyl, X is chlorine; W is N, V is hydrogen and Z is trifluoromethyl, and R is as defined in table 1:

TABLE 156

Inventive compounds of the formula (I) in which Q is Q2, $R^7$ is methyl, X is methoxymethyl; W is N, V is hydrogen and Z is trifluoromethyl, and R is as defined in table 1:

TABLE 157

Inventive compounds of the formula (I) in which Q is Q2, R⁷ is methyl, X is (2-methoxyethoxy)methyl; W is N, V is hydrogen and Z is trifluoromethyl, and R is as defined in table 1:

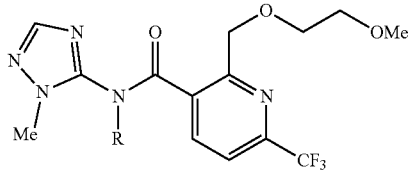

TABLE 158

Inventive compounds of the formula (I) in which Q is Q2, R⁷ is methyl, X is chlorine; W is C—Y, Y is (2,2,2-trifluoroethoxy)methyl, V is hydrogen and Z is methylsulfonyl, and R is as defined in table 1:

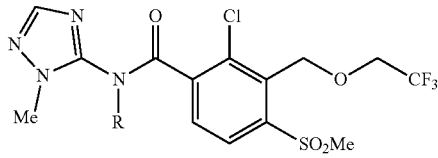

TABLE 159

Inventive compounds of the formula (I) in which Q is Q2, R⁷ is methyl, X is chlorine; W is C—Y, Y is 5-cyanomethyl-4,5-dihydro-1,2-oxazol-3-yl, V is hydrogen and Z is ethylsulfonyl, and R is as defined in table 1:

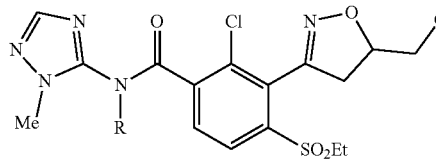

TABLE 160

Inventive compounds of the formula (I) in which Q is Q2, R⁷ is methyl, X is chlorine; W is C—Y, Y is 4,5-dihydro-1,2-oxazol-3-yl, V is hydrogen and Z is methylsulfonyl, and R is as defined in table 1:

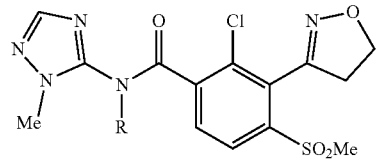

TABLE 161

Inventive compounds of the formula (I) in which Q is Q2, R⁷ is methyl, X is chlorine; W is C—Y, Y is 5-(methoxymethyl)-4,5-dihydro-1,2-oxazol-3-yl, V is hydrogen and Z is ethylsulfonyl, and R is as defined in table 1:

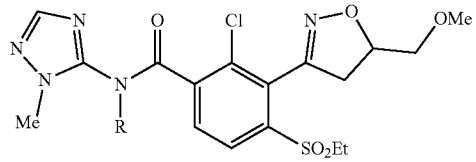

TABLE 162

Inventive compounds of the formula (I) in which Q is Q2, R⁷ is methyl, X is chlorine; W is C—Y, Y is methylsulfanyl, V is hydrogen and Z is methyl, and R is as defined in table 1:

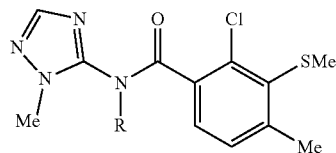

TABLE 163

Inventive compounds of the formula (I) in which Q is Q2, R⁷ is methyl, X is chlorine; W is C—Y, Y is methylsulfanyl, V is hydrogen and Z is chlorine, and R is as defined in table 1:

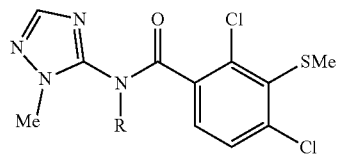

TABLE 164

Inventive compounds of the formula (I) in which Q is Q2, R⁷ is methyl, X is chlorine; W is C—Y, Y is methylsulfinyl, V is hydrogen and Z is chlorine, and R is as defined in table 1:

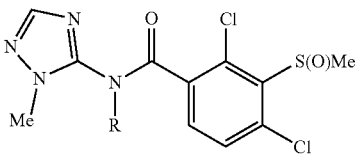

TABLE 165

Inventive compounds of the formula (I) in which Q is Q2, R⁷ is methyl, X is chlorine; W is C—Y, Y is methylsulfonyl, V is hydrogen and Z is chlorine, and R is as defined in table 1:

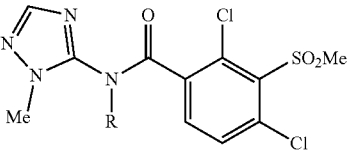

TABLE 166

Inventive compounds of the formula (I) in which Q is Q2, R⁷ is methyl, X is chlorine; W is C—Y, Y is methylsulfanyl, V is hydrogen and Z is methylsulfonyl, and R is as defined in table 1:

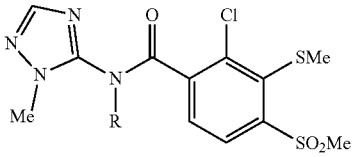

TABLE 167

Inventive compounds of the formula (I) in which Q is Q2, R⁷ is methyl, X is chlorine; W is C—Y, Y is methylsulfinyl, V is hydrogen and Z is methylsulfonyl, and R is as defined in table 1:

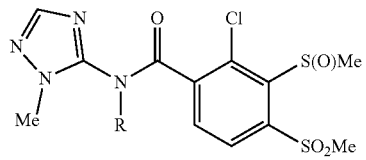

TABLE 168

Inventive compounds of the formula (I) in which Q is Q2, R⁷ is methyl, X is chlorine; W is C—Y, Y is methylsulfonyl, V is hydrogen and Z is methylsulfonyl, and R is as defined in table 1:

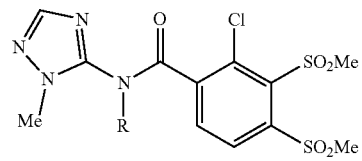

TABLE 169

Inventive compounds of the formula (I) in which Q is Q2, R⁷ is methyl, X is chlorine; W is C—Y, Y is methylsulfanyl, V is hydrogen and Z is trifluoromethyl, and R is as defined in table 1:

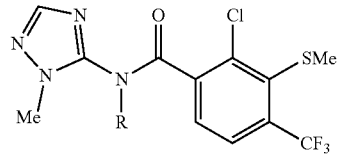

TABLE 170

Inventive compounds of the formula (I) in which Q is Q2, R⁷ is methyl, X is chlorine; W is C—Y, Y is methylsulfinyl, V is hydrogen and Z is trifluoromethyl, and R is as defined in table 1:

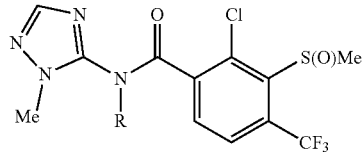

TABLE 171

Inventive compounds of the formula (I) in which Q is Q2, R⁷ is methyl, X is chlorine; W is C—Y, Y is methylsulfonyl, V is hydrogen and Z is trifluoromethyl, and R is as defined in table 1:

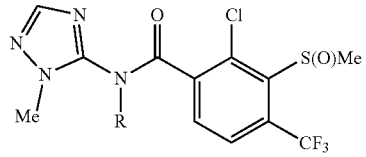

TABLE 172

Inventive compounds of the formula (I) in which Q is Q2, R⁷ is methyl, X is chlorine; W is C—Y, Y is 2-methoxy, V is hydrogen and Z is methylsulfonyl, and R is as defined in table 1:

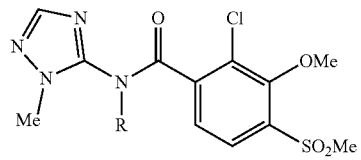

TABLE 173

Inventive compounds of the formula (I) in which Q is Q2, R⁷ is methyl, X is chlorine; W is C—Y, Y is propoxy, V is hydrogen and Z is methylsulfonyl, and R is as defined in table 1:

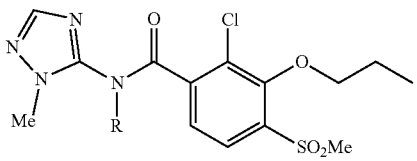

TABLE 174

Inventive compounds of the formula (I) in which Q is Q2, R⁷ is methyl, X is chlorine; W is C—Y, Y is cyclopropylmethoxy, V is hydrogen and Z is methylsulfonyl, and R is as defined in table 1:

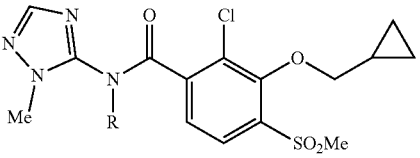

TABLE 175

Inventive compounds of the formula (I) in which Q is Q2, R⁷ is methyl, X is chlorine; W is C—Y, Y is 2-methoxyethoxy, V is hydrogen and Z is methylsulfonyl, and R is as defined in table 1:

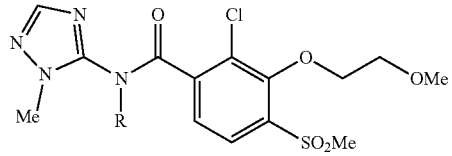

TABLE 176

Inventive compounds of the formula (I) in which Q is Q2, R⁷ is methyl, X is chlorine; W is C—Y, Y is methoxymethyl, V is hydrogen and Z is methylsulfonyl, and R is as defined in table 1:

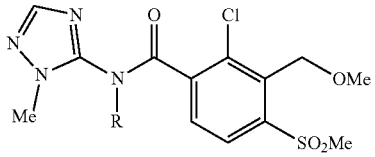

TABLE 177

Inventive compounds of the formula (I) in which Q is Q2, R⁷ is methyl, X is chlorine; W is C—Y, Y is (2-methoxyethoxy)methyl, V is hydrogen and Z is methylsulfonyl, and R is as defined in table 1:

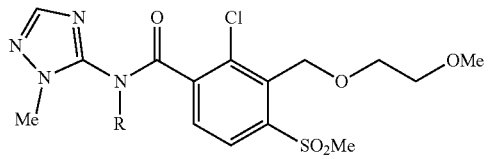

TABLE 178

Inventive compounds of the formula (I) in which Q is Q2, R⁷ is methyl, X is chlorine; W is C—Y, Y is chlorine, V is hydrogen and Z is methylsulfonyl, and R is as defined in table 1:

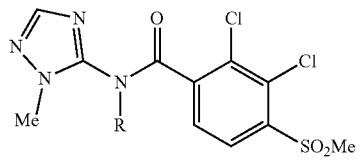

TABLE 179

Inventive compounds of the formula (I) in which Q is Q2, R⁷ is methyl, X is chlorine; W is C—Y, Y is (tetrahydrofuran-2-ylmethoxy)methyl, V is hydrogen and Z is methylsulfonyl, and R is as defined in table 1:

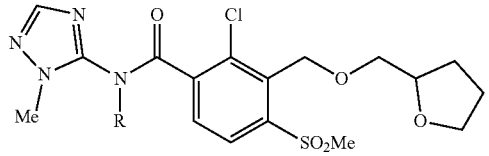

TABLE 180

Inventive compounds of the formula (I) in which Q is Q2, R⁷ is methyl, X is chlorine; W is C—Y, Y is 2-fluoroethoxy, V is hydrogen and Z is methylsulfonyl, and R is as defined in table 1:

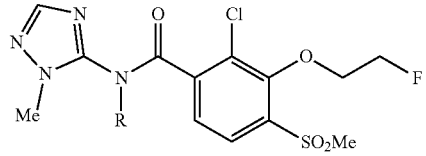

TABLE 181

Inventive compounds of the formula (I) in which Q is Q2, R⁷ is methyl, X is chlorine; W is C—Y, Y is (3-methoxy)propoxy, V is hydrogen and Z is ethylsulfonyl, and R is as defined in table 1:

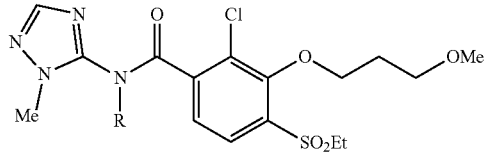

TABLE 182

Inventive compounds of the formula (I) in which Q is Q2, R⁷ is methyl, X is bromine; W is C—Y, Y is methylsulfanyl, V is hydrogen and Z is methyl, and R is as defined in table 1:

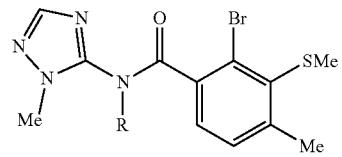

TABLE 183

Inventive compounds of the formula (I) in which Q is Q2, R⁷ is methyl, X is bromine; W is C—Y, Y is methylsulfinyl, V is hydrogen and Z is methyl, and R is as defined in table 1:

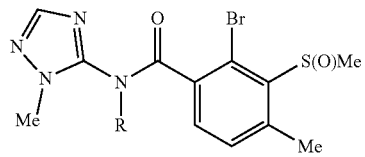

TABLE 184

Inventive compounds of the formula (I) in which Q is Q2, R⁷ is methyl, X is bromine; W is C—Y, Y is methylsulfonyl, V is hydrogen and Z is methyl, and R is as defined in table 1:

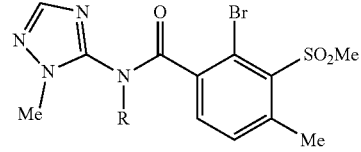

TABLE 185

Inventive compounds of the formula (I) in which Q is Q2, R⁷ is methyl, X is methyl; W is C—Y, Y is 4,5-dihydro-1,2-oxazol-3-yl, V is hydrogen and Z is methylsulfonyl, and R is as defined in table 1:

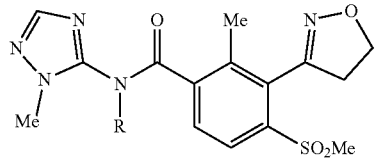

TABLE 186

Inventive compounds of the formula (I) in which Q is Q2, R⁷ is methyl, X is methyl; W is C—Y, Y is 1H-pyrazol-1-yl, V is hydrogen and Z is trifluoromethyl, and R is as defined in table 1:

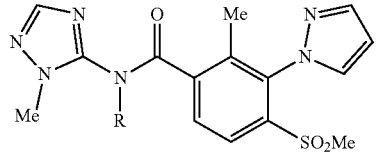

TABLE 187

Inventive compounds of the formula (I) in which Q is Q2, $R^7$ is methyl, X is methyl; W is C—Y, Y is methylsulfanyl, V is hydrogen and Z is trifluoromethyl, and R is as defined in table 1:

TABLE 188

Inventive compounds of the formula (I) in which Q is Q2, $R^7$ is methyl, X is methyl; W is C—Y, Y is methylsulfinyl, V is hydrogen and Z is trifluoromethyl, and R is as defined in table 1:

TABLE 189

Inventive compounds of the formula (I) in which Q is Q2, $R^7$ is methyl, X is methyl; W is C—Y, Y is methylsulfonyl, V is hydrogen and Z is trifluoromethyl, and R is as defined in table 1:

TABLE 190

Inventive compounds of the formula (I) in which Q is Q2, $R^7$ is methyl, X is methyl; W is C—Y, Y is methylsulfanyl, V is hydrogen and Z is methylsulfonyl, and R is as defined in table 1:

TABLE 191

Inventive compounds of the formula (I) in which Q is Q2, $R^7$ is methyl, X is methyl; W is C—Y, Y is methylsulfinyl, V is hydrogen and Z is methylsulfonyl, and R is as defined in table 1:

TABLE 192

Inventive compounds of the formula (I) in which Q is Q2, $R^7$ is methyl, X is methyl; W is C—Y, Y is methylsulfonyl, V is hydrogen and Z is methylsulfonyl, and R is as defined in table 1:

TABLE 193

Inventive compounds of the formula (I) in which Q is Q2, $R^7$ is methyl, X is methyl; W is C—Y, Y is ethylsulfonyl, V is hydrogen and Z is methylsulfonyl, and R is as defined in table 1:

TABLE 194

Inventive compounds of the formula (I) in which Q is Q2, $R^7$ is methyl, X is methoxy; W is C—Y, Y is methylsulfanyl, V is hydrogen and Z is methylsulfonyl, and R is as defined in table 1:

TABLE 195

Inventive compounds of the formula (I) in which Q is Q2, $R^7$ is methyl, X is methoxy; W is C—Y, Y is methylsulfinyl, V is hydrogen and Z is methylsulfonyl, and R is as defined in table 1:

TABLE 196

Inventive compounds of the formula (I) in which Q is Q2, $R^7$ is methyl, X is methoxy; W is C—Y, Y is methylsulfonyl, V is hydrogen and Z is methylsulfonyl, and R is as defined in table 1:

TABLE 197

Inventive compounds of the formula (I) in which Q is Q2, $R^7$ is methyl, X is methoxy; W is C—Y, Y is methylsulfanyl, V is hydrogen and Z is trifluoromethyl, and R is as defined in table 1:

TABLE 198

Inventive compounds of the formula (I) in which Q is Q2, $R^7$ is methyl, X is methoxy; W is C—Y, Y is methylsulfinyl, V is hydrogen and Z is trifluoromethyl, and R is as defined in table 1:

TABLE 199

Inventive compounds of the formula (I) in which Q is Q2, R7 is methyl, X is methoxy; W is C—Y, Y is methylsulfonyl, V is hydrogen and Z is trifluoromethyl, and R is as defined in table 1:

TABLE 200

Inventive compounds of the formula (I) in which Q is Q2, $R^7$ is methyl, X is methoxymethyl; W is C—Y, Y is methylsulfanyl, V is hydrogen and Z is methylsulfonyl, and R is as defined in table 1:

TABLE 201

Inventive compounds of the formula (I) in which Q is Q2, $R^7$ is methyl, X is methoxymethyl; W is C—Y, Y is methylsulfinyl, V is hydrogen and Z is methylsulfonyl, and R is as defined in table 1:

TABLE 202

Inventive compounds of the formula (I) in which Q is Q2, $R^7$ is methyl, X is methoxymethyl; W is C—Y, Y is methylsulfonyl, V is hydrogen and Z is methylsulfonyl, and R is as defined in table 1:

TABLE 203

Inventive compounds of the formula (I) in which Q is Q2, $R^7$ is methyl, X is ethyl; W is C—Y, Y is methylsulfanyl, V is hydrogen and Z is trifluoromethyl, and R is as defined in table 1:

TABLE 204

Inventive compounds of the formula (I) in which Q is Q2, $R^7$ is methyl, X is trifluoromethyl; W is C—Y, Y is 2-methoxyethoxy, V is hydrogen and Z is methylsulfonyl and R is as defined in table 1:

TABLE 205

Inventive compounds of the formula (I) in which Q is Q3, $R^8$ is methyl, X is chlorine; W is N, V is hydrogen and Z is trifluoromethyl, and R is as defined in table 1:

TABLE 206

Inventive compounds of the formula (I) in which Q is Q3, $R^8$ is methyl, X is methyl; W is N, V is hydrogen and Z is trifluoromethyl, and R is as defined in table 1:

TABLE 207

Inventive compounds of the formula (I) in which Q is Q3, R⁸ is methyl, X is methoxymethyl; W is N, V is hydrogen and Z is trifluoromethyl, and R is as defined in table 1:

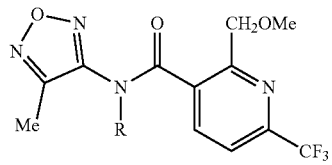

TABLE 208

Inventive compounds of the formula (I) in which Q is Q3, R⁸ is methyl, X is chlorine; W is C—Y, Y is (2,2,2-trifluoroethoxy)methyl, V is hydrogen and Z is methylsulfonyl, and R is as defined in table 1:

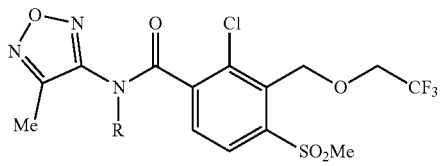

TABLE 209

Inventive compounds of the formula (I) in which Q is Q3, R⁸ is methyl, X is chlorine; W is C—Y, Y is 1H-1,2,3-triazol-1-yl, V is hydrogen and Z is methylsulfonyl, and R is as defined in table 1:

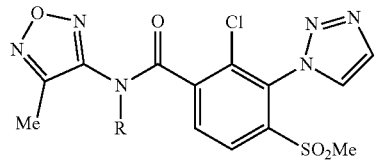

TABLE 210

Inventive compounds of the formula (I) in which Q is Q3, R⁸ is methyl, X is chlorine; W is C—Y, Y is 1H-pyrazol-1-yl, V is hydrogen and Z is methylsulfonyl, and R is as defined in table 1:

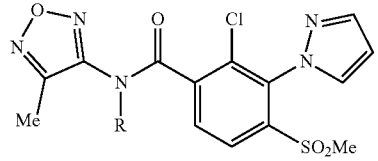

TABLE 211

Inventive compounds of the formula (I) in which Q is Q3, R⁸ is chlorine, X is chlorine; W is C—Y, Y is 1H-pyrazol-1-yl, V is hydrogen and Z is methylsulfonyl, and R is as defined in table 1:

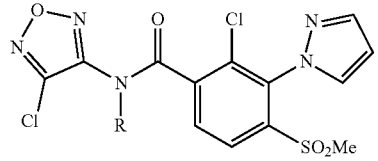

TABLE 212

Inventive compounds of the formula (I) in which Q is Q3, R⁸ is chlorine, X is chlorine; W is C—Y, Y is 4-methyl-1H-pyrazol-1-yl, V is hydrogen and Z is methylsulfonyl, and R is as defined in table 1:

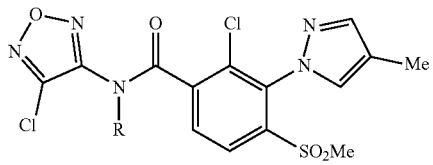

TABLE 213

Inventive compounds of the formula (I) in which Q is Q3, R⁸ is ethyl, X is chlorine, W is C—Y, Y is 1H-pyrazol-1-yl, V is hydrogen and Z is methylsulfonyl, and R is as defined in table 1:

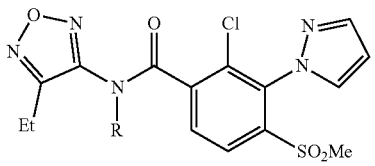

TABLE 214

Inventive compounds of the formula (I) in which Q is Q3, R⁸ is chlorine, X is chlorine; W is C—Y, Y is methylsulfanyl, V is hydrogen and Z is trifluoromethyl, and R is as defined in table 1:

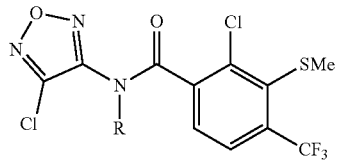

TABLE 215

Inventive compounds of the formula (I) in which Q is Q3, R⁸ is methyl, X is chlorine; W is C—Y, Y is methylsulfanyl, V is hydrogen and Z is trifluoromethyl, and R is as defined in table 1:

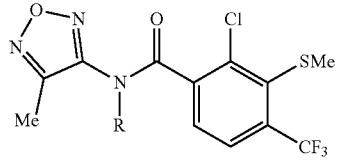

TABLE 216

Inventive compounds of the formula (I) in which Q is Q3, R⁸ is methyl, X is chlorine; W is C—Y, Y is methylsulfinyl, V is hydrogen and Z is trifluoromethyl, and R is as defined in table 1:

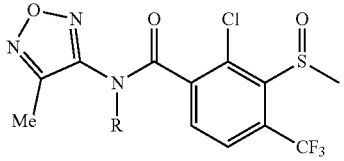

TABLE 217

Inventive compounds of the formula (I) in which Q is Q3, R⁸ is chlorine, X is chlorine; W is C—Y, Y is methylsulfinyl, V is hydrogen and Z is trifluoromethyl, and R is as defined in table 1:

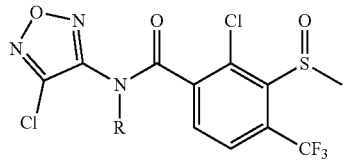

TABLE 218

Inventive compounds of the formula (I) in which Q is Q3, R⁸ is methyl, X is chlorine; W is C—Y, Y is methylsulfonyl, V is hydrogen and Z is trifluoromethyl, and R is as defined in table 1:

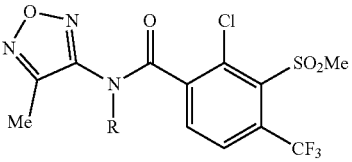

TABLE 219

Inventive compounds of the formula (I) in which Q is Q3, R⁸ is chlorine, X is chlorine; W is C—Y, Y is methylsulfonyl, V is hydrogen and Z is trifluoromethyl, and R is as defined in table 1:

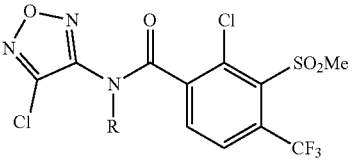

TABLE 220

Inventive compounds of the formula (I) in which Q is Q3, R⁸ is methyl, X is chlorine; W is C—Y, Y is methylsulfanyl, V is hydrogen and Z is methylsulfonyl, and R is as defined in table 1:

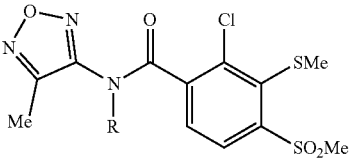

TABLE 221

Inventive compounds of the formula (I) in which Q is Q3, R⁸ is methyl, X is chlorine; W is C—Y, Y is methylsulfinyl, V is hydrogen and Z is methylsulfonyl, and R is as defined in table 1:

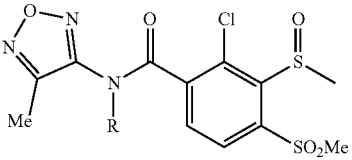

TABLE 222

Inventive compounds of the formula (I) in which Q is Q3, R⁸ is chlorine, X is chlorine, W is C—Y, Y is methylsulfinyl, V is hydrogen and Z is methylsulfonyl, and R is as defined in table 1:

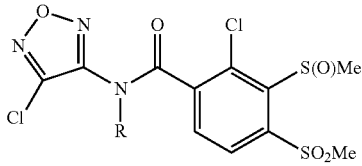

TABLE 223

Inventive compounds of the formula (I) in which Q is Q3, R⁸ is methoxymethyl, X is chlorine, W is C—Y, Y is methylsulfinyl, V is hydrogen and Z is methylsulfonyl, and R is as defined in table 1:

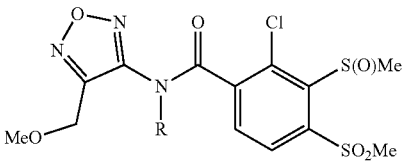

TABLE 224

Inventive compounds of the formula (I) in which Q is Q3, R⁸ is methyl, X is chlorine, W is C—Y, Y is ethylsulfinyl, V is hydrogen and Z is methylsulfonyl, and R is as defined in table 1:

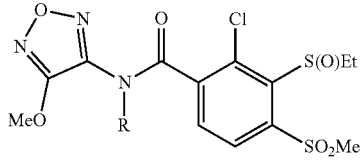

TABLE 225

Inventive compounds of the formula (I) in which Q is Q3, R⁸ is methyl, X is chlorine, W is C—Y, Y is methylsulfonyl, V is hydrogen and Z is methylsulfonyl, and R is as defined in table 1:

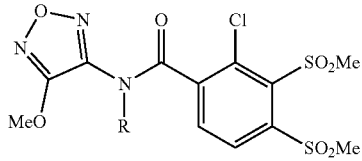

TABLE 226

Inventive compounds of the formula (I) in which Q is Q3, R⁸ is chlorine, X is chlorine, W is C—Y, Y is methylsulfonyl, V is hydrogen and Z is methylsulfonyl, and R is as defined in table 1:

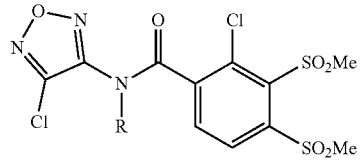

TABLE 227

Inventive compounds of the formula (I) in which Q is Q3, $R^8$ is methoxymethyl, X is chlorine; W is C—Y, Y is methylsulfonyl, V is hydrogen and Z is methylsulfonyl, and R is as defined in table 1:

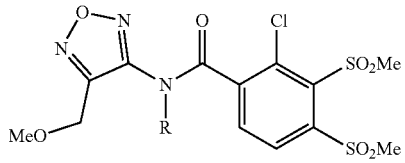

TABLE 228

Inventive compounds of the formula (I) in which Q is Q3, $R^8$ is methyl, X is chlorine; W is C—Y, Y is 5-cyanomethyl-4,5-dihydro-1,2-oxazol-3-yl, V is hydrogen and Z is ethylsulfonyl, and R is as defined in table 1:

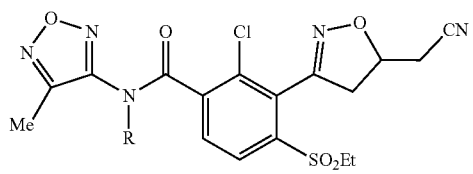

TABLE 229

Inventive compounds of the formula (I) in which Q is Q3, $R^8$ is methoxy, X is chlorine; W is C—Y, Y is 5-cyanomethyl-4,5-dihydro-1,2-oxazol-3-yl, V is hydrogen and Z is ethylsulfonyl, and R is as defined in table 1:

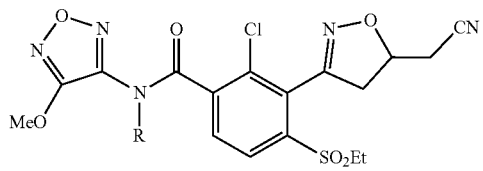

TABLE 230

Inventive compounds of the formula (I) in which Q is Q3, $R^8$ is methyl, X is chlorine; W is C—Y, Y is 5-methoxymethyl-4,5-dihydro-1,2-oxazol-3-yl, V is hydrogen and Z is ethylsulfonyl, and R is as defined in table 1:

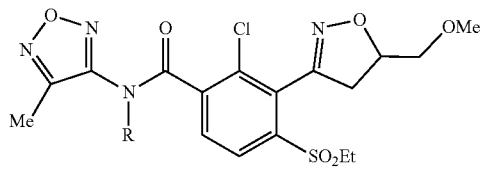

TABLE 231

Inventive compounds of the formula (I) in which Q is Q3, $R^8$ is methyl, X is methyl, W is C—Y, Y is 1H-pyrazol-1-yl, V is hydrogen and Z is methylsulfonyl, and R is as defined in table 1:

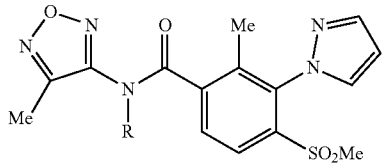

TABLE 232

Inventive compounds of the formula (I) in which Q is Q3, $R^8$ is ethyl, X is methyl, W is C—Y, Y is 1H-pyrazol-1-yl, V is hydrogen and Z is methylsulfonyl, and R is as defined in table 1:

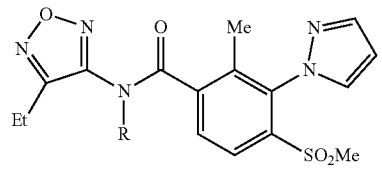

TABLE 233

Inventive compounds of the formula (I) in which Q is Q3, $R^8$ is chlorine, X is methyl, W is C—Y, Y is 1H-pyrazol-1-yl, V is hydrogen and Z is methylsulfonyl, and R is as defined in table 1:

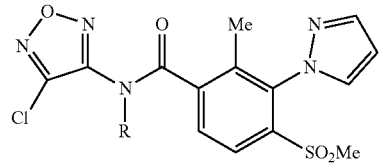

TABLE 234

Inventive compounds of the formula (I) in which Q is Q3, $R^8$ is methyl, X is methyl, W is C—Y, Y is methylsulfanyl, V is hydrogen and Z is methylsulfonyl, and R is as defined in table 1:

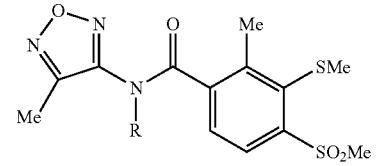

TABLE 235

Inventive compounds of the formula (I) in which Q is Q3, $R^8$ is chlorine, X is methyl, W is C—Y, Y is methylsulfanyl, V is hydrogen and Z is methylsulfonyl, and R is as defined in table 1:

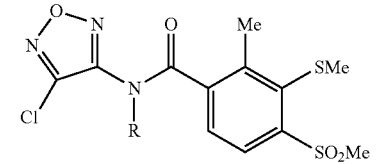

TABLE 236

Inventive compounds of the formula (I) in which Q is Q3,
R⁸ is methyl, X is methyl, W is C—Y, Y is methylsulfinyl,
V is hydrogen and Z is methylsulfonyl, and R is as defined in table 1:

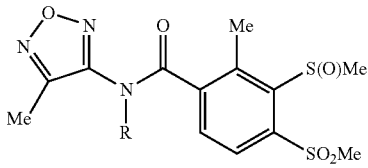

TABLE 237

Inventive compounds of the formula (I) in which Q is Q3, R⁸ is
chlorine, X is methyl, W is C—Y, Y is methylsulfinyl, V is
hydrogen and Z is methylsulfonyl, and R is as defined in table 1:

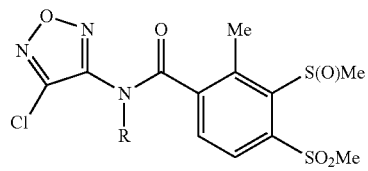

TABLE 238

Inventive compounds of the formula (I) in which Q is Q3, R⁸ is
methyl, X is methyl, W is C—Y, Y is methylsulfonyl, V is
hydrogen and Z is methylsulfonyl, and R is as defined in table 1:

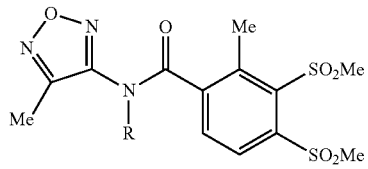

TABLE 239

Inventive compounds of the formula (I) in which Q is Q3, R⁸ is
chlorine, X is methyl, W is C—Y, Y is methylsulfonyl, V is
hydrogen and Z is methylsulfonyl, and R is as defined in table 1:

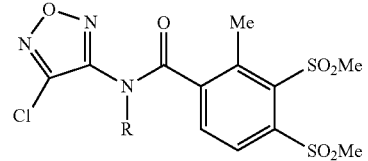

TABLE 240

Inventive compounds of the formula (I) in which Q is Q3, R⁸ is
cyclopropyl, X is methyl, W is C—Y, Y is methylsulfonyl, V is
hydrogen and Z is methylsulfonyl, and R is as defined in table 1:

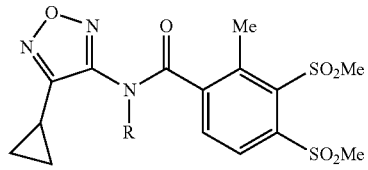

TABLE 241

Inventive compounds of the formula (I) in which Q is Q3, R⁸ is
methyl, X is methyl, W is C—Y, Y is (2-methoxyethyl)sulfonyl, V is
hydrogen and Z is methylsulfonyl, and R is as defined in table 1:

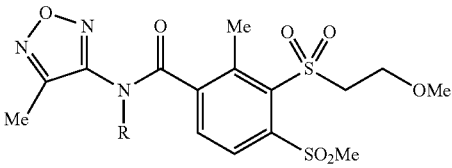

TABLE 242

Inventive compounds of the formula (I) in which Q is Q3, R⁸ is
chlorine, X is methyl, W is C—Y, Y is (2-methoxyethyl)sulfonyl, V is
hydrogen and Z is methylsulfonyl, and R is as defined in table 1:

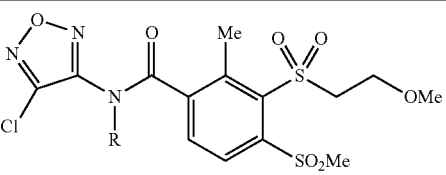

TABLE 243

Inventive compounds of the formula (I) in which Q is Q3, R⁸ is
methyl, X is methyl, W is C—Y, Y is ethylsulfonyl, V is
hydrogen and Z is methylsulfonyl, and R is as defined in table 1:

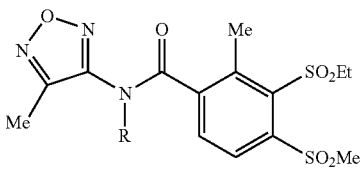

TABLE 244

Inventive compounds of the formula (I) in which Q is Q3, R⁸ is
ethyl, X is methyl, W is C—Y, Y is ethylsulfonyl, V is hydrogen
and Z is methylsulfonyl, and R is as defined in table 1:

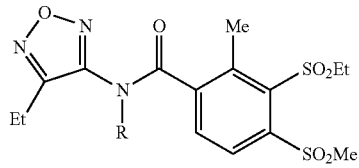

TABLE 245

Inventive compounds of the formula (I) in which Q is Q3, R⁸ is
chlorine, X is methyl, W is C—Y, Y is ethylsulfonyl, V is hydrogen
and Z is methylsulfonyl, and R is as defined in table 1:

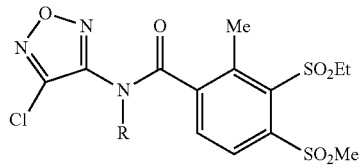

TABLE 246

Inventive compounds of the formula (I) in which Q is Q3, $R^8$ is amino, X is methyl, W is C—Y, Y is ethylsulfonyl, V is hydrogen and Z is methylsulfonyl, and R is as defined in table 1:

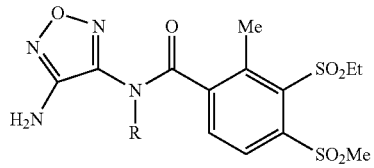

TABLE 247

Inventive compounds of the formula (I) in which Q is Q3, $R^8$ is acetylamino, X is methyl, W is C—Y, Y is methylsulfonyl, V is hydrogen and Z is methylsulfonyl, and R is as defined in table 1:

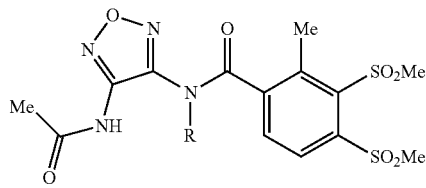

TABLE 248

Inventive compounds of the formula (I) in which Q is Q3, $R^8$ is methoxy, X is methyl, W is C—Y, Y is methylsulfonyl, V is hydrogen and Z is methylsulfonyl, and R is as defined in table 1:

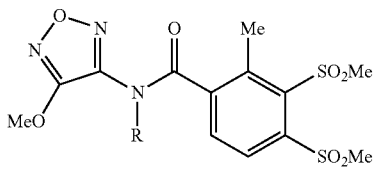

TABLE 249

Inventive compounds of the formula (I) in which Q is Q3, $R^8$ is methyl, X is methyl, W is C—Y, Y is methylsulfanyl, V is hydrogen and Z is trifluoromethyl, and R is as defined in table 1:

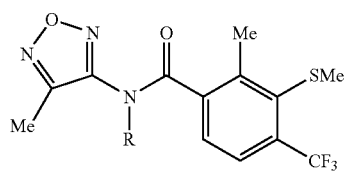

TABLE 250

Inventive compounds of the formula (I) in which Q is Q3, $R^8$ is chlorine, X is methyl, W is C—Y, Y is methylsulfanyl, V is hydrogen and Z is trifluoromethyl, and R is as defined in table 1:

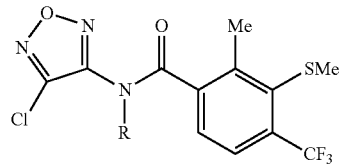

TABLE 251

Inventive compounds of the formula (I) in which Q is Q3, $R^8$ is methyl, X is methyl, W is C—Y, Y is methylsulfinyl, V is hydrogen and Z is trifluoromethyl, and R is as defined in table 1:

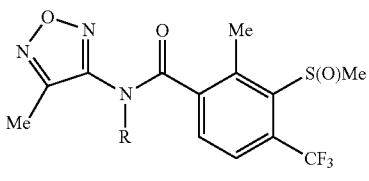

TABLE 252

Inventive compounds of the formula (I) in which Q is Q3, $R^8$ is chlorine, X is methyl, W is C—Y, Y is methylsulfinyl, V is hydrogen and Z is trifluoromethyl, and R is as defined in table 1:

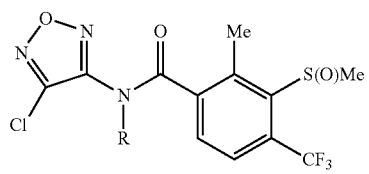

TABLE 253

Inventive compounds of the formula (I) in which Q is Q3, $R^8$ is methoxymethyl, X is methyl, W is C—Y, Y is methylsulfinyl, V is hydrogen and Z is trifluoromethyl, and R is as defined in table 1:

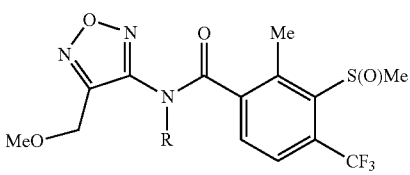

TABLE 254

Inventive compounds of the formula (I) in which Q is Q3, $R^8$ is 1H-1,2,4-triazol-1-yl, X is methyl, W is C—Y, Y is methylsulfinyl, V is hydrogen and Z is trifluoromethyl, and R is as defined in table 1:

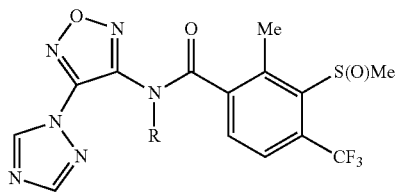

TABLE 255

Inventive compounds of the formula (I) in which Q is Q3, $R^8$ is methyl, X is methyl, W is C—Y, Y is methylsulfonyl, V is hydrogen and Z is trifluoromethyl, and R is as defined in table 1:

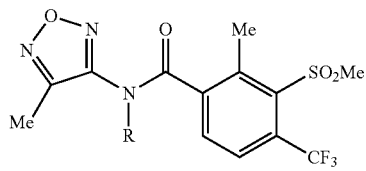

TABLE 256

Inventive compounds of the formula (I) in which Q is Q3, $R^8$ is chlorine, X is methyl, W is C—Y, Y is methylsulfonyl, V is hydrogen and Z is trifluoromethyl, and R is as defined in table 1:

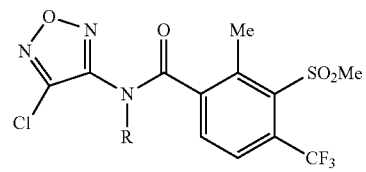

TABLE 257

Inventive compounds of the formula (I) in which Q is Q3, $R^8$ is methylsulfanyl, X is methyl, W is C—Y, Y is methylsulfonyl, V is hydrogen and Z is trifluoromethyl, and R is as defined in table 1:

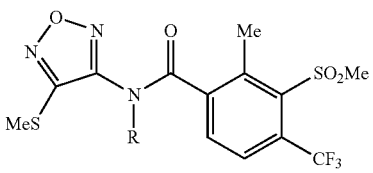

TABLE 258

Inventive compounds of the formula (I) in which Q is Q3, $R^8$ is nitro, X is methyl, W is C—Y, Y is methylsulfonyl, V is hydrogen and Z is trifluoromethyl, and R is as defined in table 1:

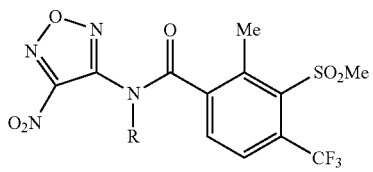

TABLE 259

Inventive compounds of the formula (I) in which Q is Q3, $R^8$ is methoxymethyl, X is methyl, W is C—Y, Y is methylsulfonyl, V is hydrogen and Z is trifluoromethyl, and R is as defined in table 1:

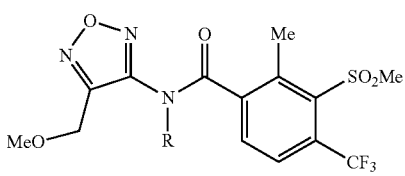

TABLE 260

Inventive compounds of the formula (I) in which Q is Q3, $R^8$ is (1H-pyrazol-1-yl)methyl, X is methyl, W is C—Y, Y is methylsulfonyl, V is hydrogen and Z is trifluoromethyl, and R is as defined in table 1:

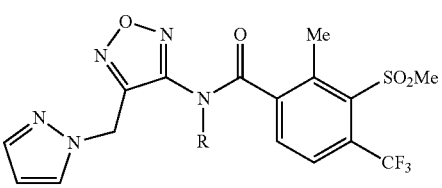

TABLE 261

Inventive compounds of the formula (I) in which Q is Q3, $R^8$ is acetylamino, X is methyl, W is C—Y, Y is methylsulfonyl, V is hydrogen and Z is trifluoromethyl, and R is as defined in table 1:

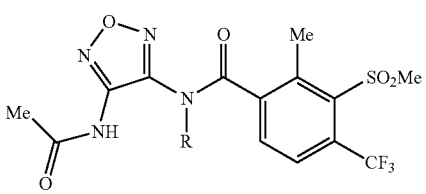

TABLE 262

Inventive compounds of the formula (I) in which Q is Q3, R$^8$ is (2,2-dimethylpropanoyl)amino, X is methyl, W is C—Y, Y is methylsulfonyl, V is hydrogen and Z is trifluoromethyl, and R is as defined in table 1:

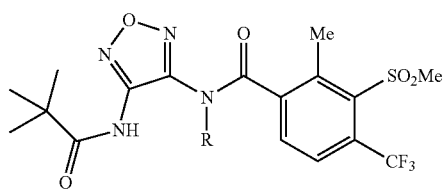

TABLE 263

Inventive compounds of the formula (I) in which Q is Q3, R$^8$ is methyl, X is methyl, W is C—Y, Y is ethylsulfinyl, V is hydrogen and Z is trifluoromethyl, and R is as defined in table 1:

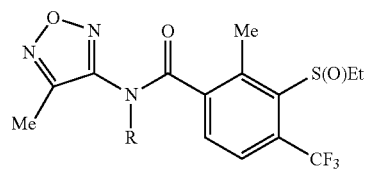

TABLE 264

Inventive compounds of the formula (I) in which Q is Q3, R$^8$ is chlorine, X is methyl, W is C—Y, Y is ethylsulfanyl, V is hydrogen and Z is trifluoromethyl, and R is as defined in table 1:

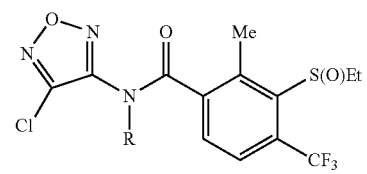

TABLE 265

Inventive compounds of the formula (I) in which Q is Q3, R$^8$ is methyl, X is ethyl, W is C—Y, Y is methylsulfonyl, V is hydrogen and Z is trifluoromethyl, and R is as defined in table 1:

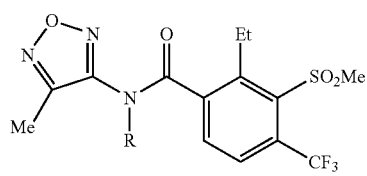

TABLE 266

Inventive compounds of the formula (I) in which Q is Q3, R$^8$ is methyl, X is methoxy, W is C—Y, Y is methylsulfanyl, V is hydrogen and Z is methylsulfonyl, and R is as defined in table 1:

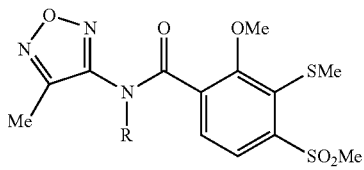

TABLE 267

Inventive compounds of the formula (I) in which Q is Q3, R$^8$ is methyl, X is methoxy, W is C—Y, Y is methylsulfinyl, V is hydrogen and Z is methylsulfonyl, and R is as defined in table 1:

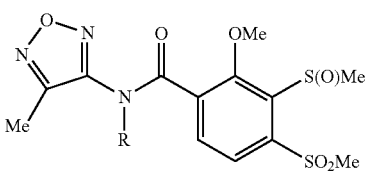

TABLE 268

Inventive compounds of the formula (I) in which Q is Q3, R$^8$ is methyl, X is methoxy, W is C—Y, Y is methylsulfonyl, V is hydrogen and Z is methylsulfonyl, and R is as defined in table 1:

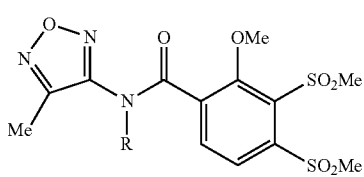

TABLE 269

Inventive compounds of the formula (I) in which Q is Q3, R$^8$ is methyl, X is methoxy, W is C—Y, Y is methylsulfanyl, V is hydrogen and Z is trifluoromethyl, and R is as defined in table 1:

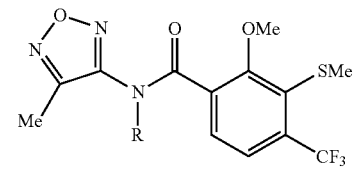

TABLE 270

Inventive compounds of the formula (I) in which Q is Q3, R⁸ is methyl, X is methoxy, W is C—Y, Y is methylsulfinyl, V is hydrogen and Z is trifluoromethyl, and R is as defined in table 1:

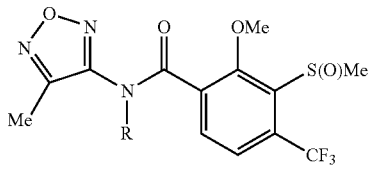

TABLE 271

Inventive compounds of the formula (I) in which Q is Q3, R⁸ is methyl, X is methoxy, W is C—Y, Y is methylsulfonyl, V is hydrogen and Z is trifluoromethyl, and R is as defined in table 1:

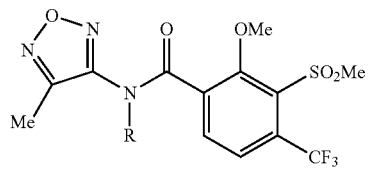

TABLE 272

Inventive compounds of the formula (I) in which Q is Q3, R⁸ is methyl, X is methoxymethyl, W is C—Y, Y is methylsulfanyl, V is hydrogen and Z is methylsulfonyl, and R is as defined in table 1:

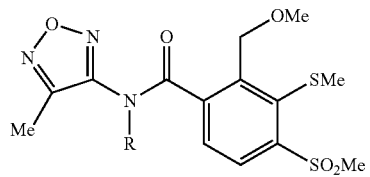

TABLE 273

Inventive compounds of the formula (I) in which Q is Q3, R⁸ is methyl, X is methoxymethyl, W is C—Y, Y is methylsulfinyl, V is hydrogen and Z is methylsulfonyl, and R is as defined in table 1:

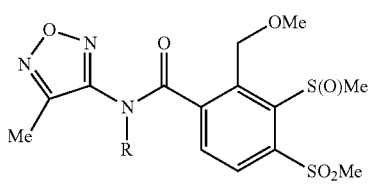

TABLE 274

Inventive compounds of the formula (I) in which Q is Q3, R⁸ is methyl, X is methoxymethyl, W is C—Y, Y is methylsulfonyl, V is hydrogen and Z is methylsulfonyl, and R is as defined in table 1:

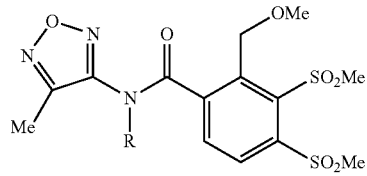

TABLE 275

Inventive compounds of the formula (I) in which Q is Q3, R⁸ is methyl, X is trifluoromethyl, W is C—Y, Y is methylsulfanyl, V is hydrogen and Z is trifluoromethyl, and R is as defined in table 1:

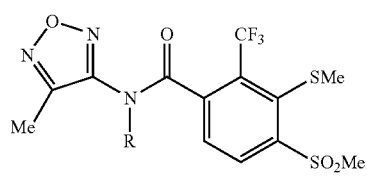

TABLE 276

Inventive compounds of the formula (I) in which Q is Q4, R⁹ is methyl, X is chlorine, W is N, V is hydrogen and Z is trifluoromethyl, and R is as defined in table 1:

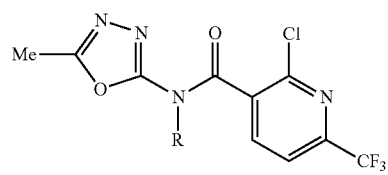

TABLE 277

Inventive compounds of the formula (I) in which Q is Q4, R⁹ is ethyl, X is chlorine, W is N, V is hydrogen and Z is trifluoromethyl, and R is as defined in table 1:

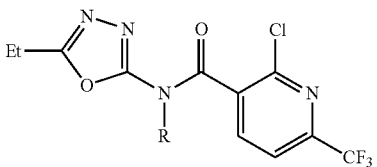

TABLE 278

Inventive compounds of the formula (I) in which Q is Q4, R⁹ is methoxymethyl, X is chlorine, W is N, V is hydrogen and Z is trifluoromethyl, and R is as defined in table 1:

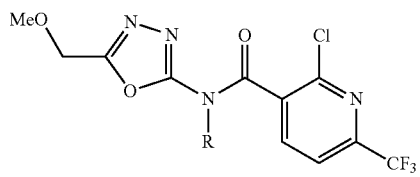

TABLE 279

Inventive compounds of the formula (I) in which Q is Q4, R⁹ is ethyl, X is methoxymethyl, W is N, V is hydrogen and Z is trifluoromethyl, and R is as defined in table 1:

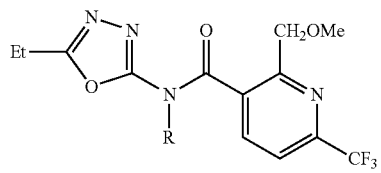

TABLE 280

Inventive compounds of the formula (I) in which Q is Q4, R⁹ is hydrogen, X is chlorine, W is C—Y, Y is (2,2,2-trifluoroethoxy)methyl, V is hydrogen and Z is methylsulfonyl, and R is as defined in table 1:

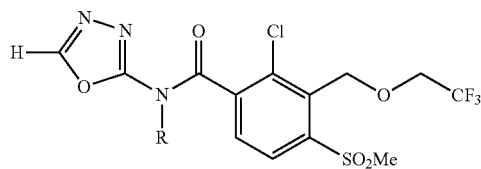

TABLE 281

Inventive compounds of the formula (I) in which Q is Q4, R⁹ is methyl, X is chlorine, W is C—Y, Y is (2,2,2-trifluoroethoxy)methyl, V is hydrogen and Z is methylsulfonyl, and R is as defined in table 1:

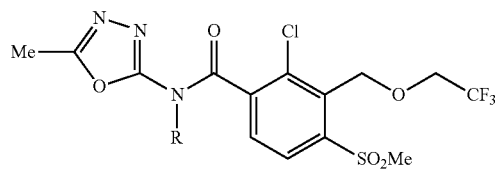

TABLE 282

Inventive compounds of the formula (I) in which Q is Q4, R⁹ is Isopropyl, X is chlorine, W is C—Y, Y is (2,2,2-trifluoroethoxy)methyl, V is hydrogen and Z is methylsulfonyl, and R is as defined in table 1:

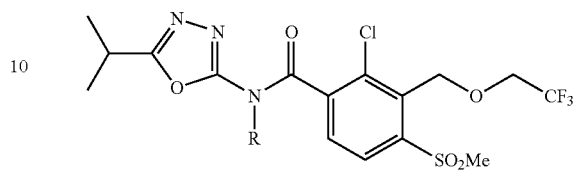

TABLE 283

Inventive compounds of the formula (I) in which Q is Q4, R⁹ is methyl, X is chlorine, W is C—Y, Y is propoxy, V is hydrogen and Z is methylsulfonyl, and R is as defined in table 1:

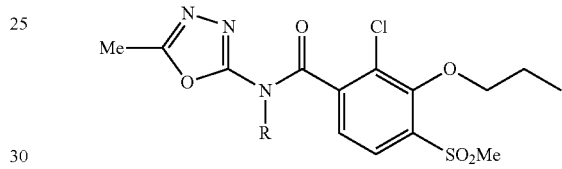

TABLE 284

Inventive compounds of the formula (I) in which Q is Q4, R⁹ is methyl, X is chlorine, W is C—Y, Y is cyclopropylmethoxy, V is hydrogen and Z is methylsulfonyl, and R is as defined in table 1:

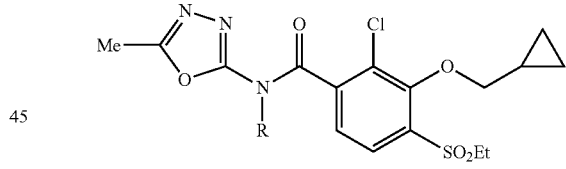

TABLE 285

Inventive compounds of the formula (I) in which Q is Q4, R⁹ is methyl, X is chlorine, W is C—Y, Y is 5-cyanomethyl-4,5-dihydro-1,2-oxazol-3-yl, V is hydrogen and Z is ethylsulfonyl, and R is as defined in table 1:

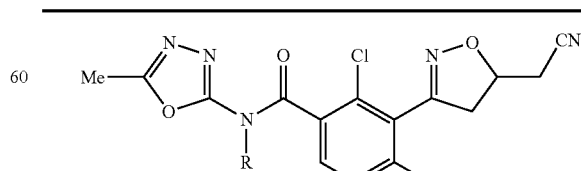

TABLE 286

Inventive compounds of the formula (I) in which Q is Q4, $R^9$ is ethyl, X is chlorine, W is C—Y, Y is 5-cyanomethyl-4,5-dihydro-1,2-oxazol-3-yl, V is hydrogen and Z is ethylsulfonyl, and R is as defined in table 1:

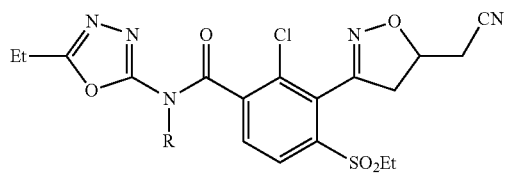

TABLE 287

Inventive compounds of the formula (I) in which Q is Q4, $R^9$ is methyl, X is chlorine, W is C—Y, Y is methylsulfonyl, V is hydrogen and Z is methylsulfonyl, and R is as defined in table 1:

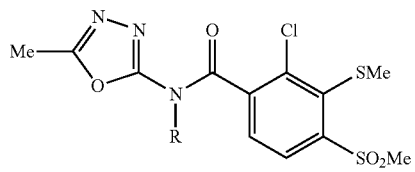

TABLE 288

Inventive compounds of the formula (I) in which Q is Q4, $R^9$ is ethyl, X is chlorine, W is C—Y, Y is methylsulfanyl, V is hydrogen and Z is methylsulfonyl, and R is as defined in table 1:

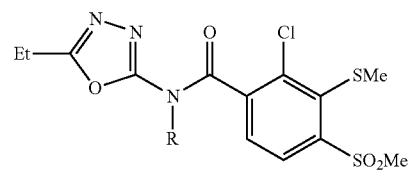

TABLE 289

Inventive compounds of the formula (I) in which Q is Q4, $R^9$ is methoxymethyl, X is chlorine, W is C—Y, Y is methylsulfanyl, V is hydrogen and Z is methylsulfonyl, and R is as defined in table 1:

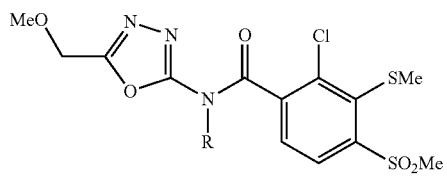

TABLE 290

Inventive compounds of the formula (I) in which Q is Q4, $R^9$ is methyl, X is chlorine, W is C—Y, Y is methylsulfinyl, V is hydrogen and Z is methylsulfonyl, and R is as defined in table 1:

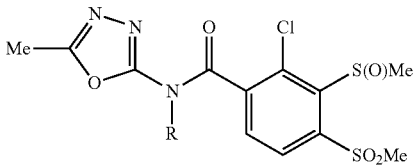

TABLE 291

Inventive compounds of the formula (I) in which Q is Q4, $R^9$ is ethyl, X is chlorine, W is C—Y, Y is methylsulfinyl, V is hydrogen and Z is methylsulfonyl, and R is as defined in table 1:

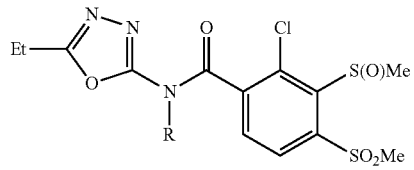

TABLE 291

Inventive compounds of the formula (I) in which Q is Q4, $R^9$ is methoxymethyl, X is chlorine, W is C—Y, Y is methylsulfinyl, V is hydrogen and Z is methylsulfonyl, and R is as defined in table 1:

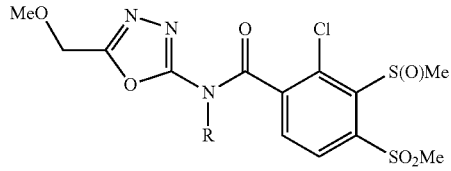

TABLE 292

Inventive compounds of the formula (I) in which Q is Q4, $R^9$ is methyl, X is chlorine, W is C—Y, Y is methylsulfonyl, V is hydrogen and Z is methylsulfonyl, and R is as defined in table 1:

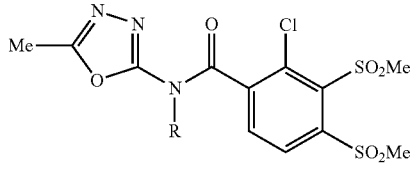

TABLE 293

Inventive compounds of the formula (I) in which Q is Q4, $R^9$ is ethyl, X is chlorine, W is C—Y, Y is methylsulfonyl, V is hydrogen and Z is methylsulfonyl, and R is as defined in table 1:

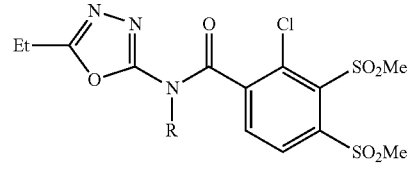

TABLE 294

Inventive compounds of the formula (I) in which Q is Q4, R⁹ is methoxymethyl, X is chlorine, W is C—Y, Y is methylsulfonyl, V is hydrogen and Z is methylsulfonyl, and R is as defined in table 1:

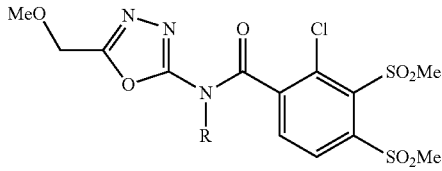

TABLE 295

Inventive compounds of the formula (I) in which Q is Q4, R⁹ is methyl, X is chlorine, W is C—Y, Y is methylsulfanyl, V is hydrogen and Z is trifluoromethyl, and R is as defined in table 1:

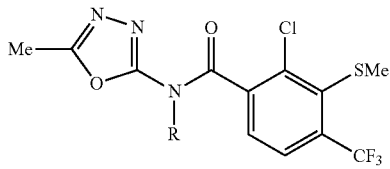

TABLE 296

Inventive compounds of the formula (I) in which Q is Q4, R⁹ is ethyl, X is chlorine, W is C—Y, Y is methylsulfanyl, V is hydrogen and Z is trifluoromethyl, and R is as defined in table 1:

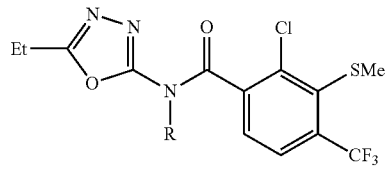

TABLE 297

Inventive compounds of the formula (I) in which Q is Q4, R⁹ is methoxymethyl, X is chlorine, W is C—Y, Y is methylsulfanyl, V is hydrogen and Z is trifluoromethyl, and R is as defined in table 1:

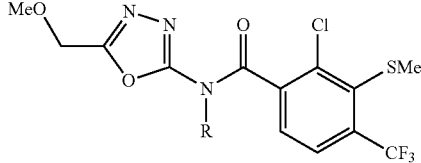

TABLE 298

Inventive compounds of the formula (I) in which Q is Q4, R⁹ is methyl, X is chlorine, W is C—Y, Y is methylsulfinyl, V is hydrogen and Z is trifluoromethyl, and R is as defined in table 1:

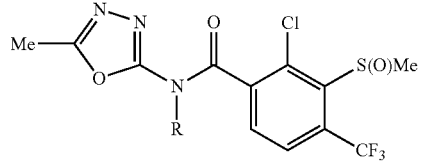

TABLE 299

Inventive compounds of the formula (I) in which Q is Q4, R⁹ is ethyl, X is chlorine, W is C—Y, Y is methylsulfinyl, V is hydrogen and Z is trifluoromethyl, and R is as defined in table 1:

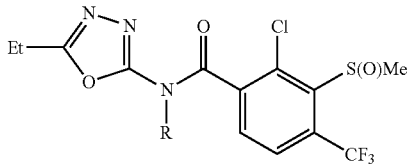

TABLE 300

Inventive compounds of the formula (I) in which Q is Q4, R⁹ is methoxymethyl, X is chlorine, W is C—Y, Y is methylsulfinyl, V is hydrogen and Z is trifluoromethyl, and R is as defined in table 1:

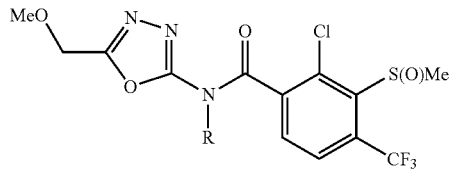

TABLE 301

Inventive compounds of the formula (I) in which Q is Q4, R⁹ is methyl, X is chlorine, W is C—Y, Y is methylsulfonyl, V is hydrogen and Z is trifluoromethyl, and R is as defined in table 1:

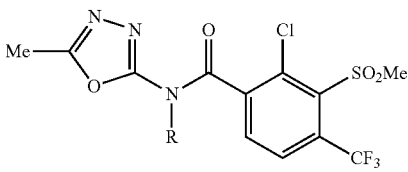

TABLE 302

Inventive compounds of the formula (I) in which Q is Q4, R⁹ is ethyl, X is chlorine, W is C—Y, Y is methylsulfonyl, V is hydrogen and Z is trifluoromethyl, and R is as defined in table 1:

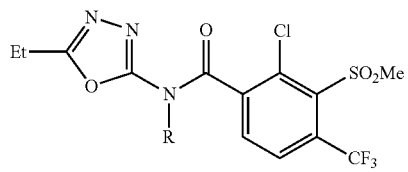

TABLE 303

Inventive compounds of the formula (I) in which Q is Q4, R$^9$ is methoxymethyl, X is chlorine, W is C—Y, Y is methylsulfonyl, V is hydrogen and Z is trifluoromethyl, and R is as defined in table 1:

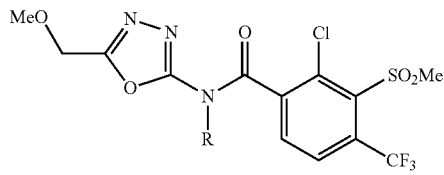

TABLE 304

Inventive compounds of the formula (I) in which Q is Q4, R$^9$ is ethyl, X is fluorine, W is C—Y, Y is methylsulfinyl, V is hydrogen and Z is trifluoromethyl, and R is as defined in table 1:

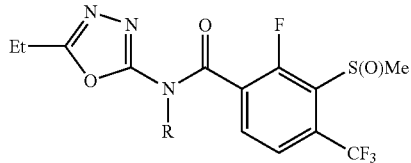

TABLE 305

Inventive compounds of the formula (I) in which Q is Q4, R$^9$ is methyl, X is bromine, W is C—Y, Y is methylsulfanyl, V is hydrogen and Z is methyl, and R is as defined in table 1:

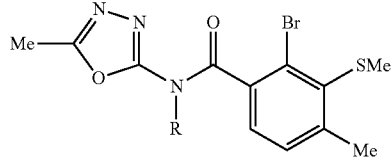

TABLE 306

Inventive compounds of the formula (I) in which Q is Q4, R$^9$ is methyl, X is bromine, W is C—Y, Y is methylsulfanyl, V is hydrogen and Z is methyl, and R is as defined in table 1:

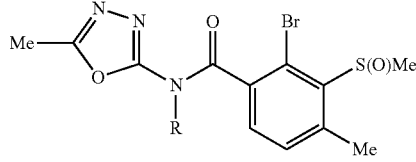

TABLE 307

Inventive compounds of the formula (I) in which Q is Q4, R$^9$ is methyl, X is methyl, W is C—Y, Y is methylsulfanyl, V is hydrogen and Z is trifluoromethyl, and R is as defined in table 1:

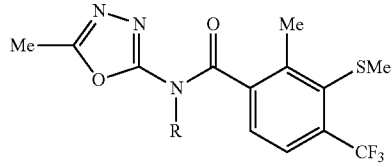

TABLE 308

Inventive compounds of the formula (I) in which Q is Q4, R$^9$ is ethyl, X is methyl, W is C—Y, Y is methylsulfanyl, V is hydrogen and Z is trifluoromethyl, and R is as defined in table 1:

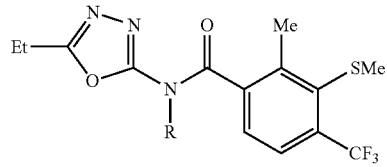

TABLE 309

Inventive compounds of the formula (I) in which Q is Q4, R$^9$ is methoxymethyl, X is methyl, W is C—Y, Y is methylsulfanyl, V is hydrogen and Z is trifluoromethyl, and R is as defined in table 1:

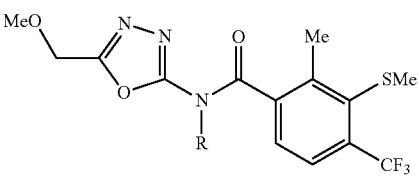

TABLE 310

Inventive compounds of the formula (I) in which Q is Q4, R$^9$ is methyl, X is methyl, W is C—Y, Y is methylsulfinyl, V is hydrogen and Z is trifluoromethyl, and R is as defined in table 1:

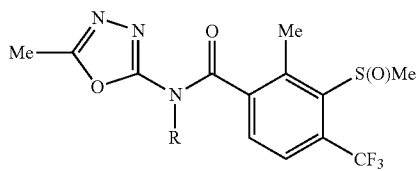

TABLE 311

Inventive compounds of the formula (I) in which Q is Q4, R$^9$ is cyclopropyl, X is methyl, W is C—Y, Y is methylsulfinyl, V is hydrogen and Z is trifluoromethyl, and R is as defined in table 1:

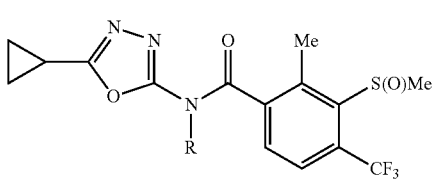

TABLE 312

Inventive compounds of the formula (I) in which Q is Q4, $R^9$ is trifluoromethyl, X is methyl, W is C—Y, Y is methylsulfinyl, V is hydrogen and Z is trifluoromethyl, and R is as defined in table 1:

TABLE 313

Inventive compounds of the formula (I) in which Q is Q4, $R^9$ is methyl, X is methyl, W is C—Y, Y is methylsulfonyl, V is hydrogen and Z is trifluoromethyl, and R is as defined in table 1:

TABLE 314

Inventive compounds of the formula (I) in which Q is Q4, $R^9$ is ethyl, X is methyl, W is C—Y, Y is methylsulfonyl, V is hydrogen and Z is trifluoromethyl, and R is as defined in table 1:

TABLE 315

Inventive compounds of the formula (I) in which Q is Q4, $R^9$ is methoxymethyl, X is methyl, W is C—Y, Y is methylsulfonyl, V is hydrogen and Z is trifluoromethyl, and R is as defined in table 1:

TABLE 316

Inventive compounds of the formula (I) in which Q is Q4, $R^9$ is ethoxymethyl, X is methyl, W is C—Y, Y is methylsulfonyl, V is hydrogen and Z is trifluoromethyl, and R is as defined in table 1:

TABLE 317

Inventive compounds of the formula (I) in which Q is Q4, $R^9$ is trifluoromethyl, X is methyl, W is C—Y, Y is methylsulfonyl, V is hydrogen and Z is trifluoromethyl, and R is as defined in table 1:

TABLE 318

Inventive compounds of the formula (I) in which Q is Q4, $R^9$ is 2,2,2-trifluoroethyl, X is methyl, W is C—Y, Y is methylsulfonyl, V is hydrogen and Z is trifluoromethyl, and R is as defined in table 1:

TABLE 319

Inventive compounds of the formula (I) in which Q is Q4, $R^9$ is methyl, X is methyl, W is C—Y, Y is methylsulfanyl, V is hydrogen and Z is methylsulfonyl, and R is as defined in table 1:

TABLE 320

Inventive compounds of the formula (I) in which Q is Q4, $R^9$ is ethyl, X is methyl, W is C—Y, Y is methylsulfanyl, V is hydrogen and Z is methylsulfonyl, and R is as defined in table 1:

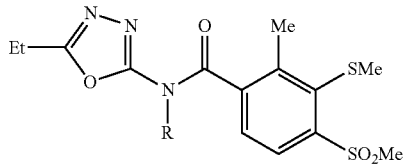

TABLE 321

Inventive compounds of the formula (I) in which Q is Q4, $R^9$ is methoxymethyl, X is methyl, W is C—Y, Y is methylsulfanyl, V is hydrogen and Z is methylsulfonyl, and R is as defined in table 1:

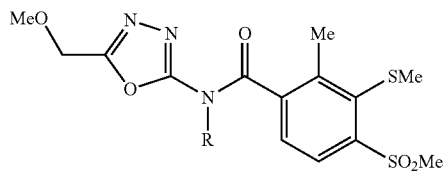

TABLE 322

Inventive compounds of the formula (I) in which Q is Q4, $R^9$ is methyl, X is methyl, W is C—Y, Y is methylsulfinyl, V is hydrogen and Z is methylsulfonyl, and R is as defined in table 1:

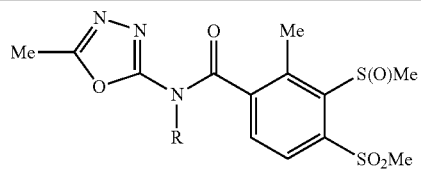

TABLE 323

Inventive compounds of the formula (I) in which Q is Q4, $R^9$ is ethyl, X is methyl, W is C—Y, Y is methylsulfinyl, V is hydrogen and Z is methylsulfonyl, and R is as defined in table 1:

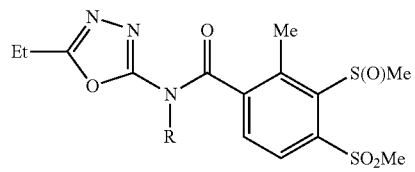

TABLE 324

Inventive compounds of the formula (I) in which Q is Q4, $R^9$ is V is hydrogen and Z ismethoxymethyl, X is methyl, W is C—Y, Y is methylsulfinyl, methylsulfonyl, and R is as defined in table 1:

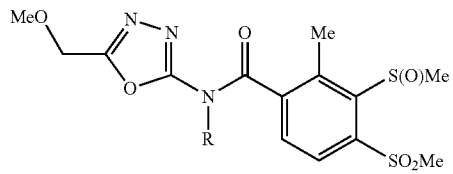

TABLE 325

Inventive compounds of the formula (I) in which Q is Q4, $R^9$ is methyl, X is methyl, W is C—Y, Y is methylsulfonyl, V is hydrogen and Z is methylsulfonyl, and R is as defined in table 1:

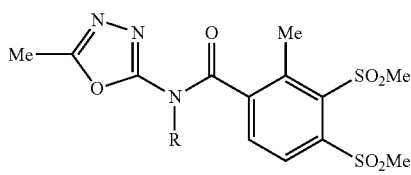

TABLE 326

Inventive compounds of the formula (I) in which Q is Q4, $R^9$ is ethyl, X is methyl, W is C—Y, Y is methylsulfonyl, V is hydrogen and Z is methylsulfonyl, and R is as defined in table 1

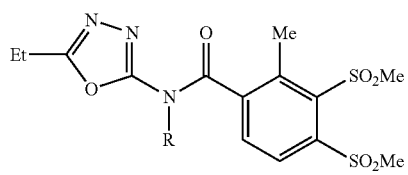

TABLE 327

Inventive compounds of the formula (I) in which Q is Q4, $R^9$ is methoxymethyl, X is methyl, W is C—Y, Y is methylsulfonyl, V is hydrogen and Z is methylsulfonyl, and R is as defined in table 1:

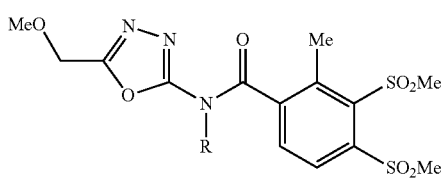

TABLE 328

Inventive compounds of the formula (I) in which Q is Q4, $R^9$ is methyl, X is methoxy, W is C—Y, Y is methylsulfanyl, V is hydrogen and Z is trifluoromethyl, and R is as defined in table 1:

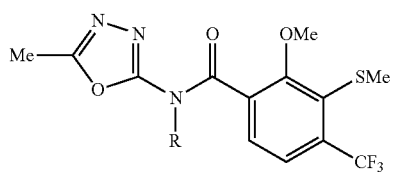

TABLE 329

Inventive compounds of the formula (I) in which Q is Q4, $R^9$ is methyl, X is methoxy, W is C—Y, Y is methylsulfinyl, V is hydrogen and Z is trifluoromethyl, and R is as defined in table 1:

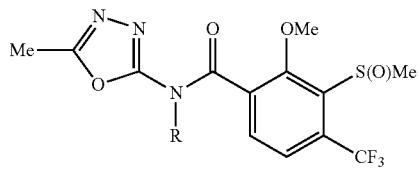

TABLE 330

Inventive compounds of the formula (I) in which Q is Q4, $R^9$ is methyl, X is methoxy, W is C—Y, Y is methylsulfonyl, V is hydrogen and Z is trifluoromethyl, and R is as defined in table 1:

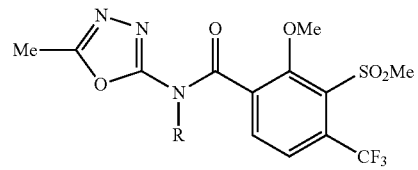

TABLE 331

Inventive compounds of the formula (I) in which Q is Q4, $R^9$ is methyl, X is methoxy, W is C—Y, Y is methylsulfanyl, V is hydrogen and Z is methylsulfonyl, and R is as defined in table 1:

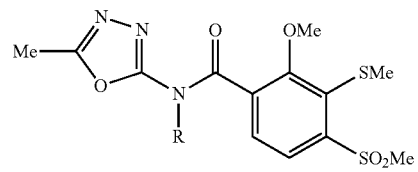

TABLE 332

Inventive compounds of the formula (I) in which Q is Q4, $R^9$ is methyl, X is methoxy, W is C—Y, Y is methylsulfinyl, V is hydrogen and Z is methylsulfonyl, and R is as defined in table 1:

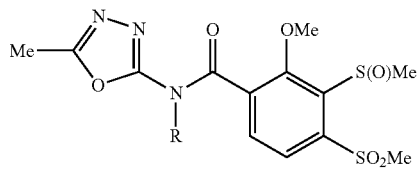

TABLE 333

Inventive compounds of the formula (I) in which Q is Q4, $R^9$ is methyl, X is methoxy, W is C—Y, Y is methylsulfonyl, V is hydrogen and Z is methylsulfonyl, and R is as defined in table 1:

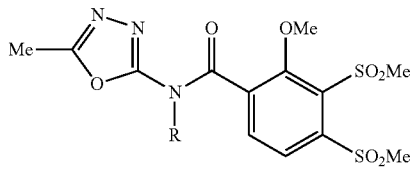

TABLE 334

Inventive compounds of the formula (I) in which Q is Q4, $R^9$ is methyl, X is methoxymethyl, W is C—Y, Y is methylsulfanyl, V is hydrogen and Z is methylsulfonyl, and R is as defined in table 1:

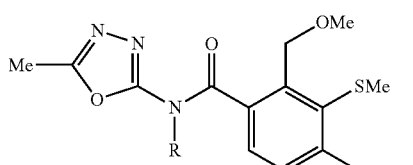

TABLE 335

Inventive compounds of the formula (I) in which Q is Q4, $R^9$ is methyl, X is methoxymethyl, W is C—Y, Y is methylsulfinyl, V is hydrogen and Z is methylsulfonyl, and R is as defined in table 1:

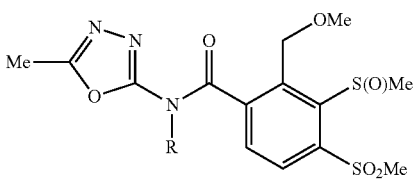

TABLE 336

Inventive compounds of the formula (I) in which Q is Q4, $R^9$ is methyl, X is methoxymethyl, W is C—Y, Y is methylsulfonyl, V is hydrogen and Z is methylsulfonyl, and R is as defined in table 1:

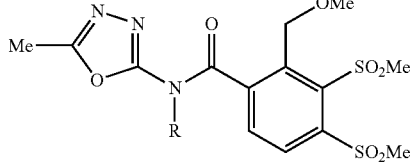

Very particular preference is given to the compounds of the general formula (I) listed in tables A, B, C and D, which can be obtained analogously to the methods specified here.

TABLE A

Inventive compounds of the formula (I) in which Q is Q1, V is hydrogen, and R, $R^6$, X, W, Z and V are each as defined in table A

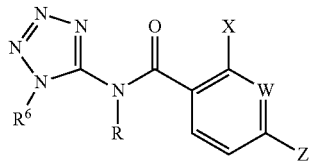

| No. | R | $R^6$ | X | W | Z | Physical data ($^1$H NMR, DMSO-$d_6$, 400 MHz) |
|---|---|---|---|---|---|---|
| A-1 | $CH_2OEt$ | Me | Me | C—$SO_2Me$ | $CF_3$ | 7.94; 7.78; 7.67 and 7.42; (4d, 2 H); 5.33 and 4.90 (2sb, 2H), 4.08 and 4.00 (2s, 3H), 3.86-3.72 and 3.41-3.16 (2m, 5H), 2.88 and 2.85 (2s, 3H), 1.31-1.02 (m, 3H) |
| A-2 | Et | Me | Me | C—$SO_2Me$ | $CF_3$ | 7.98; 7.69; 7.67 and 7.37; (4d, 2 H); 4.11-3.58 (m, 5H), 3.28 and 3.3,18 (2s, 3H), 3.83 (s, 3H), 1.32 and 1.12 (2t, 3H) |
| A-3 | Me | Me | Me | C—$SO_2Me$ | $CF_3$ | 7.98, 7.69, 7.38 (3bd, 2H), 4.07, 3.91 (2bs, 3H), 3.51, 3.37 (2bs, 3H), 3.28, 3.20 (2bs, 3H), 2.84 (s, 3H) |
| A-4 | Bn | Me | Me | C—$SO_2Me$ | $CF_3$ | 8.23, 8.05, 7.80, 7.76 (4d, 2H), 7.41-7.11 (m, 5H), 5.12, 4.83 (2bs, 2H), 4.02, 3.96 (2s, 3H), 3.34 (s, 3H), 2.68, 2.52 (2s, 3H) |
| A-5 | Me | Bn | Me | C—$SO_2Me$ | $CF_3$ | 8.06, 7.89, 7.61, 7.18 (4d, 2H), 7.43-7.29 (m, 5H), 5.73, 5.66 (2bs, 2H), 3.46, 3.42 (2s, 3H), 3.34, 3.13 (2s, 3H), 2.70, 2.65 (2s, 3H) |
| A-6 | Prg | Me | Me | C—SOMe | $CF_3$ | 7.79-7.25; (m, 2 H); 5.31 (bs, 2H), 3.95 (s, 3H), 2.96 (2s, 6H) |
| A-7 | $CH_2CO_2Me$ | Me | Me | C—SOMe | $CF_3$ | 7.72; 7.59; 7.46 and 7.31; (4d, 2 H); 5.02-4.93 and 4.60-4.31 (2m, 2H), 4.19 and 3.69 (2s, 3H), 3.82 (s, 3H), 3.01 (s, 3H), 2.97 (s, 3H) |
| A-8 | $CH_2CO_2Me$ | Me | Me | C—$SO_2Me$ | $CF_3$ | 7.94; 7.72; 7.68 and 7.47; (4d, 2 H); 4.80-4.33 (m, 2H), 4.19; 3.91; 3.84 and 3.69 (4s, 6H), 3.38 and 3.33 (2s, 3H), 2.90 and 2.82 (2s, 3H) |
| A-9 | allyl | Me | Me | C—$SO_2Me$ | $CF_3$ | 7.95; 7.69; 7.66 and 7.40; (4d, 2 H); 5.99-5.87 and 5.79-5.65 (2m, 1H), 5.33; 5.32; 5.19 and 5.01 (4d, 2H), 4.61-4.13 (m, 2H), 4.05 and 3.85 (2s, 3H), 3.28 and 3.19 (2s, 3H), 2.91 and 2.85 (2s, 3H), |
| A-10 | Prg | Prg | Cl | C—Cl | $SO_2Me$ | 8.02; (d, 1H); 7.67 (d, 1H), 5.60 (bs, 2H), 4.86 (bs, 2H), 3.52 (b, 1H), 3.43 (s, 3H), 3.34 (t, 1H) |
| A-11 | Me | Me | Me | C—$SO_2Me$ | $SO_2Me$ | 8.29; 8.12; 8.02; 7.75 (4db, 2 H); 3.67-3.54 (m, 6H); 3.46; 3.25 (2s, 3H); 2.70; 2.64 (2s, 3H), 2.47; 2.42 (2s, 3H) |
| A-12 | allyl | Me | Cl | C-(4,5-dihydro-5-acetonitrile-1,2-oxazol-4-yl | $SO_2Et$ | 8.23; 8.15; 7.90 and 7.82; (4d, 2 H); 5.88 (m, 1 H), 5.42-4.98 (m, 3H), 4.55 (bs, 1H), 4.29 (d, 1H), 4.10 and 4.04 (2s, 3H), 3.67-2.98 (m, 7H), 1.18 and 1.04 (2t, 3H) |
| A-13 | Me | $CO_2Me$ | Cl | C—OH | $SO_2Me$ | 9.39 (bs, 1H), 7.80 (d, 1H), 7.16 (d, 1H), 4.08 (s, 3H), 3.21 (s, 3H). |
| A-14 | Me | $CO_2Me$ | $SO_2Me$ | C—H | $CF_3$ | 8.40 (s, 1H), 8.31 (d, 1H), 8.15 (d, 1H), 4.14 (s, 3H), 3.67 (s, 3H); 3.38 (s, 3H). |
| A-15 | Me | $CO_2Et$ | $SO_2Me$ | C—H | $CF_3$ | $^1$H-NMR (400 MHz; DMSO-$d_6$): 8.40 (s, 1H), 8.32 (d, 1H), 8.16 d, 1H), 4.13 (s, 3H), 4.10 (q, 2H); 3.38 (s, 3H), 0.93 (t, 3H). |

TABLE A-continued

Inventive compounds of the formula (I) in which Q is Q1, V is hydrogen, and R, R⁶, X, W, Z and V are each as defined in table A

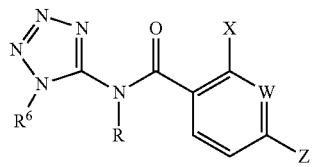

| No. | R | R⁶ | X | W | Z | Physical data ($^1$H NMR, DMSO-$d_6$, 400 MHz) |
|---|---|---|---|---|---|---|
| A-16 | Me | $CO_2$—i-Pr | $SO_2Me$ | C—H | $CF_3$ | 8.39 (s, 1H), 8.32 (d, 1H), 8.18 (d, 1H), 4.81 (m, 1H), 4.12 (s, 1H), 3.38 (s, 3H); 0.95 (d, 6H) |
| A-17 | Me | $CO_2CH_2CHMe_2$ | $SO_2Me$ | C—H | $CF_3$ | 8.40 (s, 1H), 8.31 (d, 1H), 8.19 (d, 1H), 4.14 (s, 3H), 3.88 (d, 2H), 3.38 (s, 3H); 1.62 (m, 1H), 0.62 (d, 6H) |
| A-18 | Me | $CO_2CH_2$—t-Bu | $SO_2Me$ | C—H | $CF_3$ | 8.40 (s, 1H), 8.32 (d, 1H), 8.22 (d, 1H), 4.15 (s, 3H), 3.38 (s, 3H); 0.63 (s, 9H) |

TABLE B

Inventive compounds of the formula (I) in which Q is Q2, V is hydrogen, and R, R⁷, X, W and Z are each as defined in table A

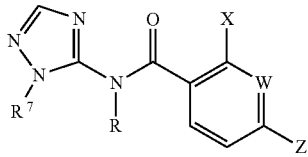

| No. | R | R⁷ | X | W | Z | Physical data ($^1$H NMR, DMSO-$d_6$, 400 MHz) |
|---|---|---|---|---|---|---|
| B-1 | | | | | | |

TABLE C

Inventive compounds of the formula (I) in which Q is Q1, V is hydrogen, and R, R⁸, X, W and Z are each as defined in table A

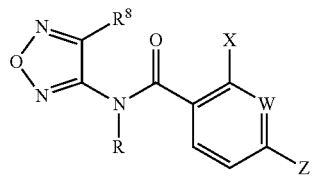

| No. | R | R⁸ | X | W | Z | Physical data ($^1$H NMR, DMSO-$d_6$, 400 MHz) |
|---|---|---|---|---|---|---|
| C-1 | allyl | Me | Me | C—$SO_2Me$ | $CF_3$ | 8.10-8.01 (b, 1 H); 7.83; 7.74 (2d, 1H); 5.98-5.75 (m, 1H); 5.38; 5.26 (2d, 1H); 5.14; 5.02 (2d, 1H); 4.19 (d, 2H); 3.46; 3.30 (2s, 3H), 2.89; 2.72 (2s; 3H); 2.43 (s, 3H) |
| C-2 | $CH_2CH_2CN$ | Me | Me | C—$SO_2Me$ | $CF_3$ | 8.12; 8.11; 7.87; 7.72 (4d, 2 H), 4.01-3.82 (m, 2H), 3.49-3.37 (m, 3H); 2.99-2.79 (m, 2H), 2.72 (s, 3H), 2.42; 2.41 (2s, 3H) |
| C-3 | Prg | Me | Me | C—$SO_2Me$ | $CF_3$ | 8.07; 7.83; 7.7,4; (3d, 2 H); 4.48; 4.44 (2bs, 2H), 3.46; 3.34 (2s, 3H); 3.74; 3.69 (2s, 3H); 2.43 (s, 3H) |
| C-4 | $CH_2CO_2Me$ | Me | Me | C—$SO_2Me$ | $CF_3$ | 8.85; 7.68; (2d, 2 H); 4.74 (bs, 2H), 3.76; 3.46 (2s, 3H); 3.42; 3.39 (2s, 3H); 2.74; 2.72 (2s, 3H), 2.42; 2.38 (2s, 3H) |
| C-5 | Me | Me | Me | C—$SO_2Me$ | $SO_2Me$ | 8.29; 8.12; 8.02; 7.75 (4db, 2 H); 3.67-3.54 (m, 6H); 3.46; 3.25 (2s, 3H); 2.70; 2.64 (2s, 3H), 2.47; 2.42 (2s, 3H) |

TABLE C-continued

Inventive compounds of the formula (I) in which Q is Q1,
V is hydrogen, and R, R$^8$, X, W and Z are each as defined in table A

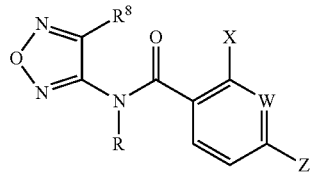

| No. | R | R$^8$ | X | W | Z | Physical data ($^1$H NMR, DMSO-d$_6$, 400 MHz) |
|---|---|---|---|---|---|---|
| C-6 | CH$_2$OEt | Me | Me | C—SO$_2$Me | CF$_3$ | 8.07 (bs, 1 H), 7.85 and 7.77 (2bs, 1H), 5.35 and 4.89 (2bs, 2H), 3.70 and 3.33 (2 bs, 3H), 3.42 (bq, 2H), 2.71 (s, 3H), 2.42 (s, 3H), 2.66 and 2.55 (2s, 3H), 2.36 (s, 3H) |
| C-7 | Bn | Me | Me | C—SO$_2$Me | CF$_3$ | 8.14, 8.02, 7.82 and 7.76 (4d, 2H), 7.40-7.08 (m, 5H), 5.25 and 4.82 (2bs, 2H), 3.32 (s, 3H), 1.17 and 1.01 (2t, 3H). |
| C-8 | Me | Me | Me | C—SO$_2$Me | CF$_3$ | BCAK20931-1-1 $^1$H NMR (400 MHz; DMSO-d$_6$): 7.96, and 7.36 (2bs, 1H), 7.68 (bs, 1H), 3.48-3.19 (4s, 6H), 2.82 (bs, 3H), 2.45 and 2.34 (2bs, 3H) |
| C-9 | Me | Et | Me | C—SO$_2$Me | CF$_3$ | 7.95 and 7.35 (bd, 1H), 7.68 (bs, 1H), 3.48, 3.30, 3.27 and 3.19 (4bs, 6H), 2.82-2.66 (m, 5H), 1.38 (t, 3H). |
| C-10 | Me | Cl | Cl | C—S(O)Me | CF$_3$ | 7.84-7.52 (m, 2H), 3.63-3.32 (m, 3H), 3.24-2.96 (m, 3H). |
| C-11 | Prg | Cl | Cl | C—SMe | CF$_3$ | 7.70 (bs, 1H), 7.50 (bs, 1H), 4.80 (bs, 2H), 2.45-2.33 (m, 4H). |
| C-12 | Prg | Me | Me | C—SO$_2$Me | SO$_2$Me | 8.41, 8.16, 7.81 and 7.45 (4bs, 2H), 4.73 and 4.37 (2bs, 2H), 3.57-3.42 (m, 6H), 2.87-2.77 (bs, 3H), 2.44-2.34 (m, 4H) |
| C-13 | Me | Cl | Cl | C—SMe | CF$_3$ | 7.68 and 7.49 (2bs, 2H), 3.50 (bs, 3H), 2.33 (bs, 3H). |

TABLE D

Inventive compounds of the formula (I) in which Q is Q4, V is
hydrogen, and R, R$^9$, X, W and Z are each as defined in table A

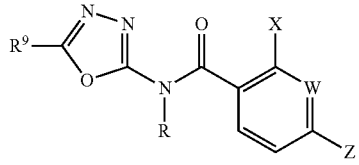

| No. | R | R$^9$ | X | W | Z | Physical data ($^1$H NMR, CDCl$_3$, 400 MHz) |
|---|---|---|---|---|---|---|
| D-1 | Me | Me | Me | C—SO$_2$Me | CF$_3$ | 7.98 (d, 1H), 7.49 (d, 1H), 3.57 (bs, 3H), 3.23 (s, 3H), 2.92 (s, 3H), 2.37 (s, 3H). |

B. FORMULATION EXAMPLES a) A dusting product is obtained by mixing 10 parts by weight of a compound of the formula (I) and/or salts thereof and 90 parts by weight of talc as inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
    75 parts by weight of a compound of the formula (I) and/or salts thereof,
    10 parts by weight of calcium lignosulfonate,
    5 parts by weight of sodium laurylsulfate,
    3 parts by weight of polyvinyl alcohol and
    7 parts by weight of kaolin,
    grinding the mixture in a pinned-disk mill, and granulating the powder in a fluidized bed by spray application of water as a granulating liquid.

f) Water-dispersible granules are also obtained by homogenizing and precomminuting
    25 parts by weight of a compound of the formula (I) and/or salts thereof,
    5 parts by weight of sodium 2,2'-dinaphthylmethane-6,6'-disulfonate,
    2 parts by weight of sodium oleoylmethyltaurate,
    1 part by weight of polyvinyl alcohol,
    17 parts by weight of calcium carbonate and
    50 parts by weight of water in a colloid mill, then grinding the mixture in a bead mill and atomizing and drying the resulting suspension in a spray tower by means of a one-phase nozzle.

C. BIOLOGICAL EXAMPLES

1. Pre-Emergence Herbicidal Action Against Weed Plants

Seeds of monocotyledonous and dicotyledonous weed plants and crop plants are placed in wood-fiber pots in sandy loam and covered with soil. The inventive compounds formulated in the form of wettable powders (WP) or as emulsion concentrates (EC) are then applied to the surface of the covering soil as an aqueous suspension or emulsion at a water application rate of 600 to 800 l/ha (converted) with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). For example, compounds no. A-2, A-3, A-4, A-5, A-6, C-1, C-3 and C-5 at an application rate of 320 g/ha each show at least 80% efficacy against *Stellaria media* and *Veronica persica*.

2. Post-Emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The inventive compounds formulated in the form of wettable powders (WP) or as emulsion concentrates (EC) are then sprayed onto the green parts of the plants as an aqueous suspension or emulsion at a water application rate of 600 to 800 l/ha (converted) with addition of 0.2% wetting agent. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). For example, compounds no. A-2, A-3, A-4, A-5, A-6, A-7, C-1, C-3 and C-5 at an application rate of 80 g/ha each show at least 80% efficacy against *Stellaria media* and *Amaranthus retroflexus*.

The invention claimed is:

1. An N-(tetrazol-5-yl)- arylcarboxamide of formula (I) and/or a salt thereof (I)

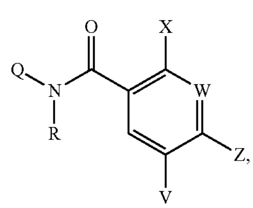

in which

R is methyl, ethyl, allyl, —CH2CO2Me, —CH2OEt, propargyl, or benzyl,

Y is hydrogen, SO2Me, OH, or chloro,

X and Z are independently methyl, chloro, CF3, SO2Me, or SO2Et,

W is CY,

V is hydrogen,

Q is a Q1, radical, (Q1)

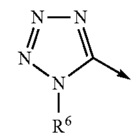

$R^6$ is $(C_1C_6)$-alkyl, halo-$(C_1C_6)$-alkyl, $(C_2$-$C_6)$-alkenyl, halo-$(C_2$-$C_6)$-alkenyl, $(C_2$-$C_6)$-alkynyl, halo-$(C_2$-$C_6)$-alkynyl, where these 6 aforementioned radicals are each substituted by s radicals from the group consisting of nitro, cyano, $SiR^{12}_3$, $PO(OR^{12})_3$, $S(O)_n$—$(C_1$-$C_6)$-alkyl, $(C_1$-$C_6)$-alkoxy, halo-$(C_1$-$C_6)$-alkoxy, $N(R^{10})_2$, $COR^{10}$, $COOR^{10}$, $OCOR^{10}$, $OCO_2R^{10}$, $NR^{10}COR^{10}$, $NR^{10}SO_2R^{11}$, $(C_3$-$C_6)$-cycloalkyl, phenyl,-D-phenyl or D-benzyl, and where the 3 latter radicals are substituted by s radicals from the group of methyl, ethyl, methoxy, trifluoromethyl and halogen, or $R^6$ is $(C_3C_7)$-cycloalkyl, or phenyl, each substituted by s radicals from the group consisting of halogen, nitro, cyano, $(C_1$-$C_6)$-alkyl, halo-$(C_1$-$C_6)$-alkyl, $(C_3$-$C_6)$-cycloalkyl, $S(O)_n$—$(C_1$-$C_6)$-alkyl, $(C_1$-$C_6)$-alkoxy, halo-$(C_1$-$C_6)$-alkoxy and $(C_1$-$C_6)$-alkoxy -$(C_1$-$C_4)$-alkyl, $R^{10}$ is hydrogen, $(C_1$-$C_6)$-alkyl, $(C_2$-$C_6)$-alkenyl, $(C_2$-$C_6)$-alkynyl, $(C_3$-$C_6)$-cycloalkyl or $(C_3$-$C_6)$-cycloalkyl-$(C_1$-$C_6)$-alkyl or phenyl, $R^{11}$ is $(C_1$-$C_6)$-alkyl, $(C_2$-$C_6)$-alkenyl, $(C_2$-$C_6)$-alkynyl or phenyl, $R^{12}$ is $(C_1$-$C_6)$-alkyl, D is O, S, or $NR^{11}$.

2. A herbicidal composition, comprising a herbicidally active content of at least one compound as claimed in claim 1 and a formulation assistant.

3. A method for controlling unwanted plants, which comprises applying an effective amount of at least one compound as claimed in claim 1 to a plant and/or a site of unwanted vegetation.

4. A compound as claimed in claim 1, wherein

R is allyl, —CH2CO2Me, —CH2OEt, propargyl, or benzyl,

Y is hydogen, SO2Me, OH, or chloro, and

X and Z are independently methyl, chloro, CF3, SO2Me, or SO2Et.

5. A compound as claimed in claim 1, wherein R is benzyl.

6. A compound as claimed in claim 1, wherein X and Z are each independently chloro, CF3, SO2Me, or SO2Et.

* * * * *